(12) United States Patent
Young et al.

(10) Patent No.: US 7,431,923 B2
(45) Date of Patent: Oct. 7, 2008

(54) CYTOTOXICITY MEDIATION OF CELLS EVIDENCING SURFACE EXPRESSION OF CD63

(75) Inventors: David S. F. Young, Toronto (CA); Susan E. Hahn, Toronto (CA); Helen P. Findlay, Toronto (CA); Luis A. G. da Cruz, Toronto (CA)

(73) Assignee: Arius Research Inc., Toronto, Ontario (CA)

(*) Notice: Subject to any disclaimer, the term of this patent is extended or adjusted under 35 U.S.C. 154(b) by 0 days.

(21) Appl. No.: 11/321,624

(22) Filed: Dec. 29, 2005

(65) Prior Publication Data

US 2006/0204497 A1  Sep. 14, 2006

Related U.S. Application Data

(60) Provisional application No. 60/642,057, filed on Jan. 3, 2005.

(51) Int. Cl.
A61K 39/395 (2006.01)
C07K 16/00 (2006.01)

(52) U.S. Cl. .................. 424/130.1; 530/387.1
(58) Field of Classification Search .............. None
See application file for complete search history.

(56) References Cited

U.S. PATENT DOCUMENTS

| | | | |
|---|---|---|---|
| 4,861,581 | A | 8/1989 | Epstein et al. |
| 5,171,665 | A | 12/1992 | Hellstrom et al. |
| 5,296,348 | A | 3/1994 | Rackowicz-Szulczynsk |
| 5,484,596 | A | 1/1996 | Hanna, Jr. et al. |
| 5,693,763 | A | 12/1997 | Codington et al. |
| 5,750,102 | A | 5/1998 | Eisenbach et al. |
| 5,780,033 | A | 7/1998 | Torchillin et al. |
| 5,783,186 | A | 7/1998 | Arakawa et al. |
| 5,849,876 | A | 12/1998 | Linsley et al. |
| 5,869,045 | A | 2/1999 | Hellstrom et al. |
| 5,869,268 | A | 2/1999 | Kudo et al. |
| 6,180,357 | B1 | 1/2001 | Young et al. |
| 6,245,898 | B1 | 6/2001 | Testa et al. |
| 6,783,961 | B1 | 8/2004 | Edwards et al. |
| 6,783,969 | B1 | 8/2004 | Tang et al. |
| 2002/0102638 | A1 | 8/2002 | Rosen et al. |
| 2003/0055220 | A1 | 3/2003 | Legrain |
| 2003/0148408 | A1 | 8/2003 | Frantz et al. |
| 2004/0105816 | A1 | 6/2004 | Young et al. |
| 2004/0141913 | A1 | 7/2004 | Young et al. |
| 2004/0141915 | A1 | 7/2004 | Young et al. |
| 2004/0197328 | A1 | 10/2004 | Young et al. |
| 2004/0198651 | A1 | 10/2004 | Klammer et al. |

FOREIGN PATENT DOCUMENTS

| | | |
|---|---|---|
| CN | 1326951 | 12/2001 |
| CN | 1326962 | 12/2001 |
| CN | 1351054 | 5/2002 |
| CN | 1364803 | 8/2002 |
| EP | 1 033 401 | 6/2000 |
| WO | WO 99/66027 | 12/1999 |
| WO | WO 00/05918 | 2/2000 |
| WO | WO 00/55180 | 9/2000 |
| WO | WO 01/75177 | 10/2001 |
| WO | WO 02/00677 | 1/2002 |
| WO | WO 02/055551 | 7/2002 |
| WO | WO 02/057303 | 7/2002 |
| WO | WO 02/070539 | 9/2002 |
| WO | WO 03/016475 | 2/2003 |
| WO | WO 03/057160 | 7/2003 |
| WO | WO 03/068268 | 8/2003 |
| WO | WO 03/070902 | 8/2003 |
| WO | WO 03/086456 | 10/2003 |
| WO | WO 2004/041170 | 5/2004 |

OTHER PUBLICATIONS

Didrik and Winter (Jun. 13, 2006, PNAS, 103(24):9172-9177).*
M. Adachi et al, "Novel staging protocol for non-small-cell lung cancers according to MRP-1/CD9 and KAII/CD82 gene expression", J. Clin. Oncol., 16(4):1397-1406 (Apr. 1998).
G. Andreola et al, "Induction of lymphocyte apoptosis by tumor cell secretion of FasL-bearing microvesicles", J. Exp. Med., 195(10):1303-1316 (May 2002).
B. Atkinson et al, "Monoclonal antibody to a highly glycosylated protein reacts in fixed tissue with melanoma and other tumors", Hybridoma, 4(3):243-255 (1985).
D. Azorsa et al, "A general approach to the generation of monoclonal antibodies against members of the tetraspanin superfamily using recombinant GST fusion proteins", J. Immunol. Meth., 229:35-48 (1999).
M. Barrio et al, "A new epitope on human melanoma-associated antigen CD63/ME491 expressed by both primary and metastatic melanoma", Hybridoma, 17(4):355-364 (1998).
M. Barrio et al, "Monoclonal antibody FC-5.01, directed against CD63 antigen, is internalized into cytoplasmic vesicles in the IIB-BR-G human breast cancer cell line", Hybridoma, 17(6):517-523 (1998).
F. Berditchevski et al, "Characterization of integrin-tetraspanin adhesion complexes: role of tetraspanins in integrin signaling", J. Cell Biol., 146(2):477-492 (Jul. 1999).
F. Berditchevski et al, "A novel link between integrins, transmembrane-4 superfamily proteins (CD63 and CD81), and phosphatidylinositol 4-kinase", J. Biol. Chem., 272(5):2595-2598 (Jan. 1997).
F. Berditchevski et al, "Specific association of CD63 with the VLA-3 and VLA-6 integrins", J. Biol. Chem., 270(30):17784-11790 (Jul. 1995).

(Continued)

Primary Examiner—Misook Yu
Assistant Examiner—Sean E Aeder
(74) Attorney, Agent, or Firm—McHale & Slavin, P.A.

(57) ABSTRACT

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays which utilize the CDMABs of the instant invention.

6 Claims, 40 Drawing Sheets
(12 of 40 Drawing Sheet(s) Filed in Color)

OTHER PUBLICATIONS

D. Blakey et al, "Antitumor activity of the novel vascular targeting agent ZD6126 in a panel of tumor models", Clinical Cancer Research, 8:1974-1983 (Jun. 2002).

A. Carmo et al, "Association of the transmembrane 4 superfamily molecule CD53 with a tyrosine phosphatase activity", Eur. J. Immunol., 25:2090-2095 (1995).

C. Claas et al, "Evaluation of prototype transmembrane 4 superfamily protein complexes and their relation to lipid rafts", J. Biol. Chem., 276(11):7974-7984 (Mar. 2001).

D. Demetrick et al, "ME491 melanoma-associated glycoprotein family: antigenic identity of ME491, NKI/C-3, neuroglandular antigen (NGA), and CD63 proteins", J. Natl Cancer Inst, 84(6):422-429 (Mar. 1992).

G. Eckhardt et al, "Developmental therapeutics: successes and failures of clinical trial designs of targeted compounds", In American Society of Clinical Oncology, pp. 209-219 (2003).

A. Engering et al, "Association of distinct tetraspanins with MHC class II molecules at different subcellular locations in human immature dendritic cells", International Immunology, 13(2):127-134 (2001).

J-M. Escola et al, "Selective enrichment of tetraspan proteins on the internal vesicles of multivesicular endosomes and on exosomes secreted by human B-lymphocytes", J. Biol. Chem., 273(32):20121-20127 (Aug. 1998).

S. Guichard et al, "Schedule-dependent activity of topotecan in OVCAR-3 ovarian carcinoma xenograft: pharmacokinetic and pharmacodynamic evaluation", Clinical Cancer Research, 7:3222-3228 (Oct. 2001).

N. Guilbaud et al, "Marked antitumor activity of a new potent acronycine derivative in orthotopic models of human solid tumors", Clinical Cancer Research, 7:2573-2580 (Aug. 2001).

C. Hammond et al, "The tetraspan protein CD82 is a resident of MHC class II compartments where it associates with HLA-DR, -DM, and -DO molecules", J. Immunol, 161:3282-3291 (1998).

J. Hildreth et al, "Characterization of a novel self-associating Mr 40,000 platelet glycoprotein", Blood, 77(1):121-132 (Jan. 1991).

S. Hirschfeld et al, "Oncology drug development: United States Food and Drug Administration perspective", Critical Reviews in Oncology/Hematology, 42:137-143 (2002).

H. Hotta et al, "Genomic structure of the ME491/CD63 antigen gene and functional analysis of the 5'-flanking regulatory sequences", Biochem Biophys Res Comm, 185(1):436-442 (May 1992).

H. Hotta et al, "Molecular cloning and characterization of an antigen associated with early stages of melanoma tumor progression", Cancer Research, 48:2955-2962 (Jun. 1988).

H. Hotta et al, "Overexpression of the human melanoma-associated antigen ME491 patially suppresses in vivo malignant phenotypes of H-ras-transformed NIH3T3 cells in athymic nude mice", Melanoma Research, 1:125-132 (1991).

C. Huang et al, "Correlation of reduction in MRP-1/CD9 and KAI1/CD82 expression with recurrences in breast cancer patients", Am J Pathol, 153(3):973-983 (Sep. 1998).

H-I. Jang et al, "A decrease in the expression of CD63 tetraspanin protein elevates invasive potential of human melanoma cells", Experimental and Molecular Medicine, 35(4):317-323 (Aug. 2003).

C. Joyner et al, "Identification and enrichment of human osteoprogenitor cells by using differentiation stage-specific monoclonal antibodies", Bone, 21(1):1-6 (Jul. 1997).

T. Karpanen et al, "Vascular endothelial growth factor C promotes tumor lymphangiogenesis and intralymphatic tumor growth", Cancer Research, 61:1786-1790 (Mar. 2001).

S. Kennel et al, "Monoclonal antibody to rat CD63 detects different molecular forms in rat tissue", Hybridoma, 17(6):509-515 (1998).

G. Klement et al, "Differences in therapeutic indexes of combination metronomic chemotherapy and an anti-VEGFR-2 antibody in multidrug-resistant human breast cancer xenografts", Clinical Cancer Research, 8:221-232 (Jan. 2002).

T. Kobayashi et al, "The tetraspanin CD63/lamp3 cycles between endocytic and secretory compartments in human endothelial cells", Molecular Biology of the Cell, 11:1829-1843 (May 2000).

M. Kondoh et al, "Decreased expression of human melanoma-associated antigen ME491 along the progression of melanoma pre-canceroses to invasive and metastatic melanomas", Melanoma Research, 3:241-245 (1993).

Y. Koyama et al, "A novel monoclonal antibody induces the differentiation of monocyte leukemic cells", Biochem Biophys Res Comm, 168(3):898-904 (May 1990).

Y. Koyama et al, "CD63, a member of tetraspan transmembrane protein family, induces cellular spreading by reaction with monoclonal antibody on substrata", Biochem Biophys Res Comm, 246(3):841-846 (1998).

S. Lebel-Binay et al, "CD82, member of the tetra-span-transmembrane protein family, is a costimulatory protein for T cell activation", J. Immunol., 155:101-110 (1995).

J. Li et al, "Recombinant CD63/ME491/neuroglandular/NKI/C-3 antigen Inhibits growth of established tumors in transgenic mice", J. Immunol., 171:2922-2929 (2003).

B. Mannion et al, "Transmembrane-4 superfamily proteins CD81 (TAPA-1), CD82, CD63, and CD53 specifically associate with integrin alpha4beta1 (CD49d/CD29)", J. Immunol., 157:2039-2047 (1996).

T. Martin, "Phosphoinositide lipids as signaling molecules: common themes for signal transduction, cytoskeletal regulation, and membrane trafficking", Annu. Rev. Cell Dev. Biol., 14:231-264 (1998).

M. Martinez-Lorenzo et al, "Unusual intracellular trafficking of salmonella typhimurium in human melanoma cells", Cellular Microbiology, 3(6):407-416 (2001).

M. Metzelaar et al, "CD63 antigen", J. Biol. Chem., 266(5):3239-3245 (Feb. 1991).

H. Nieuwenhuis et al, "Studies with a monoclonal antibody against activated platelets: evidence that a secreted 53,000-molecular weight lysosome-like granule protein is exposed on the surface of activated platelets in the circulation", Blood, 70(3):838-845 (Sep. 1987).

H. Okochi et al, "Expression of tetra-spans transmembrane family (CD9, CD37, CD53, CD63, CD81 and CD82) in normal and neoplastic human keratinocytes: an association of CD9 with alpha3beta 1 integrin", British Journal of Dermatology, 137:856-863 (1997).

K. Olson et al, "Inhibition of prostate carcinoma establishment and metastatic growth in mice by an antiangiogenin monoclonal antibody", Int. J. Cancer, 98:923-929 (2002).

P. Peters et al, "Cytotoxic T lymphocyte granules are secretory lysosomes, containing both perforin and granzymes", J. Exp. Med., 173:1099-1109 (May 1991).

K. Radford et al, "CD63 associates with transmembrane 4 superfamily members, CD9 and CD81, and with beta1 integrins in human melanoma", Biochem Biophys Res Comm, 222:13-18 (1996).

K. Radford et al, "Regulation of tumor cell motility and migration by CD63 in a human melanoma cell line", J. Immunol., 158:3353-3358 (1997).

K. Radford et al, "Suppression of human melanoma cell growth and metastasis by the melanoma-associated antigen CD63 (ME491)", Int. J. Cancer, 62:631-635 (1995).

E. Rubinstein et al, "CD9, CD63, CD81, and CD82 are components of a surface tetraspan network connected to HLA-DR and VLA integrins", Eur. J. Immunol., 26:2657-2665 (1996).

G. Sauer et al, "Expression of tetraspanin adaptor proteins below defined threshold values is associated with in vitro invasiveness of mammary carcinoma cells", Oncology Reports, 10:405-410 (2003).

Z. Si et al, "Expression of the neuroglandular antigen and analogues in melanoma, CD9 expression appears inversely related to metastatic potential of melanoma", Int. J. Cancer, 54:37-43 (1993).

L. Sikora et al, "Characterization of a novel neuroglandular antigen (NGA) expressed on abnormal human melanocytes", Int. J. Cancer, 39:138-145 (1987).

P. Sincock et al, "Localization of the transmembrane 4 superfamily (TM4SF) member PETA-3 (CD151) in normal human tissues: comparison with CD9, CD63, and alpha5beta1 integrin", J. Histochem Cytochem, 45:515-525 (1997).

K. Skubitz et al, "CD63 associates with CD11/CD18 in large detergent-resistant complexes after translocation to the cell surface in human neutrophils", FEBS Letters, 469:52-56 (2000).

K. Skubitz et al, "CD63 associates with lyrosine kinase activity and CD11/CD18, and transmits an activation signal in neutrophils", J. Immunol., 157:3617-3626 (1996).

P. Smith et al, "Anti-interleukin-6 monoclonal antibody induces regression of human prostate cancer xenografts in nude mice", The Prostate, 48:47-53 (2001).

R. Stephen et al, "A novel oestrogen-regulated gene in human breast cancer cells identified by differential display", J. Mol. Endocrin., 20:375-380 (1998).

V. Toothill et al, "Characterization of the enhanced adhesion of neutrophil leukocytes to thrombin-stimulated endothelial cells", J. Immunol., 145(1):283-291 (Jul. 1990).

P. Therasse et al, "New guidelines to evaluate the response to treatment in solid tumors", Journal of the National Cancer Institute, 92(3):205-216 (Feb. 2000).

B. Ulbricht et al, "Influence of 12(S)-hydroxyeicosatetraenoic acid (12(S)-HETE) on the localization of cathepsin B and cathepsin L in human lung tumor cells", Eur J Cell Biol, 74:294-301 (Nov. 1997).

C. Vennegoor et al, "Circulating melanoma-associated antigen detected by monoclonal antibody NKI/C-3", Cancer Immunol Immunother, 23:93-100 (1986).

V. Von Gruenigen et al, "Efficacy of intraperitoneal adenovirus-mediated p53 gene therapy in ovarian cancer", Int. J. Gynecol. Cancer, 9:365-372 (1999).

M. Wang et al, "An ocular melanoma-associated antigen", Arch Ophthalmol., 110:399-404 (1992).

W. Waud et al, "Characterization of in vivo mammary and prostate tumor xenograft models for growth and response to clinical anticancer agents", Contrib Oncol Basel Karger, 54:305-315 (1999).

Z. Xiao et al, "Generation of a baculovirus recombinant prostate-specific membrane antigen and its use in the development of a novel protein biochip quantitative immunoassay", Protein Expresion and Purification, 19:12-21 (2000).

R. Yauch et al, "Specific interactions among transmembrane 4 superfamily (TM4SF) proteins and phosphoinositide 4-kinase", Biochem. J., 351:629-637 (2000).

A. Zannettino et al, "A powerful new technique for isolating genes encoding cell surface antigens using retroviral expression cloning", J. Immunol., 156:611-620 (1996).

A. Zannettino et al, "Molecular cloning of the cell surface antigen identified by the osteoprogenitor-specific monoclonal antibody, HOP-26", J. Cell. Biochem., 89:56-66 (2003).

* cited by examiner

SEQUENCE LISTING

```
<160> NUMBER OF SEQ ID NOS: 5

<210> SEQ ID NO 1
<211> LENGTH: 30
<212> TYPE: DNA
<213> ORGANISM: Artificial
```

-continued

```
<220> FEATURE:
<223> OTHER INFORMATION: primer sequence used for PCR

<400> SEQUENCE: 1
gccgtgggat ccggggcaca gcttgtcctg                                    30

<210> SEQ ID NO 2
<211> LENGTH: 33
<212> TYPE: DNA
<213> ORGANISM: Artificial
<220> FEATURE:
<223> OTHER INFORMATION: primer sequence used for PCR

<400> SEQUENCE: 2
gatgacgaat tctcacagag agccaggggt agc                                33

<210> SEQ ID NO 3
<211> LENGTH: 27
<212> TYPE: DNA
<213> ORGANISM: Artificial
<220> FEATURE:
<223> OTHER INFORMATION: primer sequence used for PCR

<400> SEQUENCE: 3
ggctatggat ccagagataa ggtgatg                                       27

<210> SEQ ID NO 4
<211> LENGTH: 30
<212> TYPE: DNA
<213> ORGANISM: Artificial
<220> FEATURE:
<223> OTHER INFORMATION: primer sequence used for PCR

<400> SEQUENCE: 4
taccagaatt caatttttcc tcagccagcc                                    30

<210> SEQ ID NO 5
<211> LENGTH: 10
<212> TYPE: PRT
<213> ORGANISM: Homo sapiens

<400> SEQUENCE: 5

Val Met Ser Glu Phe Asn Asn Asn Phe Arg
1               5                   10
```

CYTOTOXICITY MEDIATION OF CELLS EVIDENCING SURFACE EXPRESSION OF CD63

REFERENCE TO RELATED APPLICATIONS

This application claims priority of U.S. Provisional Patent Application No. 60/642,057, filed Jan. 3, 2005 and is related to U.S. patent application Ser. No. 10/810,751, filed Mar. 26, 2004, U.S. patent application Ser. No. 10/603,006, filed Jun. 23, 2003, U.S. patent application Ser. No. 10/348,231, filed Jan. 21, 2003, now U.S. Pat. No. 7,009,040, issued Mar. 7, 2006 (including divisional application Ser. No. 10/891,866, filed Jul. 15, 2004, now U.S. Pat. No. 7,186,808, issued Mar. 6, 2007), the contents of each of which are herein incorporated by reference.

FIELD OF THE INVENTION

This invention relates to the diagnosis and treatment of cancerous diseases, particularly to the mediation of cytotoxicity of tumor cells; and most particularly to the use of cancerous disease modifying antibodies (CDMAB), optionally in combination with one or more chemotherapeutic agents, as a means for initiating the cytotoxic response. The invention further relates to binding assays, which utilize the CDMAB of the instant invention.

BACKGROUND OF THE INVENTION

CD63 in Cancer: CD63 is a Type III membrane protein of the tetraspanin family whose 20 current members are characterized by the presence of four transmembrane segments. Several groups independently identified CD63, using antibodies raised to whole cell preparations of activated platelets, granulocytes, and melanoma cells. Cloning of the respective cDNAs of their cognate glycoprotein antigens led to the recognition that the different antigens were one and the same molecule. The Sixth International Workshop on Leukocyte Typing (1996) subsequently categorized these antibodies as CD63 antibodies. Prior to the 1996 Workshop, CD63 was known by multiple names (melanoma 1 antigen, ocular melanoma-associated antigen, melanoma associated antigen ME491, lysosome-associated membrane glycoprotein 3, granulophysin, melanoma-associated antigen MLA1), which were sometimes related to the antibodies that led to its partial characterization and identification. Thus, CD63 was also designated as antigen ME491 (MAb ME491), neuroglandular antigen (MAbs LS59, LS62, LS76, LS113, LS140 and LS152), Pltgp40 (MAbs H5C6, H4F8 and H5D2), human bone marrow stromal cell antigen (MAb 12F12), osteoprogenitor-specific marker (MAb HOP-26), and integrin-associated protein (MAb 6H1). Other antibodies that were found to cross react with human CD63 were 8-1H, 8-2A (cross-reactivity with ME491), NKI/C-3 and NKI/black-13 (Vannegoor and Rumke, 1986; Demetrick et al., 1992; Wang et al., 1992).

CD63 was initially cloned from a melanoma cDNA library using MAb ME491, one of a number of antibodies raised against a preparation of human melanoma cells. It was shown that the reactivity of MAb ME491 appeared to be inversely correlated with melanoma progression in a study of human melanoma biopsies. The reactivity of the ME491 antibody was low in normal melanocytes, higher in the early stages of melanoma progression (dysplastic nevi and radial growth phase (RGP) tumors) and decreased or even absent in more advanced melanoma tumors such as those in the vertical growth phase (VGP) and in metastatic tumors.

CD63 was also found and partially characterized in human platelets using MAb 2.28 (raised against activated platelets) that detected an activation-dependent platelet membrane 53 kDa glycoprotein. This molecule was also associated with the membrane of internal granules in unstimulated platelets. In the same study MAb 2.28 also labelled internal granules in megakaryocytes and endothelial cells, where it co-localized with antibodies to the enzyme cathepsin D, a known marker of lysosomal compartments. Follow up studies with antibody clustering and expression cloning, led to the identification of the antigen recognized by this antibody as CD63, and further confirmed its presence in lysosomal compartments, where it co-localized with the compartment-specific markers LAMP-1 and LAMP-2. Cloning of this molecule identified it as CD63 and allowed its inclusion in the tetraspanin family.

Expression of CD63 was detected in many different tissues and cell types. At the cellular level it was found to be associated with the plasma membrane and also with intracellular late endosomal vesicular structures. Cell activation led, in certain cases, to increased surface expression by mobilization of intracellular stores of CD63. CD63 was also found to co-localize, and physically associate, with MHC class II in B-lymphocytes, particularly in endosomes, in exosomes involved in exporting MHC class II complexes to the surface, and in secreted vesicles. CD63 was found to interact with other members of the tetraspanin family, such as CD9, CD81, CD11 (integrin chain $\alpha_{M,L,X}$), CD18 (integrin chain $\beta_2$), CD49c (VLA-3 or integrin chain $\alpha_3$), CD49d (integrin chain $\alpha_4$), CD49f (VLA-6 or integrin chain ($\alpha$) and CD29 (integrin chain $\beta_1$), in a variety of cell types including B- and T-lymphocytes, neutrophils, breast cancer and melanoma cells.

The role of CD63 in cancer has been unclear. Although CD63 was initially discovered by several independent groups to be involved in diverse events such as platelet and granulocyte activation, MHC class II-dependent antigen presentation, integrin-dependent cell adhesion and motility, and tumor progression in certain types of cancers, its function has yet to be fully elucidated. Even though current evidence supports its role in a variety of cellular physiological events, it is not clear if these functions are independent of each other or if there is an underlying common cellular mechanism in which CD63 is involved.

Several groups have investigated the association between CD63 and the progression of certain types of tumors, particularly melanomas. A number of other anti-CD63 monoclonal antibodies, in addition to Mab ME491, were developed for immunohistochemical (IHC) staining of cancer samples obtained from patients with tumors at various stages of progression. It was observed that decreased staining, interpreted by the authors as most likely reflecting decreased expression of CD63, correlated with advanced progression and with metastatic characteristics of the tumors. A more recent study, also described a significant correlation between the apparent decreased expression levels (after quantitation of mRNA) of several members of the tetraspanin protein family, including CD63, and the in vitro invasiveness of several mammary carcinoma-derived cell lines. Another study identified CD63, by differential display, in cultured breast cancer cells subjected to estrogen deprivation. This indicated that CD63 expression can be steroid-hormone regulated and that altered CD63 abundance and/or function might also be associated with breast tumor progression.

By contrast, work with anti-CD63 monoclonal antibody MAb FC-5.01 revealed that its reactive epitope was variably expressed in different normal tissues. Although this antibody was found to recognize CD63, it did not distinguish between early and more advanced stage melanomas, including metastatic melanomas (unlike MAb ME491), which suggested that the CD63 antigen was present in these more advanced tumors, but that some of its epitopes may have been masked in the cells from tumors at different stages. This might have been due to altered post-translational modifications of the core CD63 polypeptide, or to the interaction of CD63 with other molecules, which might have affected the availability of specific epitopes for antibody recognition and binding. These results supported the observation, described by Si and Hersey (1993), that staining with the anti-CD63 MAb NKI-C3, did not distinguish between tissue sections from melanomas at different stages of progression, such as primary, radial growth phase, vertical growth phase, and metastatic melanomas. Although in other studies (Adachi et al., 1998; Huang et al., 1998) analysis of mRNA from breast, and from non-small-cell lung cancers, by quantitative PCR, revealed that for two tetraspanin family members (CD9 and CD82) there was a significant correlation between their expression levels and tumor progression and patient prognosis, no such correlation was found for CD63, in that its expression was similar in all the samples. As a result of these, apparently conflicting, results, there is lack of strong and consistent data that would definitively demonstrate the association of CD63 with cancer.

To date very few in vivo studies have attempted to establish a link between CD63 and an eventual tumor suppressor function of this molecule. In one of these studies, human CD63-overexpressing H-ras-transformed NIH-3T3 cells, injected both subcutaneously and intraperitoneally into athymic mice, revealed a decreased malignant/tumorigenic phenotype, as indicated by decreased tumor size and metastatic potential as well as by increased survival time, when compared to the behavior of the parental non-CD63-overexpressing cells. This suggested that the presence of human CD63 in the transformed cells might suppress their malignant behavior. More recently, work with a transgenic mouse model expressing human CD63, and developed to induce tolerance to CD63, indicated that tumor growth of an injected human CD63-MHC class I (H-2K$^b$) co-transfected murine melanoma cell line could be inhibited, and survival increased, upon immunization with human CD63 fused to vaccinia virus. It was suggested by the authors that the therapeutic effect was T-lymphocyte dependent, and that endogenous anti-CD63 antibodies did not appear to be involved in this protective effect, since tumor growth inhibition only occurred when animals were injected with the CD63-MHC class I co-transfected cells and not with the CD63-only transfected cell line. This interpretation was supported by the fact that in wild type animals, pre-immunized with purified human CD63 and shown to have developed anti-human CD63 antibodies, there was no protective effect against tumor cell growth. Work described by Radford et al. (1995) using the KM3 cell line, initially thought to be of human origin but later characterized as being of rat lineage, transfected with human CD63, suggested that expression of this protein decreased the growth and metastatic potential of these cells, relative to that observed using the parental non-transfected KM3 cells, when injected intradermally into athymic mice, although there was no significant difference between the in vitro growth rates of the various transfected and non-transfected cell lines. These observations distinguished the potential effect of CD63 from that of other tumor suppressor genes known to affect both the in vivo and the in vitro growth rates of tumor cells. Furthermore, addition of the anti-CD63 monoclonal antibody ME491, which was found to have a functional effect on the same cells by decreasing their random motility in an in vitro assay (Radford et al., 1997), did not impact their in vitro growth rates.

This study also described the observation that CD63 may promote migration in response to extracellular matrix (ECM)-derived chemoattractants, such as laminin, fibronectin, collagen and vitronectin, and that this effect may be mediated by the functional involvement of $\beta_1$-type integrins, although antibodies to the integrins were unable to block these effects. However, there appeared to be an antagonistic effect between the role of vitronectin-mediated signaling (a known ligand for the integrin $\alpha_v\beta_5$) and that of the signaling mediated by other ECM components such as fibronectin, laminin and collagen on CD63 transfected cells. This suggested that under specific conditions, in the presence of ECM components, expression of CD63 may lead to decreased migration, and that this may be dependent on a fine balance between adhesion and motility. In another study, an anti-CD63 monoclonal antibody (MAb 710F) enhanced the adhesion and spreading of PMA-treated HL-60 cells, while another anti-CD63 monoclonal antibody (MAb 2.28), promoted a similar effect, but only on a much smaller fraction of the cell population, and only when added in much larger amounts. These results showed that although many antibodies to CD63 have been developed, their functional effects can be quite different.

Tetraspanins may also be involved in cell proliferation. Oren et al. (1990) described anti-proliferative effects of the murine MAb 5A6, that recognizes CD81 (TAPA-1), on lymphoma cell lines. In another study, ligation of CD37 in human T-lymphocytes with antibodies blocked CD37-induced proliferation. More recently, a study with an animal model deficient in the expression of CD37 (CD37 knockout) revealed that T lymphocytes from this animal were hyperproliferative compared to those from wild type animals in response to concanavalin A activation and CD3/T cell receptor engagement. It was therefore proposed that a functional role in cell growth and proliferation might be a common feature of the tetraspanin family. Recent studies with hepatoblastoma and hepatocellular carcinoma cells revealed that engagement of these cells with anti-CD81 monoclonal antibodies led to activation of the Erk/MAP kinase pathway. This signaling pathway has been shown to be involved with cell growth and proliferation events. In parallel work, transfected cell lines overexpressing human CD81 displayed increased proliferation relative to the mock-transfected control cells. Therefore, available evidence has pointed to a role of the tetraspanins in general, and of CD63 in particular, in events associated with cell growth proliferation and with cell adhesion/motility. These two types of cellular events are currently the target of intense research as both play a central role in tumor progression and metastasis.

Until now, no anti-CD63 antibodies, or other reagents that specifically targeted CD63-expressing cells, were reported and shown to have a simultaneous impact on the in vitro and on the in vivo growth characteristics of tumor cells, and also on the survival time of animal models of tumor cell growth.

Amino acid sequence determination and analysis did not reveal homology between tetraspanins and other protein families, or with any previously characterized functional modules, nor has it suggested any previously known enzymatic activity. As a result it has been very difficult to investigate the role of this family of proteins in the modulation of signal transduction pathways. However, the evidence generated using tetraspanin-specific reagents that led to changes in cellular physiology, and which were intimately dependent on the modulation of signal transduction pathways, suggests that tetraspanins have signal transduction properties. CD63 was shown to associate, both physically and functionally, with a number of molecules that are themselves either enzymes involved in the generation of secondary messenger signals, or are associated physically and/or functionally with such enzymes.

Experiments designed to dissect the mechanism controlling the interaction of human neutrophils with endothelial cells, which is one of the initial steps of the inflammatory response, revealed that pre-treatment of neutrophils with several anti-CD63 monoclonal antibodies (AHN-16, AHN-16.1, AHN-16.2, AHN-16.3 and AHN-16-5) promoted their adhesion to cultured endothelial cell layers. Furthermore this effect was strongly dependent on the presence of calcium ion ($Ca^{2+}$), a well-known modulator of many intracellular signaling pathways and which was restricted to a specific period of time during which the cells were exposed to the stimulating antibodies. After longer exposure to the antibody, adhesion of the neutrophils to the endothelial cells became insensitive to the later addition of $Ca^{2+}$, therefore implicating a dynamic and temporally regulated (transitory) event. In addition, CD63 was found to physically interact with the CD11/CD18 protein complex, and reagents that specifically targeted this complex mediated a modulatory signal. In this study CD63 was also found to be physically associated with, or to be part of, a complex that included the enzyme tyrosine kinases Lck and Hck. These enzymes are members of a class of proteins that play a central role in mediating intracellular regulatory signals upon activation of specific surface receptors and are part of cascades of signaling pathways that result in cell-specific physiological changes. Another study suggested that co-ligation of tetraspanins (including CD63) with monoclonal antibodies could enhance the phosphorylation or activity of the enzyme focal adhesion kinase (FAK) that was induced by adhesion of MDA-MB-231 breast cancer cells to collagen substrate. This pointed to a direct involvement of CD63 (and of other tetraspanin family members) in the modulation of integrin-mediated tyrosine kinase signaling pathways. Other signaling pathways that may functionally intersect with the presence and ligation of surface CD63 by the anti-CD63 monoclonal antibody MAb 710F appear to be those dependent on modulation of phosphorylation by the enzyme protein kinase C (PKC), another well known modulator of intracellular signaling pathways. In this context, enhancement of adhesion and of morphological changes in the myeloid cell line HL-60 by MAb 710F was dependent on pre-treatment of the cells with phorbol myristate acetate (PMA) although the temporal involvement of PKC was not conclusively demonstrated. However, later work by an independent group demonstrated that PMA-induced HL-60 differentiation was PKC-activity dependent since the molecule Ro31-8220, a specific inhibitor of this enzyme, blocked the effect of PMA.

Further evidence supporting the association of CD63, and other tetraspanin family members, with signal transduction pathways, arose from work that described a physical association, either direct or as part of a supramolecular complex, between CD63 (and also CD53) molecules with tyrosine phosphatase activity. In this study, immunoprecipitate complexes isolated with anti-CD63 antibodies were shown to be associated with tyrosine phosphatase activity, although unlike for CD53, which was shown to associate with the tyrosine phosphatase CD45, it was not possible to identify the CD63-associated phosphatase. More recently several members of the tetraspanin family were also found to be associated with a type II phosphatidylinositol 4-kinase (type II PI 4-K) (Berditchevski et al., 1997). This interaction appeared to be very specific since it was only identified for CD9, CD63, CD81, CD151 and A15/TALLA, and it was not observed to occur with CD37, CD52, CD82, or NAG-2. In addition, the association between tetraspanin family members and PI-4K was mutually exclusive since each PI-4 kinase-containing complex was limited to a single tetraspanin family member. CD63-PI-4 kinase complexes, in particular, were found, almost entirely, in intracellular compartments in lipid raft-like domains, unlike those formed with the other tetraspanin members. This observation suggested that this CD63 fraction, found to interact with the PI-4 kinase, might have been involved in specific intracellular events (Claas, C, et al., 2001) related to, or dependent from, phosphoinositide biosynthesis pathways, which are well known for their involvement in the regulation of membrane trafficking (endocytosis and exocytosis) and of cytoskeleton reorganization, in addition to their function as secondary messenger molecules (Martin, T., 1998).

The direct and important involvement of all the enzymes, that CD63 was found until now to be directly associated with, in the regulation of signaling pathways provided further evidence in support of the association of CD63 with the modulation of signal transduction pathways, either as a regulator or as an effector molecule downstream from the activity of these enzymes.

Elucidation of the mechanisms that lead to tumor progression is a very difficult and complex endeavor frequently marked by apparently contradictory observations and, as a result, it rare that those observations successfully translate into effective therapies. In view of what is currently known about the association of CD63 with tumor progression and metastasis and with signal transduction mechanisms, it is possible that its function may be altered, in tumor cells.

Development of antigen-specific reagents with cytotoxic effects on tumor cells, that bind cells expressing the recognized antigen(s) and which by themselves, or associated with other molecules, have cellular and in vivo physiological activity such that these reagents inhibit tumor cell growth, progression and metastasis, without significant deleterious effects on normal cell populations, would be extremely beneficial as a potential therapeutic and or diagnostic tool.

Monoclonal *Antibodies as Cancer Therapy*: Each individual who presents with cancer is unique and has a cancer that is as different from other cancers as that person's identity. Despite this, the majority of current therapies treat all patients with the same type of cancer, at the same stage, in the same way. At least 30 percent of these patients will fail the first line therapy, thus leading to further rounds of treatment and the increased probability of treatment failure, metastases, and ultimately, death. A superior approach to treatment would be the customization of therapy for the particular individual. The only widely used therapy, which lends itself to customization, is surgery. Chemotherapy and radiation treatment cannot be tailored to the patient, and surgery by itself, in most cases, is inadequate for producing cures.

With the advent of monoclonal antibodies, the possibility of developing methods for customized therapy have become more realistic since each antibody can be directed to a single epitope. Furthermore, it is possible to produce a combination of antibodies that are directed to the constellation of epitopes that uniquely define a particular individual's tumor.

Having recognized that a significant difference between cancerous and normal cells is that cancerous cells contain antigens that are specific to transformed cells, the scientific community has long held that monoclonal antibodies can be, designed to specifically target transformed cells by binding specifically to these cancer antigens; thus giving rise to the belief that monoclonal antibodies can serve as "Magic Bullets" to eliminate cancer cells. However, it is now widely recognized that no single monoclonal antibody can serve in all instances of cancer, and that monoclonal antibodies can be deployed, as a class, as targeted cancer treatments. Monoclonal antibodies isolated in accordance with the teachings of the instantly disclosed invention have been shown to modify the cancerous disease process in a manner which is beneficial to the patient, for example by reducing the tumor burden, and will variously be referred to herein as cancerous disease modifying antibodies (CDMAB) or "anti-cancer" antibodies.

At the present time, the cancer patient usually has few options of treatment. The regimented approach to cancer therapy has produced improvements in global survival and morbidity rates. However, to the particular individual, these improved statistics do not necessarily correlate with an improvement in their personal situation.

Thus, if a methodology was put forth which enabled the practitioner to treat each tumor independently of other patients in the same cohort, this would permit the unique approach of tailoring therapy to just that one person. If such a course of therapy could increase the rate of cures, and produce better outcomes, it would satisfy a long-felt need.

Historically, the use of polyclonal antibodies has been used with limited success in the treatment of human cancers. Lymphomas and leukemias have been treated with human plasma, but there were few prolonged remissions or responses. Furthermore, there was a lack of reproducibility and no additional benefit compared to chemotherapy. Solid tumors such as breast cancers, melanomas and renal cell carcinomas have also been treated with human blood, chimpanzee serum, human plasma and horse serum with correspondingly unpredictable and ineffective results.

There have been many clinical trials of monoclonal antibodies for solid tumors. In the 1980s there were at least 4 clinical trials for human breast cancer that produced only 1 responder from at least 47 patients using antibodies against specific antigens or based on tissue selectivity. It was not until 1998 that there was a successful clinical trial using a humanized anti-Her2/neu antibody (Herceptin) in combination with Cisplatin. In this trial 37 patients were assessed for responses of which about a quarter had a partial response rate and an additional quarter had minor or stable disease progression. The median time to progression among the responders was 8.4 months with median response duration of 5.3 months.

Herceptin was approved in 1998 for first line use in combination with Taxol®. Clinical study results showed an increase in the median time to disease progression for those who received antibody therapy plus Taxol® (6.9 months) in comparison to the group that received Taxol® alone (3.0 months). There was also a slight increase in median survival; 22 versus 18 months for the Herceptin plus Taxol® treatment arm versus the Taxol® treatment alone arm. In addition, there was an increase in the number of both complete (8 versus 2 percent) and partial responders (34 versus 15 percent) in the antibody plus Taxol® combination group in comparison to Taxol® alone. However, treatment with Herceptin and Taxol® led to a higher incidence of cardiotoxicity in comparison to Taxol® treatment alone (13 versus 1 percent respectively). Also, Herceptin therapy was only effective for patients who over express (as determined through immunohistochemistry (IHC) analysis) the human epidermal growth factor receptor 2 (Her2/neu), a receptor, which currently has no known function or biologically important ligand; approximately 25 percent of patients who have metastatic breast cancer. Therefore, there is still a large unmet need for patients with breast cancer. Even those who can benefit from Herceptin treatment would still require chemotherapy and consequently would still have to deal with, at least to some degree, the side effects of this kind of treatment.

The clinical trials investigating colorectal cancer involve antibodies against both glycoprotein and glycolipid targets. Antibodies such as 17-1A, which has some specificity for adenocarcinomas, has undergone Phase 2 clinical trials in over 60 patients with only 1 patient having a partial response. In other trials, use of 17-1A produced only 1 complete response and 2 minor responses among 52 patients in protocols using additional cyclophosphamide. To date, Phase III clinical trials of 17-1A have not demonstrated improved efficacy as adjuvant therapy for stage III colon cancer. The use of a humanized murine monoclonal antibody initially approved for imaging also did not produce tumor regression.

Only recently have there been any positive results from colorectal cancer clinical studies with the use of monoclonal antibodies. In 2004, ERBITUX was approved for the second line treatment of patients with EGFR-expressing metastatic colorectal cancer who are refractory to irinotecan-based chemotherapy. Results from both a two-arm Phase II clinical study and a single arm study showed that ERBITUX in combination with irinotecan had a response rate of 23 and 15 percent respectively with a median time to disease progression of 4.1 and 6.5 months respectively. Results from the same two-arm Phase II clinical study and another single arm study showed that treatment with ERBITUX alone resulted in an 11 and 9 percent response rate respectively with a median time to disease progression of 1.5 and 4.2 months respectively.

Consequently in both Switzerland and the United States, ERBITUX treatment in combination with irinotecan, and in the United States, ERBITUX treatment alone, has been approved as a second line treatment of colon cancer patients who have failed first line irinotecan therapy. Therefore, like Herceptin, treatment in Switzerland is only approved as a combination of monoclonal antibody and chemotherapy. In addition, treatment in both Switzerland and the US is only approved for patients as a second line therapy. Also, in 2004, Avastin was approved for use in combination with intravenous 5-fluorouracil-based chemotherapy as a first line treatment of metastatic colorectal cancer. Phase III clinical study results demonstrated a prolongation in the median survival of patients treated with Avastin plus 5-fluorouracil compared to patients treated with 5-fluourouracil alone (20 months versus 16 months respectively). However, again like Herceptin and ERBITUX, treatment is only approved as a combination of monoclonal antibody and chemotherapy.

There also continues to be poor results for lung, brain, ovarian, pancreatic, prostate, and stomach cancer. The most promising recent results for non-small cell lung cancer came from a Phase II clinical trial where treatment involved a monoclonal antibody (SGN-15; dox-BR96, anti-Sialyl-LeX) conjugated to the cell-killing drug doxorubicin in combination with the chemotherapeutic agent Taxotere. Taxotere is the only FDA approved chemotherapy for the second line treatment of lung cancer. Initial data indicate an improved overall survival compared to Taxotere alone. Out of the 62 patients who were recruited for the study, two-thirds received SGN-15 in combination with Taxotere while the remaining one-third received Taxotere alone. For the patients receiving SGN-15 in combination with Taxotere, median overall survival was 7.3 months in comparison to 5.9 months for patients receiving Taxotere alone. Overall survival at 1 year and 18 months was 29 and 18 percent respectively for patients receiving SNG-15 plus Taxotere compared to 24 and 8 percent respectively for patients receiving Taxotere alone. Further clinical trials are planned.

Preclinically, there has been some limited success in the use of monoclonal antibodies for melanoma. Very few of these antibodies have reached clinical trials and to date none have been approved or demonstrated favorable results in Phase III clinical trials.

The discovery of new drugs to treat disease is hindered by the lack of identification of relevant targets, among the products of 30,000 known genes, that unambiguously contribute to disease pathogenesis. In oncology research, potential drug targets are often selected simply due to the fact that they are over-expressed in tumor cells. Targets thus identified are then screened for interaction with a multitude of compounds. In the case of potential antibody therapies, these candidate compounds are usually derived from traditional methods of monoclonal antibody generation according to the fundamental principles laid down by Kohler and Milstein (1975, Nature, 256, 495-497, Kohler and Milstein). Spleen cells are collected from mice immunized with antigen (e.g. whole cells, cell fractions, purified antigen) and fused with immortalized hybridoma partners. The resulting hybridomas are screened and selected for secretion of antibodies which bind most avidly to the target. Many therapeutic and diagnostic antibodies directed against cancer cells, including HERCEPTIN and RITUXIMAB, have been produced using these methods and selected on the basis of their affinity. The flaws in this strategy are twofold. Firstly, the choice of appropriate targets for therapeutic or diagnostic antibody binding is limited by the paucity of knowledge surrounding tissue specific carcinogenic processes and the resulting simplistic methods, such as selection by overexpression, by which these targets are identified. Secondly, the assumption that the drug molecule that binds to the receptor with the greatest affinity usually has the highest probability for initiating or inhibiting a signal, may not always be the case.

Despite some progress with the treatment of breast and colon cancer, the identification and development of efficacious antibody therapies, either as single agents or co-treatments, has been inadequate for all types of cancer.

Prior Patents:

U.S. Pat. No. 05,296,348 teaches methods for selecting monoclonal antibodies specific for cancer cell surface antigens that are internalizing, and for identifying monoclonal antibodies having anti-transcriptional and/or anti-replicational effects on cell metabolism. By way of example the ME491 antibody was shown to internalize in W9, WM35, WM983 melanoma cells, and SW948 colorectal carcinoma cells. In addition ME491 antibody was shown to decrease transcription and cell proliferation in SW948 cells. The patent application US20030211498A1 (and its related applications: WO0175177A3, WO0175177A2, AU0153140A5) allege a method of inhibiting the growth or metastasis of an ovarian tumor with an antibody that binds an ovarian tumor marker polypeptide encoded by an ovarian tumor marker gene selected from among a group that includes CD63 antigen. Serial analysis of gene expression using ovarian cancer was carried out to identify ovarian tumor marker genes which lead to the identification of CD63 as a candidate. The patent application WO02055551A1 (and its related application CNN364803A) alleges a new polypeptide-human CD63 antigen 56.87. The patent application CN1326962A alleges a new polypeptide-human CD63 antigen 14.63. The patent application CN1326951A alleges a new polypeptide-human CD63 antigen 15.07. The patent application CN1351054A alleges a new polypeptide-human CD63 antigen 11.11. These patents and patent applications identify CD63 antigens and antibodies but fail to disclose the isolated monoclonal antibody of the instant invention, or the utility of the isolated monoclonal antibody of the instant invention.

The gene encoding the ME491 polypeptide antigen was cloned and the sequence was received for publication on Feb. 24, 1988 (Can Res 48:2955, 1988, June 1); the gene encoding CD63 was cloned and the sequence published in February 1991 (JBC 266(5):3239-3245, 1991) and the publication clearly indicated the identity of ME491 with CD63.

WO2004041170.89 (Sequence ID No.: 89, priority filing date: 29 Jun. 2004), WO2003068268-A2 (Sequence ID No.: 1, priority filing date: 13 Feb. 2003 (2003WO-EP001461); other priority date: 14 Feb. 2002 (2002 GB-00003480)), WO2003057160-A29 (Sequence ID No.: 40, priority filing date: 30 Dec. 2002 (2002WO-US041798); other priority date: 2 Jan. 2002 (2002US-0345444P)) all allege polypeptides that have 100% sequence homology to CD63.

WO2003016475-A2 (Sequence ID No.: 9787&12101, priority filing date: 14 Aug. 2002 (2002WO-US025765); other priority date: 14 Aug. 2001 (2001US-0312147P) allege polypeptides that have 100% sequence homology with 237 amino acids of 238 amino acids comprising CD63.

WO2003070902-A2(Sequence ID No.:27, priority filing date: 18 Feb. 2003 (2003WO-US004902); other priority date: 20 Feb. 2002 (2002US-0358279P)) allege polypeptides that have 94% sequence homology with 224 amino acids of 238 amino acids comprising CD63.

EP1033401-A2 (Sequence ID No.: 4168&4913, priority filing date: 21 Feb. 2000 (2000EP-00200610); other priority date: 26 FEB-1999(99US-0122487P)) allege polypeptides that have 100% sequence homology with 205 amino acids and with 94 amino acids of 238 amino acids comprising CD63, respectively.

WO200257303-A2 (Human prey protein for *Shigella* ospG#26, priority filing date: 11 Jan. 2002 (2002WO-EP000777); other priority date: 12 Jan. 2001 (2001US-0261130P)) allege polypeptides that have 100% sequence homology with 130 amino acids of 238 amino acids comprising CD63.

WO200055180-A2 (Sequence ID No.: 756, priority filing date: 8 Mar. 2000 (2000WO-US005918); other priority date: 12 Mar. 1999(99US-0124270P)) allege polypeptides that have 99% sequence homology with 127 amino acids of 238 amino acids comprising CD63.

WO200200677-A1(Sequence ID No.:3203, priority filing date: 7 Jun. 2001 (2001WO-US018569); other priority date: 7 Jun. 2000 (2000US-0209467P)) allege polypeptides that have 97% sequence homology with 132 amino acids of 238 amino acids comprising CD63.

WO9966027-A1 (Large extracellular loop sequence from human CD63 protein, priority filing date: 15 Jun. 1999 (99WO-US013480); other priority date: 15 Jun. 1998 (98US-0089226P)) allege polypeptides that have 100% sequence homology with 99 amino acids of 238 amino acids comprising CD63.

WO200270539-A2 (Sequence ID No.: 1207, priority filing date: 5 Mar. 2002 (2002WO-US005095); other priority date: 5 Mar. 2001 (2001US-00799451)) allege polypeptides that have 86% sequence homology with 102 amino acids of 238 amino acids comprising CD63.

EP1033401-A2 (Sequence ID No.: 4169, 21 Feb. 2000 (2000EP-00200610); other priority date:26 Feb. 1999 (99US-0122487P)) allege polypeptides that have 100% sequence homology with 74 amino acids of 238 amino acids comprising CD63.

These patent applications identify polypetides that have varying sequence homology to CD63 antigen. In most cases these application also allege antibodies and antibody derivatives to the corresponding polypepide and their homologs but fail to disclose the isolated monoclonal antibody of the instant invention, or the utility of the isolated monoclonal antibody of the instant invention. Importantly, all the above applications were filed after the publication of the sequence of the polynucleotide encoding CD63.

SUMMARY OF THE INVENTION

The instant inventors have previously been awarded U.S. Pat. No. 6,180,357, entitled "Individualized Patient Specific Anti-Cancer Antibodies" directed to a process for selecting individually customized anti-cancer antibodies, which are useful in treating a cancerous disease. For the purpose of this document, the terms "antibody" and "monoclonal antibody" (mAb) may be used interchangeably and refer to intact immunoglobulins produced by hybridomas (e.g. murine or human), immunoconjugates and, as appropriate, immunoglobulin fragments and recombinant proteins derived from said immunoglobulins, such as chimeric and humanized immunoglobulins, F(ab') and F(ab')$_2$ fragments, single-chain antibodies, recombinant immunoglobulin variable regions (Fv)s, fusion proteins etc. It is well recognized in the art that some amino acid sequence can be varied in a polypeptide without significant effect on the structure or function of the protein. In the molecular rearrangement of antibodies, modifications in the nucleic or amino acid sequence of the backbone region can generally be tolerated. These include, but are not limited to, substitutions (preferred are conservative substitutions), deletions or additions. Furthermore, it is within the purview of this invention to conjugate standard chemotherapeutic modalities, e.g. radionuclides, with the CDMAB of the instant invention, thereby focusing the use of said chemotherapeutics. The CDMAB can also be conjugated to toxins, cytotoxic moieties, enzymes e.g. biotin conjugated enzymes, or hematogenous cells, thereby forming an antibody conjugate.

This application utilizes the method for producing patient specific anti-cancer antibodies as taught in the '357 patent for isolating hybridoma cell lines which encode for cancerous disease modifying monoclonal antibodies. These antibodies can be made specifically for one tumor and thus make possible the customization of cancer therapy. Within the context of this application, anti-cancer antibodies having either cell-killing (cytotoxic) or cell-growth inhibiting (cytostatic) properties will hereafter be referred to as cytotoxic. These antibodies can be used in aid of staging and diagnosis of a cancer, and can be used to treat tumor metastases. Unlike antibodies generated according to traditional drug discovery paradigms, antibodies generated in this way may target molecules and pathways not previously shown to be integral to the growth and/or survival of malignant tissue. Furthermore, the binding affinity of these antibodies are suited to requirements for initiation of the cytotoxic events that may not be amenable to stronger affinity interactions.

The prospect of individualized anti-cancer treatment will bring about a change in the way a patient is managed. A likely clinical scenario is that a tumor sample is obtained at the time of presentation, and banked. From this sample, the tumor can be typed from a panel of pre-existing cancerous disease modifying antibodies. The patient will be conventionally staged but the available antibodies can be of use in further staging the patient. The patient can be treated immediately with the existing antibodies and/or a panel of antibodies specific to the tumor can be produced either using the methods outlined herein or through the use of phage display libraries in conjunction with the screening methods herein disclosed. All the antibodies generated will be added to the library of anti-cancer antibodies since there is a possibility that other tumors can bear some of the same epitopes as the one that is being treated. The antibodies produced according to this method may be useful to treat cancerous disease in any number of patients who have cancers that bind to these antibodies.

Using substantially the process of U.S. Pat. No. 6,180,357, and as disclosed in U.S. Pat. No. 6,657,048 and in Ser. No. 10/348,231, Ser. No. 10/603,006 and Ser. No. 10/810,751, the contents of each of which are herein incorporated by reference, the mouse monoclonal antibodies, H460-22-1, 1A245.6 and 7BD-33-11A were obtained following immunization of mice with cells from a patient's lung (H460-22-1) or breast (7BD-33-11A and 1A245.6) tumor biopsy. The H460-22-1, 1A245.6 and 7BD-33-11A antigen was expressed on the cell surface of a wide range of human cell lines from different tissue origins. The breast cancer cell line MDA-MB-231 (MB-231) and the melanoma cell line A2058 were susceptible to the cytotoxic effect of H460-22-1 in vitro. The breast cancer cell line MCF-7 and prostate cancer cell line PC-3 were susceptible to the cytotoxic effects of 1A245.6 and 7BD-33-11A in vitro.

The result of H460-22-1 cytotoxicity against breast cancer cells in culture was further extended by its anti-tumor activity towards this cancer indication in vivo. In an in vivo model of breast cancer, the human MB-231 cells were implanted underneath the skin at the scruff of the neck of immunodeficient mice, as they are incapable of rejecting the human tumor cells due to a lack of certain immune cells. Pre-clinical xenograft tumor models are considered valid predictors of therapeutic efficacy. Xenografts in mice grow as solid tumors developing stroma, central necrosis and neo-vasculature. The mammary tumor cell line MB-231 has been evaluated as an in vivo xenograft model in immuno-deficient mice. The good engraftment or 'take-rate' of the MB-231 tumors and the sensitivity of the tumors to standard chemotherapeutic agents have characterized it as a suitable model. The parental cell line and variants of the cell line have been used in xenograft tumor models to evaluate a wide range of therapeutic agents.

In the preventative in vivo model of human breast cancer, H460-22-1 was given to mice one day prior to implantation of tumor cells followed by weekly injections for a period of 7 weeks. H460-22-1 treatment was significantly ($p<0.0001$) more effective in suppressing tumor growth during the treatment period than an isotype control antibody, which was identical to H460-22-1 in structure and size but incapable of binding MB-231 cells. At the end of the treatment phase, mice given H460-22-1 had tumors that grew to only 17.7 percent of the control group. During the post treatment follow-up period, the treatment effects of H460-22-1 were sustained and the mean tumor volume in the treated group continued to be significantly smaller than controls until the end of the measurement phase. Using survival as a measure of antibody efficacy, the control group reached 50 percent mortality between day 74-81 post-implantation. In contrast, the H460-22-1 treated group had not reached 50 percent mortality at the time of termination of the study. This difference was significant between H460-22-1 and isotype control treated group ($p<0.0015$). These data demonstrated that H460-22-1 treatment conferred a survival benefit compared to the control-treated group. H460-22-1 treatment appeared safe, as it did not induce any signs of toxicity, including reduced body weight and clinical distress. Thus, H460-22-1 treatment was efficacious as it both delayed tumor growth and enhanced survival compared to the control-treated group in a well-established model of human breast cancer. These results were also reproducible as similar findings were observed in another study of this kind and suggest its relevance and benefit to treatment of people with cancer.

Besides the preventative in vivo tumor model of breast cancer, H460-22-1 demonstrated anti-tumor activity against MB-231 cells in an established in vivo tumor model. In this xenograft tumor model, MB-231 breast cancer cells were transplanted subcutaneously into immunodeficient mice such that the tumor reached a critical size before antibody treatment. Treatment with H460-22-1 was compared to the standard chemotherapeutic drug, cisplatin, and it was shown that the cisplatin and H460-22-1 treatment groups had significantly (p<0.001) smaller mean tumor volumes compared with the group treated with isotype control antibody. H460-22-1 treatment mediated tumor suppression that was approximately two-thirds that of cisplatin chemotherapy but without the significant weight loss (p<0.003) and clinical distress observed with cisplatin. The anti-tumor activity of H460-22-1 and its minimal toxicity make it an attractive anti-cancer therapeutic agent.

In the post-treatment period, H460-22-1 maintained tumor suppression by delaying tumor growth compared to the isotype control antibody group. At 31 days post treatment, H460-22-1 limited tumor size by reducing tumor growth by 42 percent compared to the isotype control group, which is comparable to the 48 percent reduction observed at the end of the treatment. In the established tumor model of breast cancer, these results indicated the potential of H460-22-1 to maintain tumor suppression beyond the treatment phase and demonstrated the ability of the antibody to reduce the tumor burden and enhance survival in a mammal.

The result of 1A245.6 and 7BD-33-11A cytotoxicity against breast and prostate cancer cells in culture was further extended by its anti-tumor activity towards these cancer indications in vivo (as disclosed in Ser. No. 10/348,231, Ser. No. 10/891,866, Ser. No. 10/603,006 and Ser. No. 10/810,751, the contents of each of which are herein incorporated by reference). Pre-clinical xenograft tumor models are considered valid predictors of therapeutic efficacy.

As referenced in Ser. No. 10/348,231, Ser. No. 10/891,866, Ser. No. 10/603,006 and Ser. No. 10/810,751, the contents of each of which are herein incorporated by reference, 7BD-33-11A and 1A245.6 prevented tumor growth and tumor burden in a preventative in vivo model of human breast cancer. Monitoring continued past 300 days post-treatment. 7BD-33-11A never developed tumors and 87.5 percent of the 7BD-33-11A treatment group was still alive at over 9 months post-implantation. Conversely, the isotype control group had 100 percent mortality by day 72 (23 days post-treatment). 1A245.6 treated mice reached 100 percent mortality by day 151 post-treatment, which is greater than 6 times longer than the isotype control treatment group. Therefore 1A245.6, and to a greater extent 7BD-33-11A enhanced survival and prevented tumor growth (thus delaying disease progression) in a breast cancer model.

Also, as described in Ser. No. 10/348,231, Ser. No. 10/603,006, Ser. No. 10/810,751 and Ser. No. 10/891,866, the contents of each of which are herein incorporated by reference, 7BD-33-11A and 1A245.6 significantly suppressed tumor growth and decreased tumor burden in an established in vivo model of human breast cancer. By day 80 (23 days post-treatment), 7BD-33-11A treated mice had 83 percent lower mean tumor volumes in comparison to the isotype control group (p=0.001). 1A245.6 treatment reduced the mean tumor volumes on this day by 35 percent, however, the reduction did not reach significance in this experiment (p=0.135). Using survival as a measure of antibody efficacy, it was estimated that the risk of dying in the 7BD-33-11A treatment group was about 16 percent of the isotype control group (p=0.0006) at around 60 days post-treatment. 100 percent of the isotype control group died by 50 days post-treatment. In comparison, 1A245.6 treated mice survived until 100 days post-treatment and 60 percent of the 7BD-33-11A treatment groups were still alive at 130 days post-treatment. This data demonstrated that both 1A245.6 and 7BD-33-11A treatment conferred a survival benefit and reduced tumor burden compared to the control treated group. 7BD-33-11A and 1A245.6 treatment appeared safe, as it did not induce any signs of toxicity, including reduced body weight and clinical distress. Thus, 7BD-33-11A and 1A245.6 treatment was efficacious as it both delayed tumor growth and enhanced survival compared to the control-treated group in a well-established model of human breast cancer.

In a study outlined in Ser. No. 10/810,751, the contents of which are herein incorporated by reference, the effect of 7BD-33-11A compared to chemotherapeutic drug (Cisplatin) treatment alone or in combination was determined in two different established breast cancer xenograft models. In the MB-231 model, at day 83 (20 days after treatment), 7BD-33-11A treatment resulted in an 83 percent reduction in tumor growth relative to the buffer control treated animals (p=0.002). Cisplatin treatment alone resulted in a 77 percent reduction in tumor size relative to the control, while Cisplatin in combination with 7BD-33-11A resulted in an 88 percent reduction in tumor size relative to the control (p=0.006). In the MDA-MB-468 (MB-468) model, at day 62 (12 days after treatment) the greatest reduction in tumor growth (97 percent, p=0.001) was observed with Cisplatin treatment in combination with 7BD-33-11A. Cisplatin treatment alone produced a 95 percent decrease in tumor growth in comparison to the buffer control while 7BD-33-11A treatment alone showed a 37 percent (p=0.046) reduction. In both the MB-231 and MB-468 model, treatment with 7BD-33-11A led to greater animal well-being in comparison to treatment with Cisplatin as measured by body weight. These results indicated that 7BD-33-11A treatment had greater efficacy in comparison with Cisplatin treatment alone in the MB-231 model and was better tolerated with fewer adverse effects, such as weight loss, than Cisplatin in both breast cancer models.

To determine the effects of 7BD-33-11A treatment at various doses, a dose response experiment was performed in a preventative breast cancer xenograft model (as outlined and described in Ser. No. 10/810,751, the contents of which are herein incorporated by reference). At day 55 (5 days after treatment), the 0.2 mg/kg treatment group had prevented tumor growth by 85 percent relative to the isotype control treated group. Also at day 55, both the 2 and 20 mg/kg treatment groups had yet to develop tumors. Similar results were obtained past day 125 (75 days after treatment), where the 20 mg/kg treatment group had still not developed tumors and the 2 mg/kg treatment group had some initial tumor growth. 7BD-33-11A treatment also demonstrated a survival benefit. All of the mice in the isotype control group had died by day 104 (54 days after treatment) while the 0.2 mg/kg 7BD-33-11A treatment group survived until day 197 (147 days after treatment). Even greater survival benefits were observed with the 2.0 and 20 mg/kg 7BD-33-11A treatment groups; only 50 percent of the 2.0 mg/kg treatment group had died by day 290 (240 days after treatment) while none of the 20 mg/kg treatment group had died by also day 290. Therefore, 7BD-33-11A treatment showed significant tumor growth reduction and increased survival with all three doses with the greatest degree of efficacy being exhibited by the highest dose.

In addition to the beneficial effects in the established in vivo tumor model of breast cancer, 7BD-33-11A and 1A245.6 treatment also had anti-tumor activity against PC-3 cells in a preventative in vivo prostate cancer model (outlined in Ser. No. 10/603,006 and Ser. No. 10/810,751, the contents of each of which are herein incorporated by reference). 7BD-33-11A and 1A245.6 treatment was significantly (p=0.001 and 0.017 respectively) more effective in suppressing tumor growth shortly after the treatment period than an isotype control antibody. At the end of the treatment phase, mice given 7BD-33-11A or 1A245.6 had tumors that grew to only 31 and 50 percent of the isotype control group respectively.

For PC-3 SCID xenograft models, body weight can be used as a surrogate indicator of disease progression. On day 52, 7BD-33-11A and 1A245.6 treatment significantly (p=0.002 and 0.004 respectively) prevented the loss of body weight by 54 and 25 percent respectively in comparison to isotype control. Mice were monitored for survival post-treatment. At 11 days post-treatment, isotype and buffer control mice had reached 100 percent mortality. Conversely, 7BD-33-11A and 1A245.6 reached 100 percent mortality at day 38 post-treatment, 3 times longer than the control groups. Thus, 7BD-33-11A and 1A245.6 treatment was efficacious as it both delayed tumor growth, prevented body weight loss and extended survival compared to the isotype control treated group in a well-established model of human prostate cancer.

In addition to the preventative in vivo tumor model of prostate cancer, 7BD-33-11A demonstrated anti-tumor activity against PC-3 cells in an established in vivo tumor model (outlined in Ser. No. 10/603,006 and Ser. No. 10/810,751, the contents of each of which are herein incorporated by reference). Treatment with 7BD-33-11A was again compared to isotype control. It was shown that the 7BD-33-11A treatment group had significantly (p<0.024) smaller mean tumor volumes compared with the isotype control treated group immediately following treatment. 7BD-33-11A treatment mediated tumor suppression by 36 percent compared to the isotype control group.

In addition to the beneficial effects in the in vivo tumor models of breast and prostate cancer, 7BD-33-11A treatment also had anti-tumor activity against BxPC-3 cells in a preventative in vivo pancreatic cancer model. 7BD-33-11A treatment was significantly more effective in suppressing tumor growth (71 percent, p=0.0009) shortly after the treatment period than the buffer control. In addition, 7BD-33-11A treatment conferred a survival benefit in comparison to the buffer control treatment group. In the 7BD-33-11A treated group, 40 percent of the mice were still alive over 2 weeks after all of the buffer control group mice had died.

In addition to the beneficial effects in the in vivo tumor models of breast, prostate and pancreatic cancer, 7BD-33-11A treatment also had anti-tumor activity against A2058 and A375 cells in two separate preventative in vivo melanoma cancer models. In both the A2058 and A375 model, 7BD-33-11A treatment was significantly more effective in suppressing tumor growth (72 percent, p=0.011 and 63 percent, p=0.0006 respectively) than the buffer control. The anti-tumor activities of 7BD-33-11A in melanoma as well as in breast, prostate and pancreatic cancer models make it an attractive anti-cancer therapeutic agent.

To determine if the efficacy demonstrated by 7BD-33-11A in vivo is due in whole or in part to ADCC activity, 7BD-33-11A anti-tumor activity was measured against MB-231 cells in an established tumor model in both NOD SCID and SCID mice. NOD SCID mice are functionally deficit in natural killer (NK) cells and lack circulating complement and a functionally immature macrophage population while SCID mice have both complement and robust NK cell activity. 7BD-33-11A is a murine IgG2a monoclonal antibody and is therefore capable of ADCC activity in vivo. The anti-tumor activity of 7BD-33-11A was compared to both a buffer control and H460-22-1, a murine IgG1 monoclonal antibody that should not exhibit its activity through ADCC based on its isotype. On day 54 (4 days after the last treatment), in the SCID treated group, 7BD-33-11A and H460-22-1 treated mice developed tumors that were only 1.9 and 3.6 percent respectively of the mean tumor volume of the buffer control treated mice. Conversely, in the NOD SCID treated group, again on day 54 (4 days after the last treatment), 7BD-33-11A treated mice had tumor growth that was 67 percent of the mean tumor volume of the buffer control treated mice. H460-22-1 treated mice exhibited a similar effect as in the SCID mice; tumor growth was 1.4 percent of the mean tumor volume of the buffer control treated mice. Consequently, 7BD-33-11A activity in vivo seems to be in-part due to ADCC activity while H460-22-1's anti-tumor effect appears to be independent of ADCC.

In order to validate the H460-22-1, 1A245.6 and 7BD-33-11A epitope as a drug target, the expression of their target antigens in normal human tissues was determined. As partially discussed and outlined in Ser. No. 10/603,006 and Ser. No. 10/810,751, the contents of each of which are herein incorporated by reference, the binding of 7BD-33-11A, H460-22-1 and 1A245.6 towards normal human tissues was determined. By IHC staining, the majority of the tissues failed to express the 7BD-33-11A antigen, including the vital organs, such as the kidney, heart, and lung. 7BD-33-11A stained the salivary gland, liver, pancreas, stomach, prostate and duodendum, and strongly stained the tonsil. Results from tissue staining indicated that 7BD-33-11A showed restricted binding to various cell types but had binding to infiltrating macrophages, lymphocytes, and fibroblasts. For both H460-22-1 and 1A245.6, a wider range of tissues was positively stained. For the majority of cases, staining was restricted to the epithelium or infiltrating macrophages, lymphocytes, and fibroblasts. However, positive staining was seen on both cardiac muscle and hepatocytes. 7BD-33-11A, H460-22-1 and 1A245.6 displayed both membrane and cytoplasmic staining patterns.

As discussed and outlined in Ser. No. 10/810,751, the contents of which are herein incorporated by reference, 7BD-33-11A was compared with commercially available anti-CD63 antibodies (RFAC4 and H5C6). Results from normal human tissue staining indicated that 7BD-33-11A again showed restricted binding to various cell types but had binding to infiltrating macrophages, lymphocytes, and fibroblasts. The RFAC4 and H5C6 antibodies showed a similar staining pattern in comparison to each other. However, the staining pattern of both RFAC4 and H5C6 was quite different than that observed with 7BD-33-11A. Specifically, both RFAC4 and H5C6 antibodies bound to a broader range of normal tissues, usually had higher staining intensity in tissues where 7BD-33-11A was also positive and bound not only to infiltrating macrophages, lymphocytes and fibroblasts but also to the epithelium in a majority of the tissues.

Localization of the H460-22-1, 1A245.6 and 7BD-33-11A antigen and determination of their prevalence within the population, such as among breast cancer patients, is important in assessing the therapeutic use of these antibodies and designing effective clinical trials. To address H460-22-1, 1A245.6 and 7BD-33-11A antigen expression in breast tumors from cancer patients, tumor tissue samples from 98 individual breast cancer patients were screened for expression of the 7BD-33-11A antigen (results from 50 patients have been previously described in Ser. No. 10/603,006 and Ser. No. 10/810,751, the contents of each of which are herein incorporated by reference) and tumor tissue samples from 50 patients were screened for 1A245.6 (discussed in Ser. No.

10/603,006, the contents of which are herein incorporated by reference) and H460-22-1 antigen.

The results of these studies showed that 37 percent of tissue samples positively stained for the 7BD-33-11A antigen. Expression of 7BD-33-11A within patient samples appeared specific for cancer cells as staining was restricted to malignant cells. In addition, 7BD-33-11A stained 0 of 20 samples of normal tissue from breast cancer patients. On the other hand, H460-22-1 and 1A245.6 stained 92 percent and 98 percent of breast cancer tissue samples respectively. H460-22-1 and 1A245.6 also stained 9 out of 10 samples of normal tissue from breast cancer patients. However, this staining was generally much weaker than that observed with the breast cancer tissue samples and was generally restricted to infiltrating fibroblasts. Breast tumor expression of the 7BD-33-11A, H460-22-1 and 1A245.6 antigen appeared to be localized to the cell membrane and cytoplasm of malignant cells, making CD63 an attractive target for therapy.

As discussed and outlined in Ser. No. 10/810,751, the contents of which are herein incorporated by reference, 7BD-33-11A was compared to RFAC4 and H5C6 and to an anti-Her2 antibody (c-erbB-2). The results of the current study were similar to previous results and showed that 36 percent of tumor tissue samples stained positive for the 7BD-33-11A antigen while 94 and 85 percent of breast tumor tissues were positive for the H5C6 and RFAC4 epitope respectively. Expression of 7BD-33-11A within patient samples appeared specific for cancer cells as staining was restricted to malignant cells. In addition, 7BD-33-11A stained 0 of 10 samples of normal tissue from breast cancer patients while both H5C6 and RFAC4 stained 7 of 8 samples of normal breast tissue. In comparison to c-erbB-2, 7BD-33-11A showed a completely different staining profile where half of the breast tumor tissue samples that were positive for the 7BD-33-11A antigen were negative for Her2 expression indicating that 7BD-33-11A targets a patient population that is not served by existing antibody therapies. There were also differences in the intensity of staining between the breast tumor tissue sections that were positive for both 7BD-33-11A and Her2. The c-erbB-2 antibody also positively stained one of the normal breast tissue sections.

As partially discussed in Ser. No. 10/603,006 and Ser. No. 10/810,751, the contents of each of which are herein incorporated by reference, 7BD-33-11A, H460-22-1 and 1A245.6 expression was further evaluated based on breast tumor expression of the receptors for the hormones estrogen and progesterone, which play an important role in the development, treatment, and prognosis of breast tumors. No correlation was apparent between expression of the 1A245.6 antigen and expression of the receptors for either estrogen or progesterone. There was a slight correlation between absence of estrogen receptors and presence of progesterone receptors and 7BD33-11A antigen expression and presence of both estrogen and progesterone receptors and H460-22-1 antigen expression. When tumors were analyzed based on their stage, or degree to which the cancer advanced, results suggested a trend towards greater positive expression with higher tumor stage for both 7BD-33-11A and H460-22-1. Similar results were obtained with RFAC4. H5C6 also showed a very slight correlation with estrogen or progesterone receptor expression but there was no apparent correlation with tumor stage, however, conclusions were limited by the small sample size.

Localization of the 7BD-33-11A antigen and its prevalence within prostate cancer patients is important in assessing the benefits of 7BD-33-11A immunotherapy to patients with prostate cancer and designing effective clinical trials. To address 7BD-33-11A antigen expression in prostate tumors from cancer patients, tumor tissue samples from 51 individual prostate cancer patients were screened for expression of the 7BD-33-11A antigen (as outlined and discussed in Ser. No. 10/810,751, the contents of each of which are herein incorporated by reference). The results of the study showed that 88 percent of tissue samples stained positive for the 7BD-33-11A antigen. Although 7BD-33-11A stained the normal tissue sections with high intensity as well, there was a higher degree of membranous staining in the tumor tissue samples in comparison to the normal samples. There was one embryonal rhabdomyosarcroma tissue sample that did not stain for the 7BD-33-11A antigen. In the small sample size tested there did not appear to be a direct correlation between tumor stage and presence of the 7BD-33-11A antigen.

Localization of the 7BD-33-11A antigen and its prevalence within melanoma cancer patients is important in assessing the benefits of 7BD-33-11A immunotherapy to patients with melanoma and designing effective clinical trials. To address 7BD-33-11A antigen expression in melanoma tumors from cancer patients, tumor tissue samples from 39 individual melanoma patients were screened for expression of the 7BD-33-11A antigen. The results of the study showed that 90 percent of tissue samples stained positive for the 7BD-33-11A antigen. In this small sample, there also appeared to be no direct correlation between tumor stage and presence of the 7BD-33-11A antigen.

To further extend the potential therapeutic benefit of 7BD-33-11A, H460-22-1 and 1A245.6, the frequency and localization of the antigen within various human cancer tissues was also determined (outlined in Ser. No. 10/603,006 for 1A245.6 and 7BD33-11A and referenced in Ser. No. 10/810,751, the contents of each of which are herein incorporated by reference). Several cancer types, in addition to breast and prostate cancer, expressed the 7BD-33-11A antigen. The positive human cancer types included skin (1/2), lung (3/4), liver (2/3), stomach (4/5), thyroid (2/2), uterus (4/4) and kidney (3/3). Some cancers did not express the antigen; these included ovary (0/3), testis (0/1), brain (0/2) and lymph node (0/2). For H460-22-1 and 1A245.6, as with the normal human tissue array, a multitude of cancers from various human tissue types were positively stained. Greater staining was seen on malignant cells of the skin, lung, liver, uterus, kidney, stomach and bladder. As with human breast, prostate and melanoma cancer tissue, localization of 7BD-33-11A, H460-22-1 and 1A245.6 occurred both on the membrane and within the cytoplasm of these tumor cells. Therefore, in addition to the H460-22-1, 1A245.6 and 7BD-33-11A antibody binding to cancer cell lines in vitro, there is evidence that the antigen is expressed in humans, and on multiple types of cancers.

As outlined in Ser. No. 10/810,751, the contents of which are herein incorporated by reference, for 7BD-33-11A and herein for 1A245.6 and H460-22-1, biochemical data also indicate that the antigen recognized by H460-22-1, 1A245.6 and 7BD-33-11A is CD63. This is supported by studies showing that the monoclonal antibody RFAC4, reactive against CD63, identifies proteins that bound to 7BD-33-11A, H460-22-1 or 1A245.6 by immunoprecipitation. In addition, bacterial expression studies elucidated that H460-22-1, 1A245.6 and 7BD-33-11A bound to extracellular loop 2 of CD63. The 7BD-33-11A, H460-22-1 and 1A245.6 epitope was also distinguished by being conformation dependent. These IHC and biochemical results demonstrate that H460-22-1, 1A245.6 and 7BD-33-11A bind to the CD63 antigen. Thus, the preponderance of evidence shows that H460-22-1, 1A245.6 and 7BD-33-11A mediate anti-cancer effects through ligation of unique conformational epitope(s) present on CD63. For the purpose of this invention, said epitope is defined as a "CD63 antigenic moiety" characterized by its ability to bind with a monoclonal antibody encoded by the hybridoma cell line 7BD-33-11A, 1A245.6, H460-22-1, antigenic binding fragments thereof or antibody conjugates thereof.

In toto, this data demonstrates that the H460-22-1, 1A245.6 and 7BD-33-11A antigen is a cancer associated antigen and is expressed in humans, and is a pathologically relevant cancer target. Further, this data also demonstrates the binding of the H460-22-1, 1A245.6 and 7BD-33-11A antibody to human cancer tissues, and can be used appropriately for assays that can be diagnostic, predictive of therapy, or prognostic. In addition, the cell membrane localization of this antigen is indicative of the cancer status of the cell due to the relative infrequency of expression of the antigen in most non-malignant cells, and this observation permits the use of this antigen, its gene or derivatives, its protein or its variants to be used for assays that can be diagnostic, predictive of therapy, or prognostic.

The present invention describes the development and use of H460-22-1, 7BD-33-11A and 1A245.6, developed by the process described in patent U.S. Pat. No. 6,180,357 and identified by, its effect, in a cytotoxic assay, in non-established and established tumor growth in animal models and in prolonging survival time in those suffering from cancerous disease. This invention represents an advance in the field of cancer treatment in that it describes, for the first time, reagents that bind specifically to an epitope or epitopes present on the target molecule, CD63, and that also have in vitro cytotoxic properties against malignant tumor cells but not normal cells, and which also directly mediate inhibition of tumor growth and extension of survival in in vivo models of human cancer. This is an advance in relation to any other previously described anti-CD63 antibody, since none have been shown to have similar properties. It also provides an advance in the field since it clearly demonstrates, and for the first time, the direct involvement of CD63 in events associated with growth and development of certain types of tumors. It also represents an advance in cancer therapy since it has the potential to display similar anti-cancer properties in human patients. A further advance is that inclusion of these antibodies in a library of anti-cancer antibodies will enhance the possibility of targeting tumors expressing different antigen markers by determination of the appropriate combination of different anti-cancer antibodies, to find the most effective in targeting and inhibiting growth and development of the tumors.

In all, this invention teaches the use of the 7BD-33-11A antigen as a target for a therapeutic agent, that when administered can reduce the tumor burden of a cancer expressing the antigen in a mammal, and can also lead to a prolonged survival of the treated mammal. This invention also teaches the use of CDMABs (H460-22-1, 7BD-33-11A and 1A245.6), and their derivatives, and antigen binding fragments thereof, to target their antigen to reduce the tumor burden of a cancer expressing the antigen in a mammal, and to prolong the survival of a mammal bearing tumors that express this antigen. Furthermore, this invention also teaches the use of detecting the H460-22-1, 7BD-33-11A and 1A245.6 antigen in cancerous cells that can be useful for the diagnosis, prediction of therapy, and prognosis of mammals bearing tumors that express this antigen.

If a patient is refractory to the initial course of therapy or metastases develop, the process of generating specific antibodies to the tumor can be repeated for re-treatment. Furthermore, the anti-cancer antibodies can be conjugated to red blood cells obtained from that patient, or a compatible donor, and re-infused for treatment of metastases. There have been few effective treatments for metastatic cancer and metastases usually portend a poor outcome resulting in death. However, metastatic cancers are usually well vascularized and the delivery of anti-cancer antibodies by red blood cells can have the effect of concentrating the antibodies at the site of the tumor. Even prior to metastases, most cancer cells are dependent on the host's blood supply for their survival and anti-cancer antibodies conjugated to red blood cells can be effective against in situ tumors as well. Alternatively, the antibodies may be conjugated to other hematogenous cells, e.g. lymphocytes, macrophages, monocytes, natural killer cells, etc.

There are five classes of antibodies and each is associated with a function that is conferred by its heavy chain. It is generally thought that cancer cell killing by naked antibodies are mediated either through antibody-dependent cell-mediated cytotoxicity (ADCC) or complement-dependent cytotoxicity (CDC). For example murine IgM and IgG2a antibodies can activate human complement by binding the C-1 component of the complement system thereby activating the classical pathway of complement activation which can lead to tumor lysis. For human antibodies, the most effective complement-activating antibodies are generally IgM and IgG1. Murine antibodies of the IgG2a and IgG3 isotype are effective at recruiting cytotoxic cells that have Fc receptors which will lead to cell killing by monocytes, macrophages, granulocytes and certain lymphocytes. Human antibodies of both the IgG1 and IgG3 isotype mediate ADCC.

Another possible mechanism of antibody-mediated cancer killing may be through the use of antibodies that function to catalyze the hydrolysis of various chemical bonds in the cell membrane and its associated glycoproteins or glycolipids, so-called catalytic antibodies.

There are two additional mechanisms of antibody-mediated cancer cell killing, which are more widely accepted. The first is the use of antibodies as a vaccine to induce the body to produce an immune response against the putative antigen that resides on the cancer cell. The second is the use of antibodies to target growth receptors and interfere with their function or to down regulate that receptor so that its function is effectively lost.

The clinical utility of a cancer drug is based on the benefit of the drug under an acceptable risk profile to the patient. In cancer therapy survival has generally been the most sought after benefit, however there are a number of other well-recognized benefits in addition to prolonging life. These other benefits, where treatment does not adversely affect survival, include symptom palliation, protection against adverse events, prolongation in time to recurrence or disease-free survival, and prolongation in time to progression. These criteria are generally accepted and regulatory bodies such as the U.S. Food and Drug Administration (F.D.A.) approve drugs that produce these benefits (Hirschfeld et al. Critical Reviews in Oncology/Hematolgy 42:137-143 2002). In addition to these criteria it is well recognized that there are other endpoints that may presage these types of benefits. In part, the accelerated approval process granted by the U.S. F.D.A. acknowledges that there are surrogates that will likely predict patient benefit. As of year-end (2003), there have been sixteen drugs approved under this process, and of these, four have gone on to full approval, i.e., follow-up studies have demonstrated direct patient benefit as predicted by surrogate endpoints. One important endpoint for determining drug effects in solid tumors is the assessment of tumor burden by measuring response to treatment (Therasse et al. Journal of the National Cancer Institute 92(3):205-216 2000). The clinical criteria (RECIST criteria) for such evaluation have been promulgated by Response Evaluation Criteria in Solid Tumors Working Group, a group of international experts in cancer. Drugs with a demonstrated effect on tumor burden, as shown by objective responses according to RECIST criteria, in comparison to the appropriate control group tend to, ultimately, produce direct patient benefit. In the pre-clinical setting tumor burden is generally more straightforward to assess and document. In that pre-clinical studies can be translated to the clinical setting, drugs that produce prolonged survival in pre-clinical models have the greatest anticipated clinical utility. Analogous to producing positive responses to clinical treatment, drugs that reduce tumor burden in the pre-clinical setting may also have significant direct impact on the disease. Although prolongation of survival is the most sought after clinical outcome from cancer drug treatment, there are other benefits that have clinical utility and it is clear that tumor burden reduction, which may correlate to a delay in disease progression, extended survival or both, can also lead to direct benefits and have clinical impact (Eckhardt et al. Developmental Therapeutics: Successes and Failures of Clinical Trial Designs of Targeted Compounds; ASCO Educational Book, $39^{th}$ Annual Meeting, 2003, pages 209-219).

Accordingly, it is an objective of the invention to utilize a method for producing cancerous disease modifying antibodies from cells derived from a particular individual which are cytotoxic with respect to cancer cells while simultaneously being relatively non-toxic to non-cancerous cells, in order to isolate hybridoma cell lines and the corresponding isolated monoclonal antibodies and antigen binding fragments thereof for which said hybridoma cell lines are encoded.

It is an additional objective of the invention to teach CDMAB and antigen binding fragments thereof.

It is a further objective of the instant invention to produce CDMAB whose cytotoxicity is mediated through ADCC.

It is yet an additional objective of the instant invention to produce CDMAB whose cytotoxicity is mediated through CDC.

It is still a further objective of the instant invention to produce CDMAB whose cytotoxicity is a function of their ability to catalyze hydrolysis of cellular chemical bonds.

A still further objective of the instant invention is to produce CDMAB which are useful in a binding assay for diagnosis, prognosis, and monitoring of cancer.

Other objects and advantages of this invention will become apparent from the following description wherein, by way of illustration and example, certain embodiments of this invention are set forth.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

EXAMPLE 1

Figure 1:
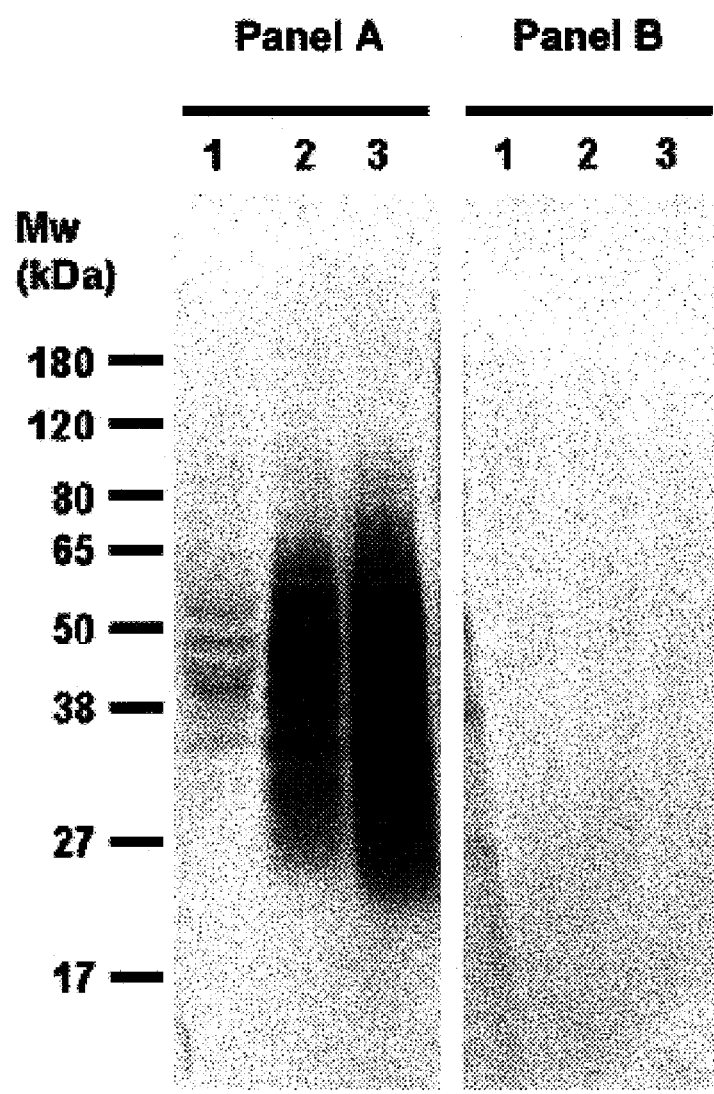
FIG. 1. Western blot of MDA-MB-231 whole cell lysates (Lane 1) or membranes (Lanes 2 and 3) probed with 7BD-33-11A (Panel A) or isotype control (Panel B). Molecular weight markers are indicated on the left.

Identification of 7BD-33-11A Binding proteins by Western Immunoblotting

As outlined and discussed in Ser. No. 10/810,751, the contents of are herein incorporated by reference, to identify the antigen(s) recognized by the antibody 7BD-33-11A, cell membrane preparations were subjected to sodium dodecyl-sulphate polyacrylamide gel electrophoresis (SDS-PAGE), and transferred to membranes. The latter were probed with the antibody 7BD-33-11A to visualize the proteins detected by this antibody.

1.0. Whole Cell Lysate and Total Membrane Fraction Preparation 1.1. Whole Cell Lysate Preparation Previous work by FACS demonstrated binding of antibody 7BD-33-11A to the breast cancer cell line MDA-MB-231 (MB-231). As a result total cell membrane preparations and whole cell lysates obtained from this cell line were used for the antigen identification and characterization. Total cell lysate from MB-231 cells was prepared as follows: MB-231 cell pellet (1.5 g) was resuspended in 2 mL lysis buffer containing 20 mM Tris, pH 7.4, 150 mM NaCl, 1% (v/v) Triton X-100, 0.02% (w/v) sodium azide, 2 mM sodium orthovanadate, 50 mM sodium fluoride, and a protease inhibitor cocktail (Roche Diagnostics; Manheim, Germany). The pellet was homogenized with a glass homogenizer and was incubated with stirring, for 1 hr at 4° C. Samples were then subjected to centrifugation (20,000 g) for 15 min at 4° C., to remove detergent insoluble material. Supernatants were collected, divided in aliquots, and frozen at −80° C. The protein concentration in the cell lysate was determined by the BCA (bicinchoninic acid) assay (Pierce; Rockford, Ill.).

1.2. Total Cell Membrane Fraction Preparation

Total cell membranes were prepared from confluent cultures of MB-231 breast cancer cells. Media was removed from cell stacks and the cells were washed with phosphate buffered saline (PBS). Cells were dissociated with dissociation buffer (Gibco-BRL; Grand Island, N.Y.) for 20 min at 37° C. on a platform shaker. Cells were collected and centrifuged at 900 g for 10 min at 4° C. After centrifugation, cell pellets were washed by resuspending in PBS and centrifuging again at 900 g for 10 min at 4° C. Pellets were then stored at −80° C. until required. To prepare membranes, cell pellets were thawed and resuspended in homogenization buffer containing 1 tablet per 50 mL of complete protease inhibitor cocktail (Roche; Laval QC) at a ratio of 3 mL buffer per gram of cells. The cell suspension was subjected to homogenization using a polytron homogenizer on ice in order to lyse the cells. The cell homogenate was centrifuged at 15,000 g for 10 min at 4° C. to remove the nuclear particulate. Supernatant was harvested, divided into tubes and then centrifuged at 75,600 g for 90 min at 4° C. Supernatant was carefully removed and each membrane pellet was resuspended in approximately 5 mL of homogenization buffer. The membrane pellets from all tubes were combined, divided one more time, and centrifuged at 75,600 g for 90 min at 4° C. Supernatant was carefully removed and the pellets were weighed. Solubilization buffer containing 1% Triton X-100 was added to the pellets at a ratio of 3 mL buffer per gram of membrane pellet. Membranes were solubilized by shaking on a platform shaker at 300 rpm, for 1 hr on ice. The membrane suspension was centrifuged at 75,600 g to pellet insoluble material. The supernatant, containing the solubilized membrane proteins, was carefully removed from the tubes, assayed for protein concentration, and stored at −80° C.

2.0 1-Dimensional SDS-PAGE and Western Immunoblotting

Figure 2:
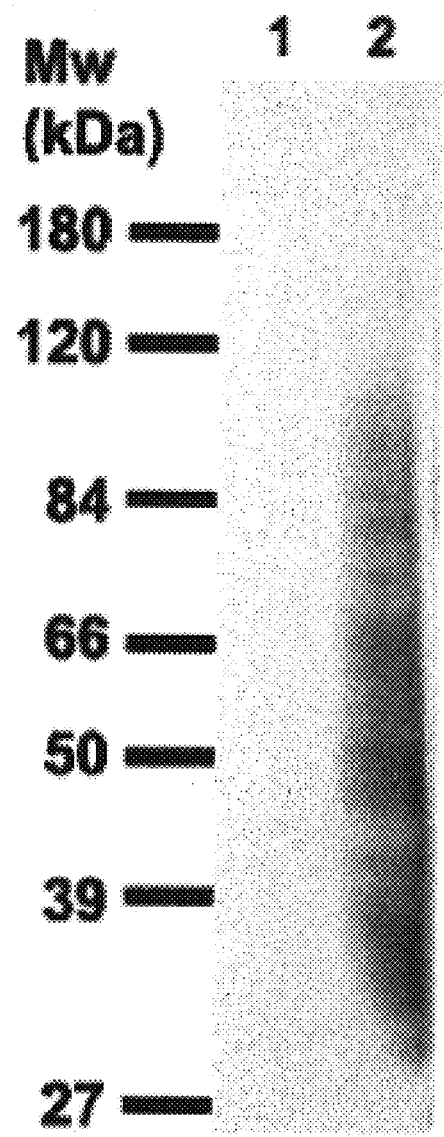
FIG. 2. Western blot of MDA-MB-231 membranes probed with 7BD-33-11A. Lane 1: Membrane run under reducing conditions. Lane 2: Membranes run under non-reducing conditions. Molecular weight markers are indicated on the left.

Proteins from the total membrane fraction and whole cell lysate of MB-231 cells were separated by 1-dimensional SDS-PAGE (ID SDS-PAGE), on a 5 and 10 percent stacking and separating gel, respectively. Proteins were transferred overnight, at 4° C., by electroblotting onto PVDF membranes (Millipore; Billerica, Mass.). Complete transfer was determined by assessing the transfer of prestained molecular weight markers onto the membrane. After transfer, the membranes were blocked with 5 percent (w/v) skim milk in TBST, for 1 hr at room temperature (RT), and two replicate blots were then probed as follows: one blot was probed with the antibody 7BD-33-11A (5 μg/mL, in 5 percent skim milk in TBST) and the replicate blot was probed with an $IgG_{2a}$ isotype control (5 μg/mL, in 5 percent skim milk in TBST). Blots were washed 3 times for 10 min in TBST and then incubated with horseradish HRP-conjugated goat anti-mouse IgG (Fc) (Bio-Rad Laboratories; Hercules, Calif.), for 1 hr at RT. After washing 3 times for 10 min each with TBST, the blots were developed with the TMB peroxidase substrate kit (Vector Laboratories; Burlingame, Calif.) following the manufacturers' instructions. The blots were rinsed with water and images were acquired with a gel documentation system (FIGS. 1 and 2) (Bio-Rad; Hercules, Calif.). Blots were imaged under the same conditions of camera focus, aperture and image acquisition time. In FIG. 1, 7BD-33-11A clearly bound to proteins in the 20-80 kDa range, and its reactivity was detected in the lanes containing whole cell lysate and total membrane fraction. The isotype control did not bind to any proteins in the MB-231 lysate or membrane fractions, indicating that the binding for 7BD-33-11A was specific. FIG. 2 demonstrated the effect of sample reduction on 7BD-33-11A binding, on a Western blot. Reactivity of this antibody was only detected when the samples were prepared under non-reducing conditions (Lane 2). Reducing agents such as DTT or β-mercaptoethanol completely eliminated binding (Lane 1), indicating that recognition and binding of 7BD-33-11A to its epitope on the native protein depended on the presence of disulfide bonds.

Figure 3:
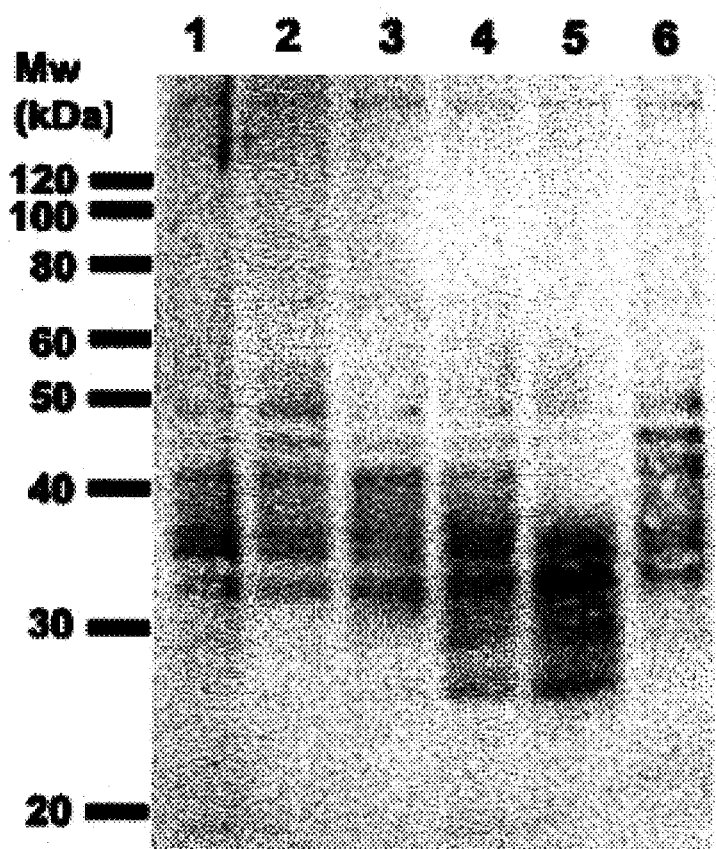
FIG. 3. Effect of deglycosylation on the binding of 7BD-33-11A to MDA-MB-231 membranes. MDA-MB-231 membranes were subjected to treatment with glycopeptidase F (PNGase F; Lane 1), O-glycanase (Lane 2), sialidase (Lane 3), the combination of PNGase F, O-glycanase and sialidase (Lane 4), the combination of PNGase F, O-glycanase, sialidase, galactosidase and glucosaminidase (Lane 5) or buffer control (Lane 6). Molecular weight markers are indicated on the left.

To determine if the disperse nature of the antigen, as detected by Western immunoblotting, was due to heterogeneous glycosylation, total membrane fractions were subjected to treatment with several glycosidases (glycopeptidase F, o-glycanase, sialidase, galactosidase and glucosaminidase) which removed specific carbohydrate groups. After treatment the samples were subjected to 1D SDS-PAGE and Western blotting. It was expected that if some of the enzymes removed a portion of carbohydrate that accounted for a significant amount of the mass of the antigen(s) recognized by the antibody 7BD-33-11A, that it would be possible to detect that difference by SDS-PAGE. FIG. 3 shows that glycosidase treatment of total membrane fractions from MB-231 cells resulted in a significant decrease in the mass of the recognized antigen(s). This indicated that the antigen recognized by the 7BD-33-11A antibody was comprised of at least one glycoprotein. The fact that a significant shift in the mobility of the antigen(s) only occurred when several enzymes were used together indicated that at least some of the carbohydrate moiety consisted of a complex N-linked carbohydrate. Although treatment of the membrane with glycosidases resulted in a molecular weight shift, it did not reduce the intensity of binding. This suggested that the antibody bound primarily to the polypeptide portion of the glycoprotein.

EXAMPLE 2

Identification of Antigens Bound by 7BD-33-11A

The data detailed in this example have been described previously in Ser. No. 10/810,751, the contents of which are herein incorporated by reference.

1.0 Immunoprecipitation of Antigens from MB-231 Total Membrane Fraction

Figure 4:
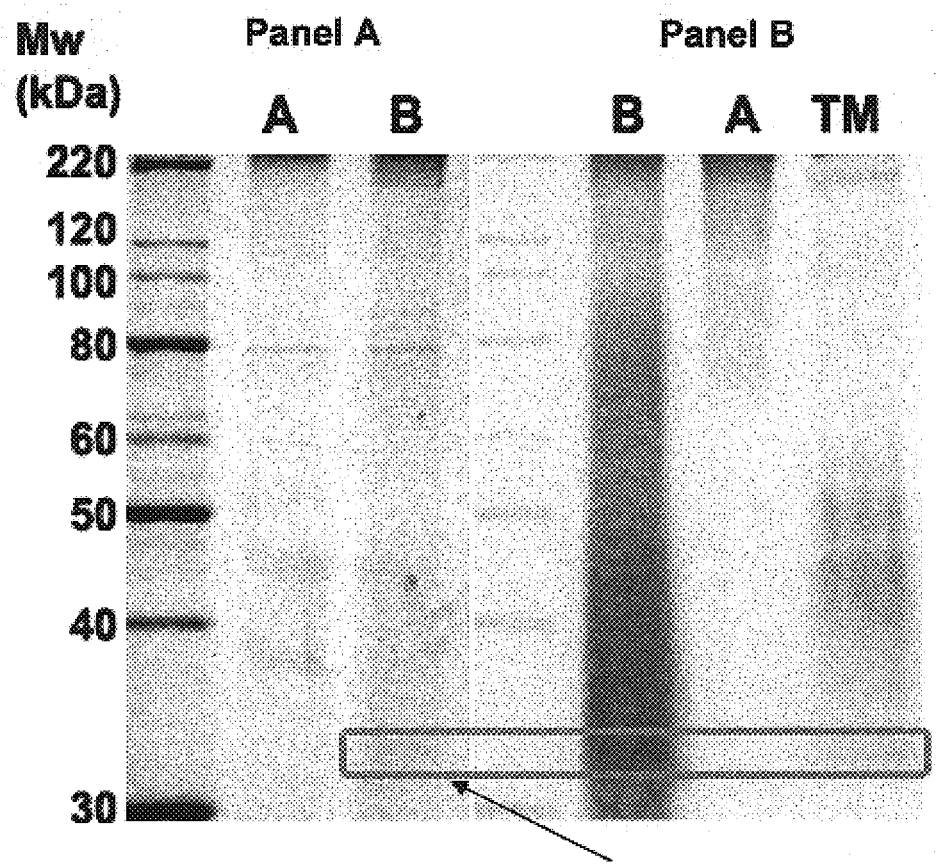
FIG. 4. SDS-PAGE (Panel A) and Western blot (Panel B) of MDA-MB-231 membrane proteins immunoprecipitated with 7BD-33-11A. Lane A isotype control immunoprecipitated proteins, Lane B: 7BD-33-11A immunoprecipitated proteins and Lane TM: Total MDA-MB-231 membrane proteins. Rectangular box outlines the same band from Lane B in the SDS-PAGE and Lane TM in the Western blot. Molecular weight markers are indicated on the left.

Total membrane extracts (5 mg total protein) were diluted to a 1 mg/mL final protein concentration with the appropriate volume of 1× lysis buffer (50 mM Tris pH 7.4, 150 mM NaCl, 1% Triton X-100, 0.02% $NaN_3$, 2 mM sodium orthovanadate, 50 mM sodium fluoride, and protease inhibitor cocktail (Roche Diagnostics, Manheim, Germany)), and with the appropriate volume of 2×RIPA buffer (50 mM Tris pH 7.4, 150 mM NaCl, 1.0% sodium cholate, 0.2% SDS, 1% Triton X-100 and 0.02% $NaN_3$), in order to obtain a final 1×RIPA buffer concentration. The extracts were pre-cleared for 2 hr with protein G-Sepharose beads (Amersham Biosciences, Uppsala, Sweden) at 4° C. Total membrane extracts were removed and stock BSA (10 mg/mL) was added to a 0.5 mg/mL final BSA concentration. While extracts were being pre-cleared, antibody-conjugated protein G-Sepharose beads (60 μg of antibody chemically cross-linked to 30 μl of protein G Sepharose) were blocked with 1 mL of 0.5 mg/mL BSA, by incubation at 4° C., also for 2 hr. After blocking, the antibody-conjugated beads were washed twice for 5 min with 1×RIPA buffer. The antibody-conjugated protein G-Sepharose beads were then added to the BSA-containing total membrane extracts, and incubated for 3 hr, at 4° C., on an end-over-end rotator. After centrifugation at 20,000 g, for 10 seconds, at 4° C., the unbound fraction was removed and discarded, and the beads were washed 3 times for 5 min, with 1 mL of RIPA buffer in each wash step. The beads were then rinsed once with 1.5 mL of PBS. The immunoprecipitation (IP) described above, with 7BD-33-11A-conjugated protein G Sepharose was carried out in parallel with a similar IP in which the protein G-Sepharose beads were chemically cross-linked with an $IgG_{2a}$ isotype control (BD Biosciences, San Diego, Calif.). This step was carried out to enable assessment of non-specific binding of proteins to the immunocomplexes. After completely draining the PBS, the beads were boiled in 40 μl of non-reducing sample buffer and the samples were analyzed by 1D SDS-PAGE followed by Western immunoblotting of a portion of the gel, and staining with Coomassie Colloidal Blue of the remaining portion of the gel. Of the 40 μl, a fraction (8 μl) was loaded onto the SDS-PAGE for Western blotting and the remaining fraction (32 μl) was loaded onto a separate lane of the same gel for protein staining with Coomassie Colloidal Blue. The portion of the gel designated for protein staining was incubated overnight with the Coomassie Colloidal Blue stain. The portion of the gel designated for Western blotting was transferred onto a PVDF membrane for 2 hr at 320 mA, rinsed with deionized water, blocked for 1 hr at RT with 5 percent milk in TBST and then incubated overnight at 4° C. with 7BD-33-11A in 5 percent milk in TBST. Blots were washed 3 times for 10 min in TBST and incubated with an HRP-conjugated Fc-specific goat anti-mouse IgG (1:5000) in 5 percent milk in TBST, for 1 hr at room temperature. Blots were then washed 3 times for 10 min and were developed with the TMB peroxidase substrate kit according to package insert instructions. As displayed in FIG. 4, the Western immunoblot and the Coomassie Colloidal Blue stained gel were lined up, using the molecular weight markers as reference. The main band that stained with Coomassie Colloidal Blue lined up with the main band that reacted with 7BD-33-11A on the Western blot. This section is highlighted (rectangle inset) on FIG. 4.

2.0 Peptide Mapping, and Antigen Identification by Mass Spectrometry

Figure 5:
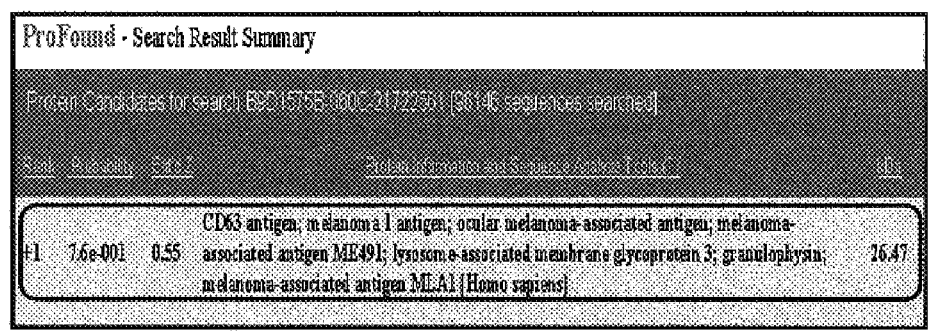
FIG. 5. Profound search summary table.
Figure 6:
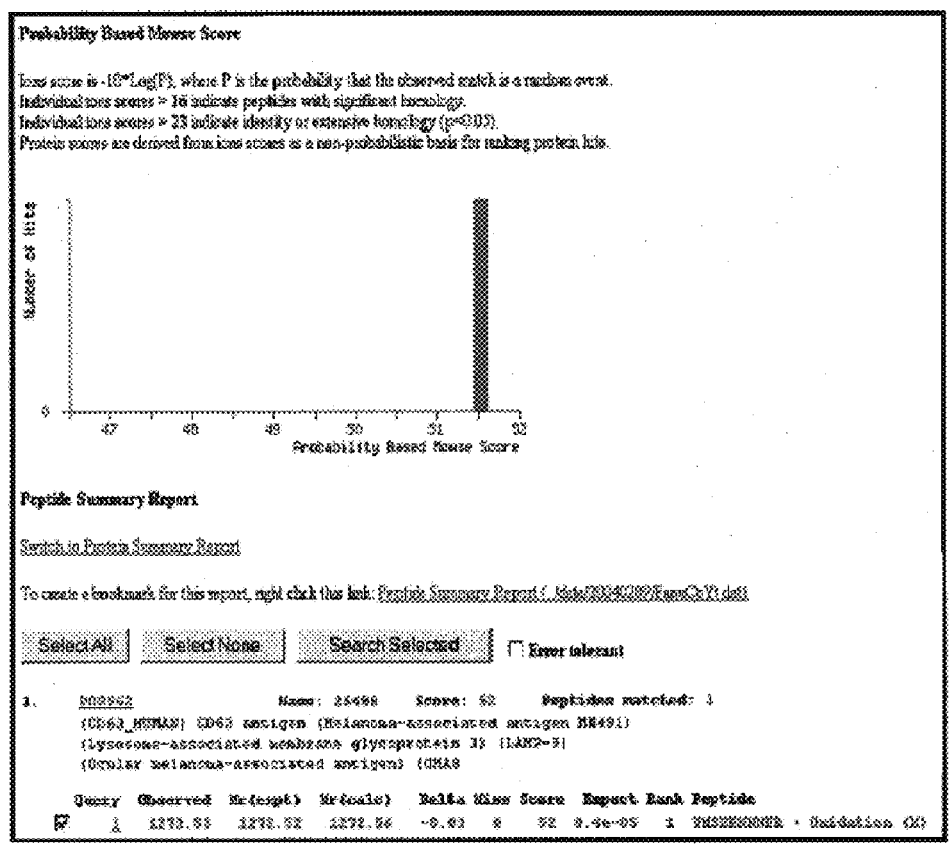
FIG. 6. MASCOT search summary table. The peptide disclosed in the lower right corner is designated SEQ ID NO:5.

From the experiment above, the band on the Coomassie Colloidal Blue stained gel that lined up with the most intense reactivity on the Western blot was then cut out and subjected to in-gel tryptic digestion using a commercially available kit (Pierce, Rockford, Ill.). Aliquots of the digest were subjected to mass spectrometry analysis on a SELDI-TOF Ciphergen PBSIIc reader (Ciphergen Biosystems Inc., Freemont, Calif.). Briefly, an aliquot of the digest was manually spotted onto an H4 chip (Ciphergen Biosystems Inc., Freemont, Calif.). After drying, an aliquot of CHCA matrix (α-cyano 4-hydroxy cinnaminic acid; Ciphergen Biosystems Inc., Freemont, Calif.) was added onto the same spot on the chip and allowed to dry. The sample was then analyzed on the PBSIIc reader. Similar sized bands from parallel regions on isotype control lanes and blank gel region were processed side-by-side with the gel plug from the 7BD-33-11A IP, so as to enable determination of unique peptide fragments generated by the digestion of the antigen immunoprecipitated by 7BD-33-11A. The masses of the unique peptide fragments were searched using PROFOUND, a publicly accessible online tool for searching protein sequence databases using information from mass spectra. The unique peptides in the sample from the 7BD-33-11A IP digest were then subjected to MS/MS analysis on a QSTAR (Applied Biosystems, Foster City, Calif.) equipped with an interface that enabled analysis of the same sample spots that were previously analyzed on the PBSIIc reader. The MS/MS data was then analyzed with MASCOT, a publicly accessible online tool for searching protein databases using information from MS/MS spectra. FIG. 5 is a summary of the table that resulted from the ProFound search. The only protein that was suggested as a putative candidate, with a significant degree of confidence was CD63. FIG. 6 is a summary table that resulted from the MASCOT search. The only protein that was identified with a high degree of probability was CD63, supporting the previous tentative identification by peptide map fingerprinting.

3.0 7BD-33-11A Antigen ID Confirmation

Figure 7A:
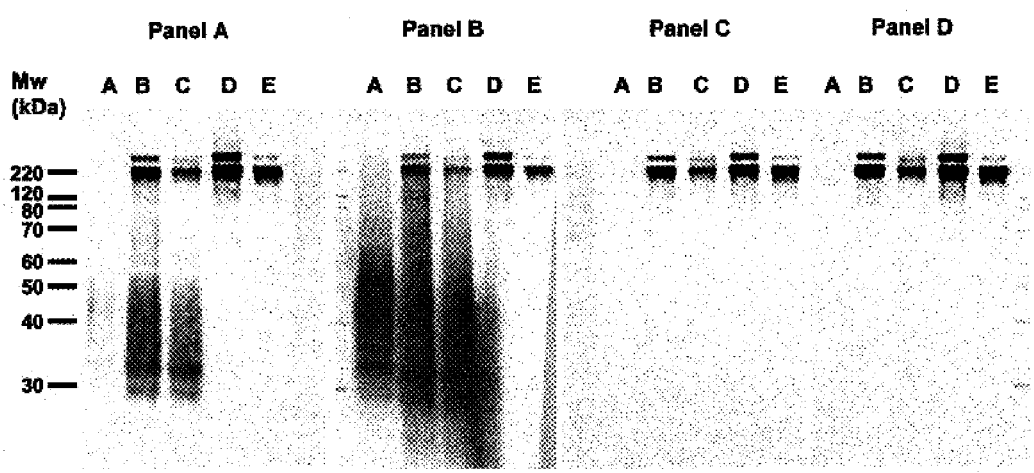
FIG. 7a: Western blots of proteins probed with 7BD-33-11A (Panel A), anti-CD63 (clone RFAC4, Panel B), $IgG_{2a}$ isotype control (Panel C) and $IgG_1$ isotype control (Panel D). Lane A: Total MDA-MB-231 membrane proteins; Lane B: 7BD-33-11A immunoprecipitated proteins; Lane C: anti-CD63 (RFAC4) immunoprecipitated proteins, Lane D: $IgG_{2a}$ isotype control immunoprecipitated proteins and Lane E: $IgG_1$ isotype control immunoprecipitated proteins. Molecular weight markers are indicated on the left.
Figure 7B:
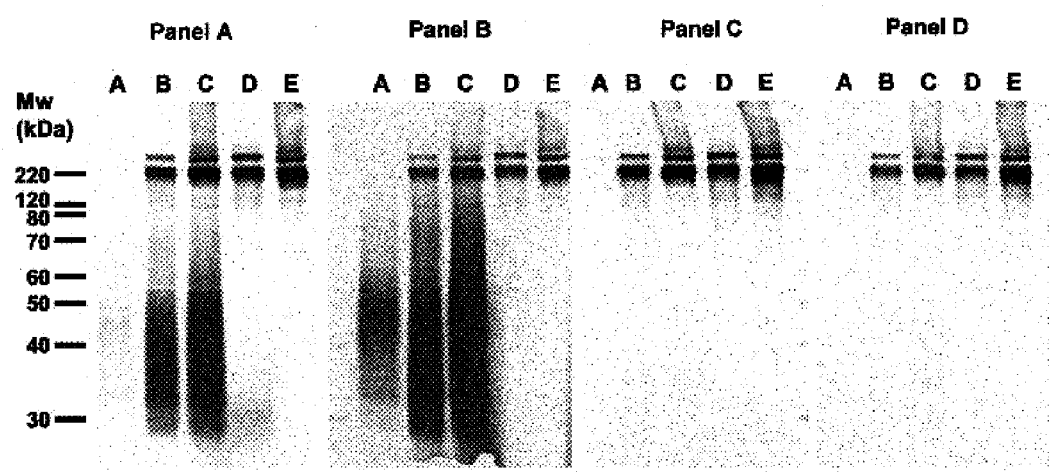
FIG. 7b: Western blots of proteins probed with 7BD-33-11A (Panel A), anti-CD63 (clone H5C6, Panel B), $IgG_{2a}$ isotype control (Panel C) and $IgG_1$ isotype control (Panel D). Lane A: Total MDA-MB-231 membrane proteins; Lane B: 7BD-33-11A immunoprecipitated proteins; Lane C: anti-CD63 (H5C6) immunoprecipitated proteins, Lane D: $IgG_{2a}$ isotype control immunoprecipitated proteins and Lane E: $IgG_1$ isotype control immunoprecipitated proteins. Molecular weight markers are indicated on the left.

Confirmation of the ID of the putative antigen for 7BD-33-11A was carried out through determination of whether known anti-human CD63 monoclonal antibodies, RFAC4 (Cymbus Biotechnology LTD, Hants, UK) and H5C6 (BD Biosciences, San Diego, Calif.) would react with the protein(s) immunoprecipitated by 7BD-33-11A, and vice versa. Further confirmation was carried out by Western immunoblotting of total lysates from induced and non-induced bacteria transformed with glutathione S-transferase (GST)-fusion constructs of the extracellular domains of human CD63. Immunoprecipitates from MB-231 total membrane prepared with the monoclonal antibodies 7BD-33-11A, RFAC4, H5C6, and with the $IgG_{2a}$ and $IgG_1$ (BD Biosciences, San Diego, Calif.) isotype controls, were analyzed by 1D SDS-PAGE followed by Western immunoblotting. Equal fraction volumes from each immunocomplex sample were analyzed on replicate gels. After electroblotting onto PVDF membranes, the blots from the replicate gels were probed in parallel with the monoclonal antibodies 7BD-33-11A, RFAC4, H5C6, and with the $IgG_{2a}$ and $IgG_1$ isotype controls. FIG. 7a demonstrates the result from the cross-IP experiments in which the material immunoprecipitated by each of the test monoclonal antibodies 7BD-33-11A and RFAC4 was analyzed by Western immunoblotting. FIG. 7b displays the result from the cross-IP experiments in which the material immunoprecipitated by each of the test monoclonal antibodies 7BD-33-11A and H5C6 was analyzed by Western immunoblotting. Each of the monoclonal antibodies 7BD-33-11A, RFAC4 and H5C5 cross-reacted with similar antigen(s) immunoprecipitated by 7BD-33-11A. In addition, 7BD-33-11A cross reacted, on a Western blot, with similar antigen(s) immunoprecipitated by RFAC4 and H5C6, in the range of 20-80 kDa, but not with the immunocomplexes prepared with the isotype control antibodies. The blots probed with the isotype control antibodies were completely negative. This data indicated that the epitope recognized by the 7BD-33-11A antibody was contained within the CD63 antigen.

Figure 8:
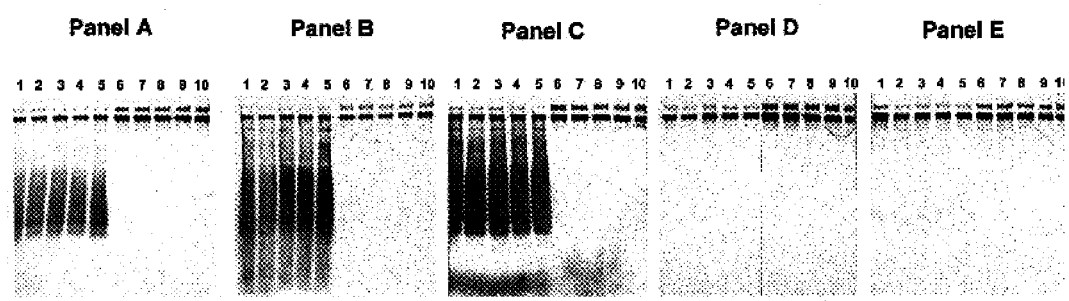
FIG. 8. Western blots of proteins probed with 7BD-33-11A (Panel A), anti-CD63 (clone RFAC4, Panel B), anti-CD63 (clone H5C6, Panel C), $IgG_{2a}$ isotype control (Panel D) and $IgG_1$ isotype control (Panel E). Lanes 1-5 contain 7BD-33-11A immunoprecipitated proteins and Lanes 6-10 contain $IgG_{2a}$ isotype control immunoprecipitated proteins. Lanes 1 and 6: no NaCl, Lanes 2 and 7: 150 mM NaCl, Lanes 3 and 8: 500 mM NaCl, Lanes 4 and 9: 2000 mM NaCl and Lanes 5 and 10: RIPA buffer.

To determine if the cross-reactivity could be due to the same molecules being recognized by all antibodies, or if it was due to the presence of interacting molecules with similar mass, immunoprecipitations with the antibody 7BD-33-11A were carried out in conditions of increasing buffer stringency (50 mM Tris pH 7.4, 1% Triton X-100, and varying concentrations of NaCl: 0, 150, 500 and 2000 mM; and also with RIPA buffer as described above but containing 500 mM NaCl). The resulting immunocomplexes were then probed by Western immunoblotting with the monoclonal antibodies 7BD-33-11A, H5C6 and RFAC4 and with the isotype controls IgG$_{2a}$ and IgG$_1$. FIG. 8 showed that varying the stringency of the IP conditions did not have any detectable impact on the formation of the immunocomplexes, which indicated that the molecule(s) recognized by the antibody 7BD-33-11A were also recognized by the anti-CD63 antibodies and vice versa.

To further confirm that 7BD-33-11A was directly binding to the human CD63 antigen, its reactivity was assessed, by Western immunoblotting against lysates of *E. coli* expressing recombinant fusion polypeptides containing the extracellular domains (loops EC1 and EC2) of human CD63. For this work, GST-fusion constructs of the extracellular loops of CD63 (loop 1 and loop 2-EC1 and EC2, respectively) were generated by subcloning the appropriate cDNA fragments into the bacterial expression vector PGEX-4T-2 (Amersham Biosciences, Piscataway, N.J.). The cDNA fragments encoding the loops were obtained by polymerase chain reaction amplification (PCR), using the full-length human cDNA as a template (clone MGC-8339, American Type Culture Collection, Manassas, Va.). The cDNA encoding the EC1 loop was obtained using the following PCR primers:

```
5' primer (EC1_5'),
5'GCCGTGGGATCCGGGGCACAGCTTGTCCTG3'
(SEQ ID NO:1)

and

3' primer (EC1_3'),
5'GATGACGAATTCTCACAGAGAGCCAGGGGTAGC3'.
(SEQ ID NO:2)
```

The cDNA encoding the EC2 loop was obtained using the following PCR primers:

```
5' primer (EC2_5'),
5'GGCTATGGATCCAGAGATAAGGTGATG3'
(SEQ ID NO:3)

and

3' primer (EC2_3'),
5'TACCAGAATTCAATTTTTCCTCAGCCAGCC3'.
(SEQ ID NO:4)
```

The conditions for the PCR reactions were as follows: 2 µL of 5' primer (25 pmol/µL), 2 µL of 3' primer (25 pmol/µL), 0.2 µL of template DNA (pOTB-CD63, 0.76 mg/mL), and 45.8 µL of PCR SuperMix High Fidelity (Invitrogen, Burlington, ON). The PCR reaction was carried out as follows: 94° C. for 5 min followed by 30 cycles of: melting at 94° C. for 30 sec, annealing at 55° C. for 30 sec and extension at 72° C. for 1 min, per cycle.

Figure 9:
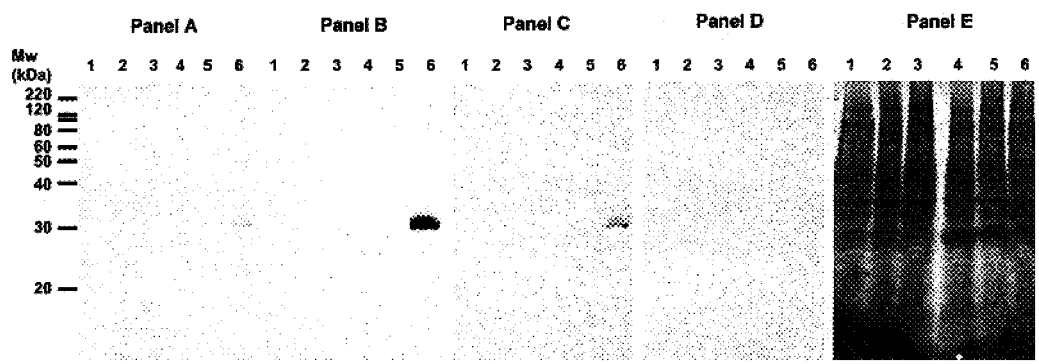
FIG. 9. Western blots of proteins probed with 7BD-33-11A (Panel A), anti-CD63 (clone RFAC4, Panel B), anti-CD63 (clone H5C6, Panel C), IgG2a protein isotype control (Panel D) and Coomassie Colloidal Blue protein stain (Panel E). Lane 1: non-induced vector alone, Lane 2: non-induced GST-EC1, Lane 3: non-induced GST-EC2, Lane 4: induced vector alone, Lane 5: induced GST-EC1 and Lane 6: induced GST-EC2. Molecular weight markers are indicated on the left.

After subcloning, the constructs, including a PGEX-4T-2 vector alone negative control (no cDNA fragment subcloned into the vector), were transformed into *E. coli* (strain BL-21). A single ampicillin-resistant colony from each transformation was grown and the respective insert cDNAs were sequenced. After confirming that the cDNA sequence was correct, each of the clones was grown in liquid culture and the expression of the GST-fusion constructs was induced by addition of 1 mM IPTG (isopropyl-β-D-thiogalactopyranoside) (Gibco-BRL; Rockville, Md.). After a 2 hr incubation, the bacteria culture was centrifuged at 2000 g, for 5 min, at room temperature. The supernatant was discarded and the bacteria pellets were boiled in non-reducing SDS-PAGE sample buffer. The samples were then analyzed by SDS-PAGE (5 and 12 percent) polyacrylamide stacking and separating gels respectively) and Western immunoblotting, as previously described. Blot membranes were probed with 7BD-33-11A, H5C6, RFAC4, or with an IgG2a isotype control. The results illustrated by FIG. 9 revealed that 7BD-33-11A specifically recognized loop 2 (amino acids 108-202) of human CD63 (lane 6 of blot probed with 7BD-33-11A), and does not recognize loop 1 (amino acids 34-52). The specificity of the antibody against the bacterial lysate was further confirmed by the observation that two well-characterized anti-human CD63 antibodies (RFAC4 and H5C6) also recognized a similar size band, only on the lysates from induced *E. coli* expressing the EC2 fusion polypeptide. All of the above results demonstrate that 7BD-33-11A recognized and directly bound to human CD63, and specifically to the extracellular region encompassing amino acids 108-202.

EXAMPLE 3

Identification of Antigens Bound by 1A245.6 and H460-22-1

1.0 Immunoprecipitation of Antigens from MB-231 Total Membrane Fraction

Figure 10:
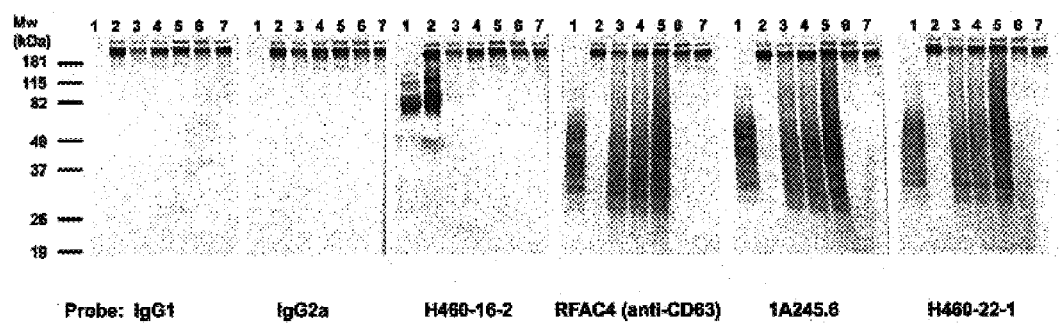
FIG. 10. Western blots of proteins probed with $IgG_1$ and $IgG_{2a}$ Isotype Control, anti-CD44 (clone H460-16-2), anti-CD63 (RFAC4), 1A245.6 and H460-22-1. Lane 1: total membrane fraction (Lane 1), Lane 2: material immunoprecipitated with H460-16-2, Lane 3: material immunoprecipitated with 7BD-33-11A, Lane 4: material immunoprecipitated with H460-22-1, Lane 5: material immunoprecipitated with 1A245.6, Lane 6: material immunoprecipitated with $IgG_{2a}$ isotype control and Lane 7: material immunoprecipitated with $IgG_1$ isotype control. Molecular weight markers are indicated on the left.

Total membrane extracts (1 mg total protein) were diluted to a 1 mg/mL final protein concentration with the appropriate volume of 1× lysis buffer (50 mM Tris pH 7.4, 150 mM NaCl, 1% Triton X-100, 0.02% NaN$_3$, 2 mM sodium orthovanadate, 50 mM NaF, and protease inhibitor cocktail), and with the appropriate volume of 2× RIPA buffer (50 mM Tris pH 7.4, 150 mM NaCl, 1.0% NaCholate, 0.2% SDS, 1% Triton X-100 and 0.02% NaN$_3$), in order to obtain a final 1× RIPA buffer concentration. The extracts were pre-cleared for 2 hr with protein G-Sepharose beads (Amersham Biosciences; Uppsala, Sweden) at 4° C. Total membrane extracts were removed and stock BSA (10 mg/mL) was added to a 0.5 mg/mL final BSA concentration. While extracts were being pre-cleared, antibody-conjugated protein G-Sepharose beads (60 µg of antibody chemically cross-linked to 30 µl of protein G Sepharose) were blocked with 1 mL of 0.5 mg/mL BSA, by incubation at 4° C., also for 2 hr. After blocking, the antibody-conjugated beads were washed twice for 5 min with 1× RIPA buffer. The antibody-conjugated protein G-Sepharose beads were then added to the BSA-containing total membrane extracts, and incubated at for 3 hr, at 4° C., on an end-over-end rotator. After centrifugation at 20,000 g, for 10 seconds, at 4° C., the unbound fraction was removed and discarded, and the beads were washed 3 times for 5 min, with 1 mL of RIPA buffer in each wash step. The beads were then rinsed once with 1.5 mL of PBS. The immunoprecipitations (IP) with the protein G-Sepharose-conjugated monoclonal antibodies 7BD-33-11A, 1A245.6, H460-22-1, IgG$_1$ isotype control, IgG$_{2a}$ isotype control and H460-16-2 (the latter is a well characterized antibody known to specifically recognize CD44), were carried out in parallel. After completely draining the PBS, the beads were boiled in 40 µl of non-reducing sample buffer and the samples were analyzed by ID SDS-PAGE followed by Western immunoblotting. Replicate gels were transferred onto PVDF membranes for 2 hr at 320 mA. The membranes were then rinsed with deionized water, blocked for 1 hr at RT with 5% milk in TBST. Replicate membranes were incubated overnight at 4° C. with the monoclonal antibodies RFAC4 (anti-CD63), 1A245.6, H460-22-1, H460-16-2, and with the isotype controls IgG$_1$ and IgG$_{2a}$, in 5% milk in TBST. Blots were washed 3 times for 10 min in TBST and incubated with an HRP-conjugated Fc-specific goat anti-mouse IgG (1:5000 dilution) in 5% milk in TBST, for 1 hr at room temperature. Blots were then washed 3 times for 10 min and were developed according to the standard procedure of TMB substrate for HRP. As displayed in FIG. 10, the blots probed with the antibodies RFAC4 (anti-CD63), 1A245.6 and H460-22-1 revealed identical patterns of reactivity. All three antibodies cross-reacted with material immunoprecipitated with the antibodies 7BD-33-11A, H460-22-1 and 1A245.6 (Lanes 3, 4 and 5, respectively), and characterized by reactivity in a range of apparent molecular weight from 20 to 80 kDa. A similar pattern of reactivity can also be observed on the lane loaded with the unfractionated total membrane detergent extract (Lane 1). In addition, none of these antibodies cross-reacted with material immunoprecipitated by the anti-CD44 antibody H460-16-2 (Lane 2), and the latter did not recognize the material immunoprecipitated by antibodies other than H460-16-2 (Lanes 3, 4 and 5). No non-specific cross-reactivity was detected on the replicate blots probed with the isotype control antibodies. These results therefore strongly suggested that the antibodies 1A245.6 and H460-22-1 recognized the same antigen molecule as the antibodies RFAC4 and 7BD-33-11A, CD63.

2.0 1A245.6 and H460-22-1 Antigen ID Confirmation

To confirm that 1A245.6 and H460-22-1 bound directly to the human CD63 antigen, their reactivity was assessed, by Western immunoblotting against lysates of E. coli expressing recombinant fusion polypeptides containing the extracellular domains (loops EC1 and EC2) of human CD63. For this work, GST-fusion constructs of the extracellular loops of CD63 (loop 1 and loop 2-EC1 and EC2, respectively) were generated by subcloning the appropriate cDNA fragments into the bacterial expression vector PGEX-4T-2 (Amersham Biosciences, Piscataway, N.J.) The cDNA fragments encoding the loops were obtained by polymerase chain reaction amplification (PCR), using the full-length human cDNA as a template (clone MGC-8339, American Type Culture Collection, Manassas, Va.). The cDNA encoding the EC1 loop was obtained using the following PCR primers:

```
5' primer (EC1_5'),
5'GCCGTGGGATCCGGGGCACAGCTTGTCCTG3'
(SEQ ID NO:1)

and

3' primer (EC1_3'),
5'GATGACGAATTCTCACAGAGAGCCAGGGGTAGC3'.
(SEQ ID NO:2)
```

The cDNA encoding the EC2 loop was obtained using the following PCR primers:

```
5' primer (EC2_5'),
5'GGCTATGGATCCAGAGATAAGGTGATG3'
(SEQ ID NO:3)

and

3' primer (EC2_3'),
5'TACCAGAATTCAATTTTTCCTCAGCCAGCC3'.
(SEQ ID NO:4)
```

The conditions for the PCR reactions were as follows: 2 µL of 5' primer (25 pmol/µL), 2 µL of 3' primer (25 pmol/µmL), 0.2 µL of template DNA (pOTB-CD63, 0.76 mg/mL), and 45.8 µL of PCR SuperMix High Fidelity (Invitrogen). The PCR reaction was carried out as follows: 94° C. for 5 min followed by 30 cycles of: melting at 94° C. for 30 sec, annealing at 55° C. for 30 sec and extension at 72° C. for 1 min, per cycle.

Figure 11:
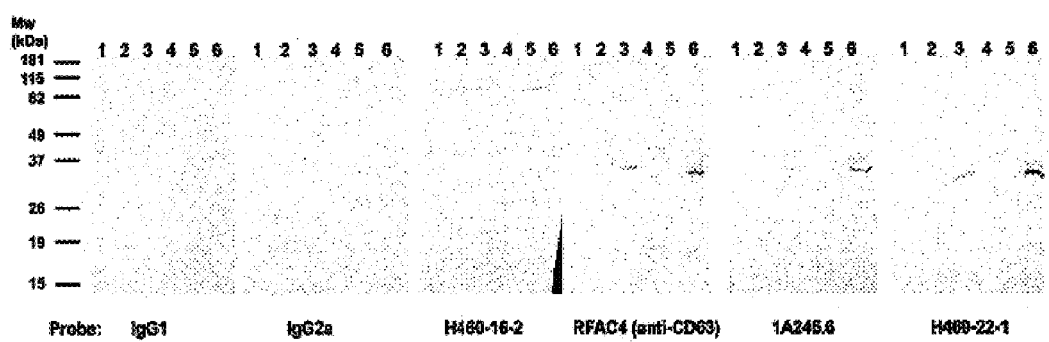
FIG. 11. Western blots of proteins probed with $IgG_1$ and $IgG_{2a}$ Isotype Control, anti-CD44 (clone H460-16-2), anti-CD63 (RFAC4), 1A245.6 and H460-22-1. Lane 1: non-induced GST vector alone, Lane 2: non-induced GST-EC1, Lane 3: non-induced GST-EC2, Lane 4: induced GST vector alone, Lane 5: induced GST-EC1, Lane 6: induced GST-EC2. Molecular weight markers are indicated on the left.

After subcloning, the constructs, including a PGEX-4T-2 vector alone negative control (no cDNA fragment subcloned into the vector), were transformed into E. coli (strain BL-21). A single ampicillin-resistant colony from each transformation was grown and the respective insert cDNAs were sequenced. After confirming that the cDNA sequence was correct each of these clones was grown in liquid culture and the expression of the GST-fusion constructs was induced by addition of 1 mM IPTG (isopropyl-β-D-thiogalactopyranoside) (Gibco-BRL; Rockville, Md.). After a 2 hr incubation, the bacteria culture was centrifuged at 2000 g, for 5 min, at room temperature. The supernatant was discarded and the bacteria pellets were boiled in non-reducing SDS-PAGE sample buffer. The samples were then analyzed by SDS-PAGE (5% and 12% polyacrylamide stacking and separating gels, respectively) and Western immunoblotting, as previously described. Blot membranes were probed with the 1A245.6, H460-22-1, RFAC4, H460-16-2 and $IgG_1$ and $IgG_{2a}$ isotype controls. All the antibodies were used at a concentration of 5 µg/mL. The results illustrated by FIG. 11 revealed that 1A245.6 and H460-22-1 specifically recognize loop 2 (amino acids 108-202) of human CD63 (Lane 6 of blots probed with 1A245.6 and H460-22-1), and do not recognize loop 1 (amino acids 34-52) nor the GST vector alone. The specificity of the antibody against the bacterial lysates was further confirmed by the observation that a well-characterized anti-human CD63 antibody (RFAC4) also recognized a similar size band, only on the lysates from E. coli expressing the GST-EC2 fusion polypeptide. In addition an antibody that recognizes human CD44 (H460-16-2) did not recognize any of the recombinant proteins expressed in this experiment. All of the above results showed that 1A245.6 and H460-22-1 recognized and directly bound to human CD63, and specifically to the extracellular region encompassing amino acids 108-202.

EXAMPLE 4

As outlined in Ser. No. 10/348,231, Ser. No. 10/603,006, Ser. No. 10/810,751 and Ser. No. 10/891,866, the contents of each of which are herein incorporated by reference, for the hybridoma cell line 7BD-33-11A and 1A245.6 and herein for the hybridoma cell line H460-22-1, the three hybridoma clones were deposited, in accordance with the Budapest Treaty, with the American Type Culture Collection, 10801 University Blvd., Manassas, Va. 20110-2209 on Sep. 4, 2003 under Accession Number PTA-4622 for H460-22-1 and on Jan. 8, 2003, under Accession Number PTA-4889 and PTA-4890 for 1A245.6 and 7BD-33-11A respectively. In accordance with 37 CFR 1.808, the depositors assure that all restrictions imposed on the availability to the public of the deposited materials will be irrevocably removed upon the granting of a patent.

Antibody Production:

The H460-22-1, 1A245.6 and 7BD-33-11A monoclonal antibodies were produced by culturing the hybridomas in CL-1000 flasks (BD Biosciences, Oakville, ON) with collections and reseeding occurring twice/week. The antibodies were purified according to standard antibody purification procedures with Protein G Sepharose 4 Fast Flow (Amersham Biosciences, Baie d'Urfé, QC).

As previously described in Ser. No. 10/348,231, Ser. No. 10/603,006, Ser. No. 10/810,751 and Ser. No. 10/891,866, the contents of each of which are herein incorporated by reference, for 7BD-33-1A and 1A245.6 and as outlined herein for H460-22-1, the three antibodies were compared to a number of both positive (anti-Fas (EOS9.1, IgM, kappa, 20 micrograms/mL, eBioscience, San Diego, Calif.), anti-Her2/neu (IgG1, kappa, 10 microgram/mL, Inter Medico, Markham, ON), anti-EGFR (C225, IgG1, kappa, 5 microgram/mL, Cedarlane, Hornby, ON), Cycloheximide (100 micromolar, Sigma, Oakville, ON), $NaN_3$ (0.1%, Sigma, Oakville, ON)) and negative (107.3 (anti-TNP, IgG1, kappa, 20 microgram/mL, BD Biosciences, Oakville, ON), G155-178 (anti-TNP, IgG2a, kappa, 20 microgram/mL, BD Biosciences, Oakville, ON), MPC-11 (antigenic specificity unknown, IgG2b, kappa, 20 microgram/mL), J606 (anti-fructosan, IgG3, kappa, 20 microgram/mL), IgG Buffer (2%)) controls in a cytotoxicity assay (Tables 1 and 2). Breast cancer (MB-231, MB-468, MCF-7), colon cancer (HT-29, SW1116, SW620), lung cancer (NCI H460), ovarian cancer (OVCAR), prostate cancer (PC-3), melanoma (A2058, A357 and A549) and non-cancer (Hs578.Bst, CCD 27sk, Hs888 Lu) cell lines were tested (all from the ATCC, Manassas, Va.). The Live/Dead cytotoxicity assay was obtained from Molecular Probes (Eugene, Oreg.). The assays were performed according to the manufacturer's instructions with the changes outlined below. Cells were plated before the assay at the predetermined appropriate density. After 2 days, purified antibody or controls were diluted into media, and then 100 μL were transferred to the cell plates and incubated in a 5 percent $CO_2$ incubator for 5 days. The plate was then emptied by inverting and blotted dry. Room temperature DPBS containing $MgCl_2$ and $CaCl_2$ was dispensed into each well from a multi-channel squeeze bottle, tapped three times, emptied by inversion and then blotted dry. 50 μL of the fluorescent calcein dye diluted in DPBS containing $MgCl_2$ and $CaCl_2$ was added to each well and incubated at 37° C. in a 5 percent $CO_2$ incubator for 30 minutes. The plates were read in a Perkin-Elmer HTS7000 fluorescence plate reader and the data was analyzed in Microsoft Excel and the results were tabulated in Tables 1 and 2. The data represented an average of four experiments tested in triplicate and presented qualitatively in the following fashion: 4/4 experiments greater than threshold cytotoxicity (+++), 3/4 experiments greater than threshold cytotoxicity (++), 2/4 experiments greater than threshold cytotoxicity (+). Unmarked cells in Table 1 represent inconsistent or effects less than the threshold cytotoxicity. The 7BD-33-11A antibody demonstrated cytotoxicity in a breast and prostate tumor cell line selectively, while having no effect on non-transformed normal cells. 7BD-33-11A and 1A245.6 demonstrated greater killing than the control anti-Fas or anti-EGFR antibody on the prostate cancer cell line. H460-22-1 demonstrated greater killing than anti-Fas or anti-EGFR on the MB-231 cell line. The chemical cytotoxic agents induced their expected cytotoxicity while a number of other antibodies which were included for comparison also performed as expected given the limitations of biological cell assays. In toto, it was shown that the 7BD-33-11A, 1A245.6 and H460-22-1 antibodies had cytotoxic activity against a number of cancer cell types. These antibodies were selective in their activity since not all cancer cell types were susceptible. Furthermore, the antibodies demonstrated functional specificity since they did not produce cytotoxicity against non-cancer cell types, which is an important factor in a therapeutic situation.

TABLE 1

| | | BREAST | | | COLON | | LUNG | OVARY | PROSTATE | NORMAL | |
|---|---|---|---|---|---|---|---|---|---|---|---|
| | | MB-231 | MB-468 | MCF-7 | HT-29 | SW1116 | SW620 | NCI H460 | OVCAR | PC-3 | CCD 27sk | Hs888 Lu |
| | 7BD-33-11A | | | + | | | | | | ++ | | |
| | 1A245.6 | | | + | | | | | | ++ | | |
| Positive Controls | anti-Fas | | | +++ | | | | | +++ | + | | + |
| | anti-Her2 | + | | + | | | | | + | | | |
| | anti-EGFR | | +++ | + | | +++ | | | + | | + | |
| | CHX(100 M) | +++ | +++ | +++ | +++ | +++ | +++ | +++ | +++ | +++ | +++ | +++ |
| | $NaN_3$(0.1%) | +++ | +++ | +++ | +++ | | | +++ | +++ | +++ | | |
| Nagative Controls | IgG1 | | | | | | | +++ | | + | | |
| | IgG2a | | | +++ | | + | | | | | | |
| | IgG2b | | | +++ | | | | | | | | |
| | IgG3 | | | | | | | | | | | |
| | IgG Buffer | + | | | | | | | | | | |

TABLE 2

| | | MELANOMA | | | COLON | BREAST | | LUNG | OVARY | PROSTATE | NORMAL | | |
|---|---|---|---|---|---|---|---|---|---|---|---|---|---|
| | Clone | A2058 | A375 | A549 | HT-29 | MB-231 | MB-468 | NCI H460 | OVCAR | PC-3 | Hs578.Bst | CCD 27sk | Hs888 Lu |
| | H460-22-1 | ++ | + | | | +++ | + | | | | | | |
| Nagative Controls | IgG1 Isotype | | | | | + | + | | | | | | |
| | IgG | | | | | | + | + | | + | | | |
| Positive Controls | aFas Buffer | ++ | +++ | | | | | +++ | | | | | |
| | aHer2 | | | | | | | | ++ | | | | |
| | CHX | +++ | +++ | +++ | +++ | +++ | +++ | +++ | +++ | +++ | +++ | +++ | +++ |

Binding of 7BD-33-11A to the above-mentioned panel of cancer and normal cell lines and to the following additional cancer cell lines; colon (LOVO), pancreatic (BxPC-3), ovarian (ES-2, OCC-1) and prostate (DU-145) and the following additional normal cell line (CCD-112) was assessed by flow cytometry (FACS, referenced in Ser. No. 10/348,231, Ser. No. 10/603,006 and Ser. No. 10/810,751, the contents of each of which are herein incorporated by reference). Binding of 1A245.6 (as references in Ser. No. 10/348,231, Ser. No. 10/603,006, Ser. No. 10/810,751 and Ser. No. 10/891,866, the contents of each of which are herein incorporated by reference) and H460-22-1 to the above-mentioned panel of cancer and normal cell lines was also assessed by FACS. Cells were prepared for FACS by initially washing the cell monolayer with DPBS (without $Ca^{++}$ and $Mg^{++}$). Cell dissociation buffer (INVITROGEN, Burlington, ON) was then used to dislodge the cells from their cell culture plates at 37° C. After centrifugation and collection the cells were resuspended in Dulbecco's phosphate buffered saline containing $MgCl_2$, $CaCl_2$ and 2 or 25 percent fetal bovine serum (FBS) at 4° C. (wash media) and counted, aliquoted to appropriate cell density, spun down to pellet the cells and resuspended in staining media (DPBS containing $MgCl_2$ and $CaCl_2$+/−2 percent FBS) containing 7BD-33-11A or control antibodies (isotype control or anti-EGFR) at 20 μg/mL on ice for 30 min. Prior to the addition of Alexa Fluor 488-conjugated secondary antibody the cells were washed once with wash media. The Alexa Fluor 488-conjugated antibody in staining media was then added for 20 to 30 min. The cells were then washed for the final time and resuspended in staining media containing 1 μg/mL propidium iodide or 1.5 percent paraformaldehyde. Flow cytometric acquisition of the cells was assessed by running samples on a FACScan using the CellQuest software (BD Biosciences). The forward (FSC) and side scatter (SSC) of the cells were set by adjusting the voltage and amplitude gains on the FSC and SSC detectors. The detectors for the three fluorescence channels (FL1, FL2, and FL3) were adjusted by running cells stained with purified isotype control antibody followed by Alexa Fluor 488-conjugated secondary antibody such that cells had a uniform peak with a median fluorescence intensity of approximately 1-5 units. Live cells were acquired by gating for FSC and propidium iodide exclusion (when used). For each sample, approximately 10,000 live cells were acquired for analysis and the results presented in Tables 3, 4 and 5. Tables 3, 4 and 5 tabulated the mean fluorescence intensity fold increase above isotype control for 7BD-33-11A, 1A245.6 and H460-22-1, respectively, and is presented qualitatively as: less than 5 (−); 5 to 50 (+); 50 to 100 (++); above 100 (+++) and in parenthesis, the percentage of cells stained.

Figure 12:
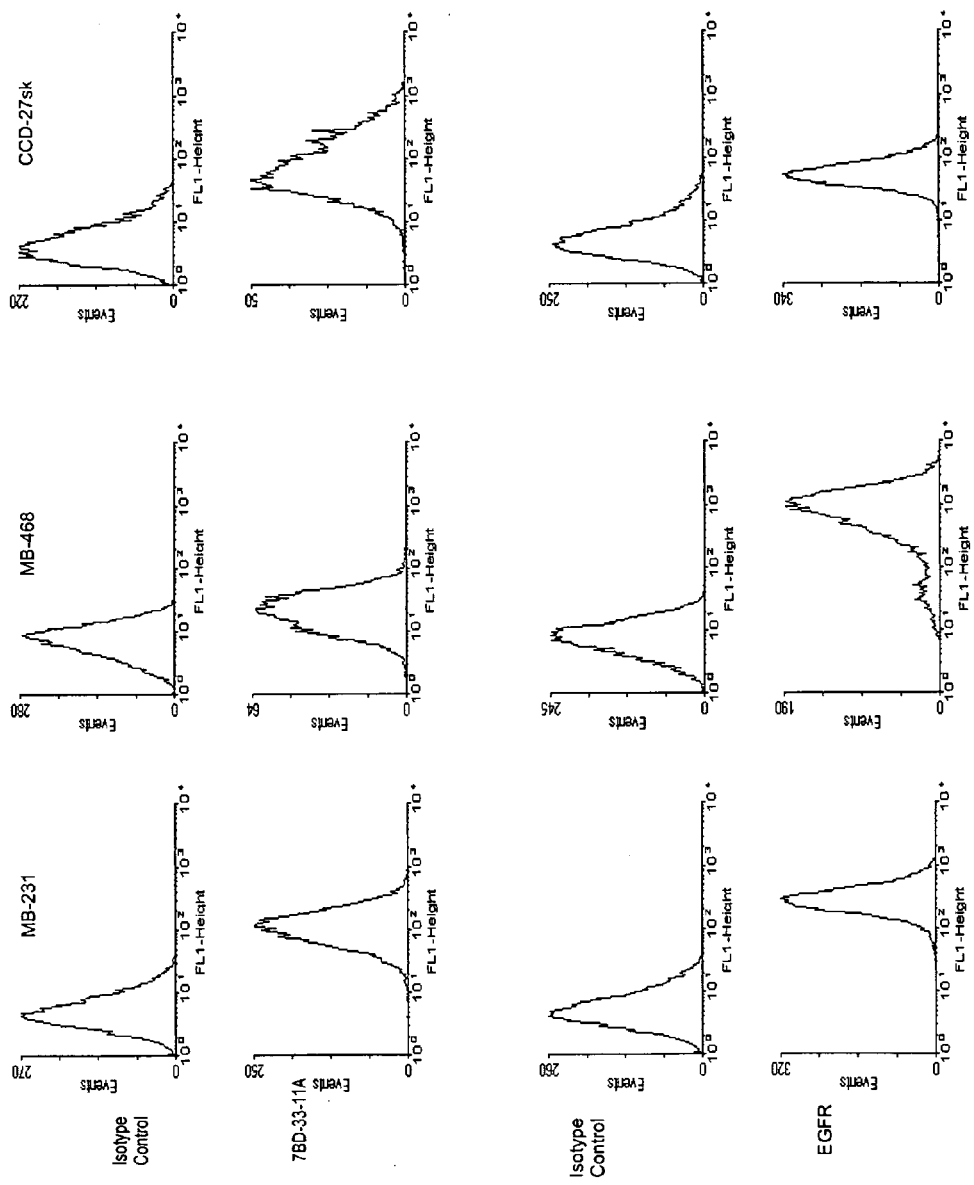
FIG. 12. Representative FACS histograms of 7BD-33-11A, isotype controls and anti-EGFR directed against several cancer cell lines and non-cancer cells.
Figure 13:
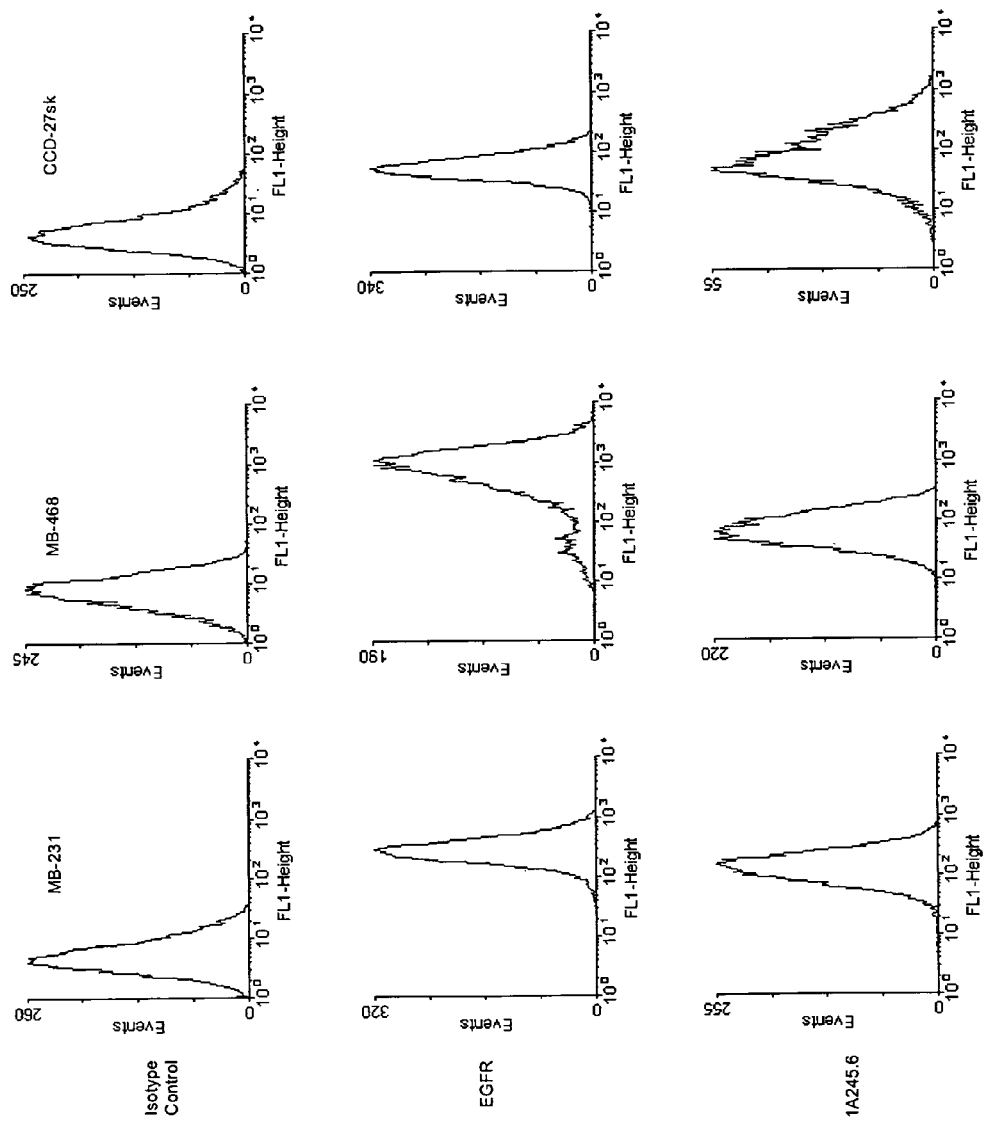
FIG. 13. Representative FACS histograms of 1A245.6, isotype controls and anti-EGFR directed against several cancer cell lines and non-cancer cells.
Figure 14:
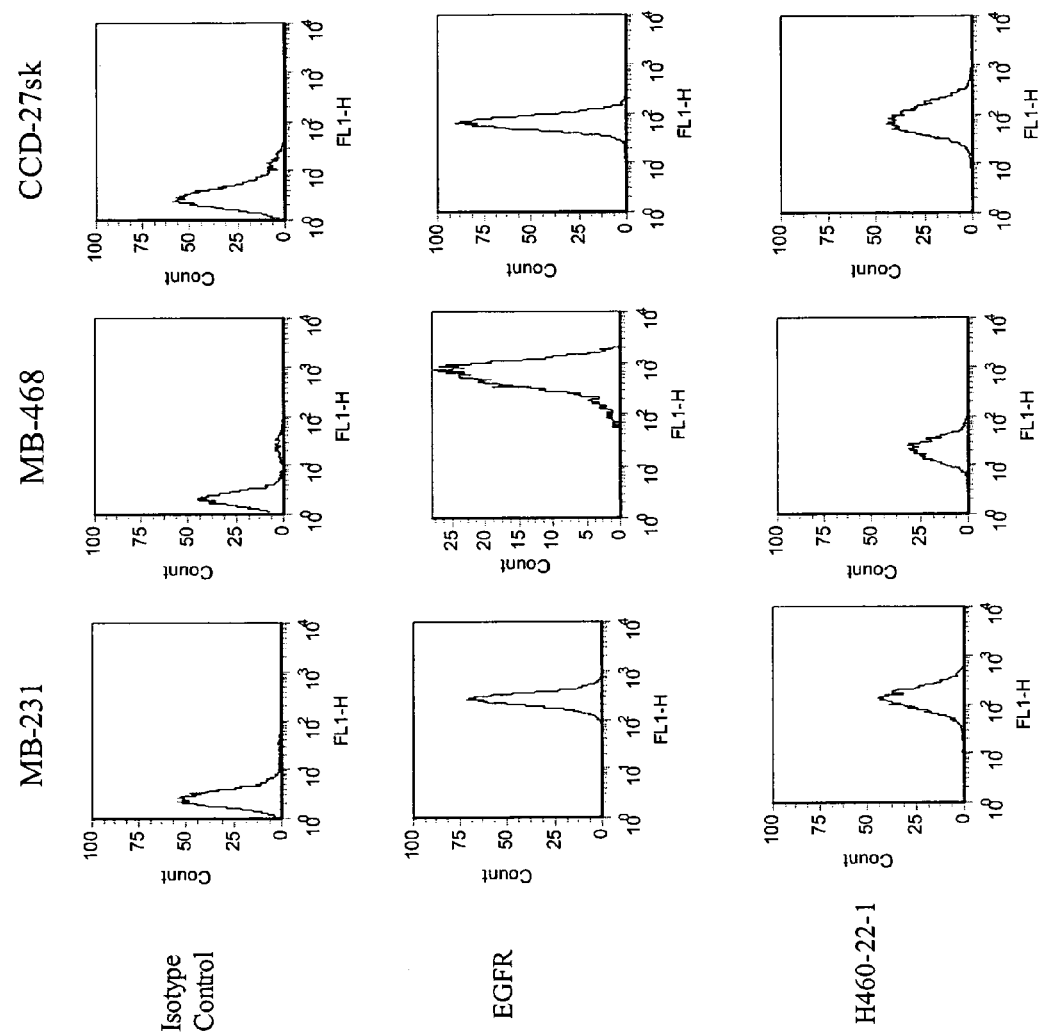
FIG. 14. Representative FACS histograms of H460-22-1, isotype controls and anti-EGFR directed against several cancer cell lines and non-cancer cells.

Representative histograms of 7BD-33-11A, 1A245.6 and H460-22-1 antibodies were compiled for FIGS. 12, 13 and 14 respectively. 7BD-33-11A displayed similar binding to cancer lines of breast (MB-231 and MCF-7), colon (HT-29, SW1116 and SW520), lung, ovary, pancreatic and prostate (PC-3) origin and differential binding to one of the breast (MB-468), colon (LOVO) and prostate (DU-145) cancer cell lines. 1A245.6 displayed similar binding to cancer lines of breast (MB-231, MB-468 and MCF-7), colon (SW1116 and SW520), lung, ovary, and prostate origin and differential binding to one of the colon (HT-29) cancer cell lines. H460-22-1 displayed similar binding to the tested cancer cell lines. There was also binding of 7BD-33-11A, 1A245.6 and H460-22-1 to non-cancer cells, however that binding did not produce cytotoxicity. This was further evidence that binding was not necessarily predictive of the outcome of antibody ligation of its cognate antigen, and was a non-obvious finding. This suggested that the context of antibody ligation in different cells determined cytoxicity, rather than just antibody binding.

TABLE 3

|  |  | 7BD-33-11A IgG2a, ? | Anti-EGFR IgG1, ? |
|---|---|---|---|
| Breast | MB-231 | + | ++ |
|  | MB-468 | − | ++ |
|  | MCF-7 | + | − |
| Colon | HT-29 | + | + |
|  | LOVO | − | − |
|  | SW1116 | + | + |
|  | SW620 | + | − |
| Lung | NCI H460 | + | + |
| Ovary | ES-2 | + | + |
|  | OCC-1 | + | + |
|  | OVCAR | + | + |
| Pancreatic | BxPC-3 | + | + |
| Prostate | DU-145 | − | + |
|  | PC-3 | + | + |
| Normal | CCD27sk | + | + |
|  | CCD-112 | + | + |
|  | Hs888Lu | + | + |

TABLE 4

|  |  | BREAST | | | COLON | | | LUNG | OVARY | PROSTATE | NORMAL | |
|---|---|---|---|---|---|---|---|---|---|---|---|---|
| Antibody | Isotype | MB-231 | MB-468 | MCF-7 | HT-29 | SW1116 | SW620 | NCI H460 | OVCAR | PC-3 | CCD 27sk | Hs888 Lu |
| 1A245.6 | IgG1, k | + | + | + | ++ | + | + | + | + | + | + | + |
| anti-EGFR | IgG1, k | ++ | ++ | − | + | + | − | + | + | + | + | + |

TABLE 5

|  |  | Lung | | Colon | Prostate | Ovarian | Melanoma | | Breast | | Normal | |
|---|---|---|---|---|---|---|---|---|---|---|---|---|
|  |  |  |  |  |  |  |  |  |  |  | CCD | Hs888 |
| Antibody | Isotype | NCI H460 | A549 | HT-29 | PC-3 | OVCAR | A375 | A2058 | MB-231 | MB-468 | Hs578.Bst | 27sk | Lu |
| H460-22-1 | IgG1, k | + | + | + | + | + | + | + | + | + | + | + | + |
| anti-EGFR | IgG1, k | + | + | ++ | + | ++ | + | − | +++ | +++ | + | + | ++ |

EXAMPLE 5

Normal Human Tissue Staining

IHC studies were conducted to characterize the 7BD-33-11A, H460-22-1 and 1A245.6 antigen distribution in humans. These data have been discussed previously for 7BD-33-11A (Ser. No. 10/603,006, Ser. No. 10/810,751, the contents of each of which are herein incorporated by reference) and 1A245.6 (Ser. No. 10/603,006, the contents of which are herein incorporated by reference). IHC optimization studies were performed previously in order to determine the conditions for further experiments. 7BD-33-11A, H460-22-1 and 1A245.6 monoclonal antibodies were produced and purified as described above.

Tissue sections were deparaffinized by drying in an oven at 58° C. for 1 hour and dewaxed by immersing in xylene 5 times for 4 minutes each in Coplin jars. Following treatment through a series of graded ethanol washes (100%-75%) the sections were re-hydrated in water. The slides were immersed in 10 mM citrate buffer at pH 6 (Dako, Toronto, Ontario) then microwaved at high, medium, and low power settings for 5 minutes each and finally immersed in cold PBS. Slides were then immersed in 3% hydrogen peroxide solution for 6 minutes, washed with PBS three times for 5 minutes each, dried, incubated with Universal blocking solution (Dako, Toronto, Ontario) for 5 minutes at room temperature. 7BD-33-11A, 1A245.6, H460-22-1, monoclonal mouse anti-vimentin (Dako, Toronto, Ontario) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 µg/mL for each antibody) and incubated for 1 hour at room temperature. The slides were washed with PBS 3 times for 5 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehydrated with graded ethanols (75-100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a histopathologist.

Figure 15:
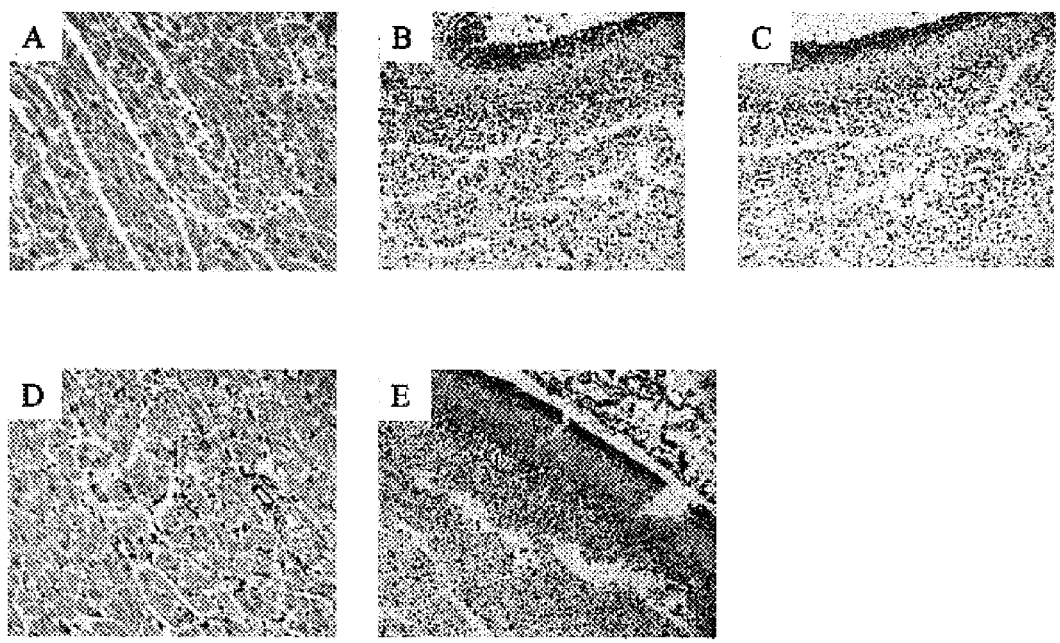
FIG. 15. Normal Human Heart. A. 7BD-33-11A. Normal Human Brain. B. 1A245.6. C. H460-22-1. Normal Human Heart. D. Positive control. Normal Human Brain. E. Positive control. Magnification is 200×.
Figure 16:
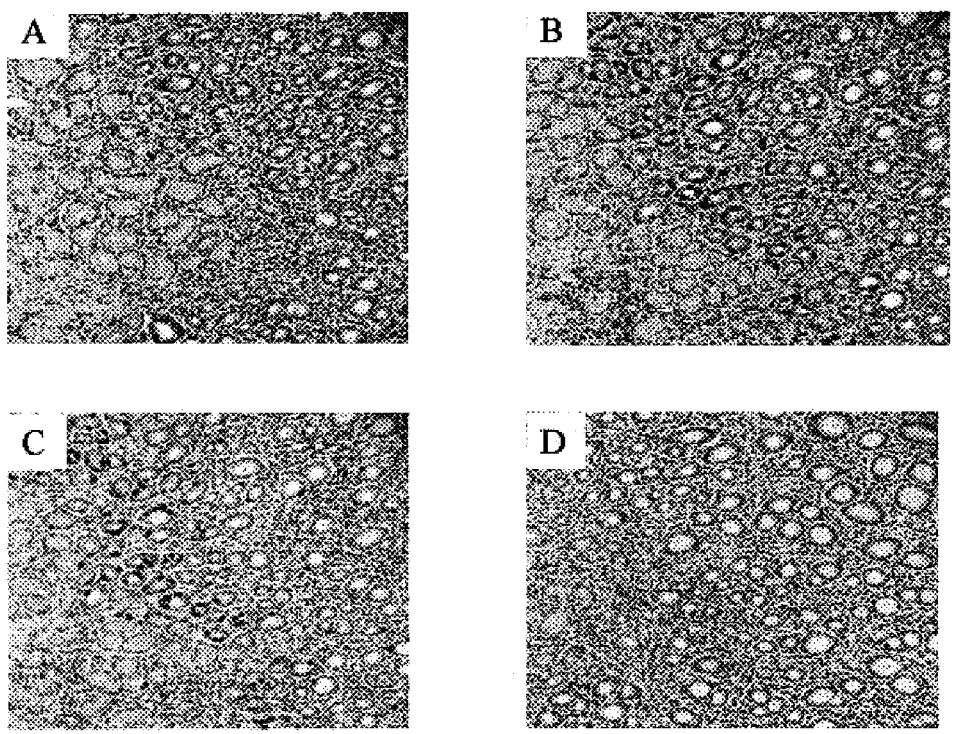
FIG. 16. Normal Human Stomach Antrum. A. 7BD-33-11A. B. H460-22-1. C. 1A245.6. D. Negative isotype control. Magnification is 200×.

Binding of antibodies to 59 normal human tissues was performed using a human, normal organ tissue array (Imgenex, San Diego, Calif.). Table 6 presents a summary of the results of 7BD-33-11A, H460-22-1 and 1A245.6 staining of an array of normal human tissues. From the table, there are 3 categories of tissue staining. A group of tissues was completely negative. These tissues included normal skin, brain, ovary, thymus, thyroid, small bowel, esophagus, heart (FIG. 15A), gall bladder and lymph node for 7BD-33-11A. For H460-22-1, the completely negative tissues were comprised of sub-cutaneous fat and brain (FIG. 15C). For 1A245.6, the completely negative tissues were comprised of skin, sub-cutaneous fat, esophagus and brain (FIG. 15B). A second group comprised tissues that demonstrated positive staining. These included the liver and pancreas for 7BD-33-11A. The tonsil had the strongest staining with this antibody. For H460-22-1, positive staining occurred in the liver, heart, testis, thyroid, adrenal gland and myometrium. Like H460-22-1, 1A245.6 positive staining occurred in the liver, heart, testis, thyroid, adrenal gland and myometrium. As with 7BD-33-11A, H460-22-1 and 1A245.6 stained the tonsil the strongest. A third group of tissues included tissues in which staining was positive in the tissue section, but was limited to infiltrating macrophages, lymphocytes, fibroblasts or the epithelium, for example the stomach for 7BD-33-11A, 1A245.6 and H460-22-1 (FIGS. 16A and B and C respectively). It should be noted that the 7BD-33-11A antigen is not present on cells of several of the vital organs, including kidney, heart (FIG. 15A) and lung. Overall, 7BD-33-11A binds to a smaller subset of normal human tissues compared to both H460-22-1 and 1A245.6 with weak to moderate binding in the tissues that are positive. H460-22-1 and 1A245.6 staining, albeit more extensive, is also generally weak to moderate in intensity. These results suggest that the antigen for 7BD-33-11A is not widely expressed on normal tissues, and that the antibody would bind specifically to a limited number of tissues in humans. In addition, the antigen for both H460-22-1 and 1A245.6, besides being present in the heart and liver, is limited to epithelium and infiltrating lymphocytes, macrophages and fibroblasts.

TABLE 6

IHC Summary of H460-22-1, 1A245.6 and 7BD-33-11A on a Normal Human Tissue Array

| Sec. No. | Organ | H460-22.1 | 1A245.6 | 7BD-33-11A | Vimentin |
|---|---|---|---|---|---|
| 1 | Skin* | +/− fibroblasts | − | − | +++ fibroblasts |
| 2 | Skin* | CS | − | − | +++ fibroblasts |
| 3 | Sub-cutis fat | − | − | − | ++ adipocytes |
| 4 | Breast | +/− fibroblasts | +/− fibroblasts | − | ++ endothelium & smooth muscle of blood vessels |
| 5 | Breast | +++ lobular epithelium | +++ lobular epithelium | +/− fibroblasts | ++ blood vessels & stroma |
| 6 | Speen | ++ lymphocytes | ++ lymphocytes | +/− lymphocytes | +++ sinusoidal endothelium & lymphocytes |
| 7 | Spleen | +++ lymphocytes | +++ lymphocytes | +/− lymphocytes | +++ sinusoidal endothelium & lymphocytes |

TABLE 6-continued

IHC Summary of H460-22-1, 1A245.6 and 7BD-33-11A on a Normal Human Tissue Array

| Sec. No. | Organ | H460-22.1 | 1A245.6 | 7BD-33-11A | Vimentin |
|---|---|---|---|---|---|
| 8 | Lymph node | ++ endothelium of blood vessels & lymphocytes | ++ endothelium of blood vessels & lymphocytes | – | +++ lymphocytes |
| 9 | Lymph node | + endothelium of blood vessels | + endothelium of blood vessels | – | ++ blood vessels & lymphocytes |
| 10 | Skeletal muscle | +/– endothelium of blood vessels | +/– endothelium of blood vessels | – | +/– blood vessels |
| 11 | Nasal Mucosa | — NR | — NR | — NR | — NR |
| 12 | Lung | +/– intestinal cells (marcrophages & fibroblasts) | +/– intestinal cells (marcrophages) | – | ++ alevolar epithelium & marcrophages |
| 13 | Lung | ++ bronchiolar epithelium, +++ macrophages | +/– bronchiolar epithelium, ++ macrophages | + macrophages | ++ alevolar epithelium, macrophages & lymphocytes |
| 14 | Bronchus | — NR | — NR | — NR | NR, ++ chondrocytes |
| 15 | Heart | ++ cardiac muscle | ++ cardiac muscle | –** | +++ blood vessels |
| 16 | Salivary gland | ++ acinar epithelium | ++ acinar epithelium | + acinar epithelium | +++ blood vessels & peripheral nerves |
| 17 | Liver | +++ hepatocytes | +++ hepatocytes | ++ hepatocytes | ++ blood vessels |
| 18 | Liver | +++ hepatocytes | +++ hepatocytes | + hepatocytes | +++ blood vessels & macrophages |
| 19 | Liver | ++ hepatocytes | + hepatocytes | +/– hepatocytes | +/– blood vessels |
| 20 | Gall bladder | ++ mucosal epithelium, fibroblasts & smooth muscle fibers | ++ mucosal epithelium, fibroblasts & smooth muscle fibers | – | +++ lymphocytes |
| 21 | Pancreas | +++ acinar epithelium & Islets of Langerhans | +++ acinar epithelium & Islets of Langerhans | + acinar epithelium | +++ acinar epithelium & blood vessels |
| 22 | Pancreas | +++ acinar epithelium & Islet of Langerhans | +++ acinar epithelium & Islet of Langerhans | ++ acinar epithelium | +++ acinar epithelium & blood vessels |
| 23 | Tonsil | +++ keratin, ++ lymphocytes | +++ keratin, + lymphocytes | +++ keratin, +/– lymphocytes | +++ lymphocytes |
| 24 | Esophagus | – | – | – | ++ blood vessels |
| 25 | Esophagus | +/– fibroblasts | – | – | +++ blood vessels |
| 26 | Stomach body*** | ++ gastric gland epithelium & lymphocytes in lamina propria | +/– gastric gland epithelium, ++ lymphocytes in lamina propria | ++ gastric gland epithelium | +++ blood vessels & fibroblasts |
| 27 | Stomach body*** | +++ gastric gland epithelium, ++ lymphocytes in lamina propria | +++ gastric gland epithelium, + lymphocytes in lamina propria | ++ gastric gland epithelium | +++ lymphocytes, blood vessels & fibroblasts |
| 28 | Stomach antrum | ++ gastric gland epithelium & lymphocytes in lamina propria | +/– gastric gland epithelium, + lymphocytes | ++ gastric gland epithelium | +++ lymphocytes |
| 29 | Stomach smooth muscle | – | – | – | +++ lymphocytes & blood vessels |
| 30 | Duodenum | ++ mucosal & glandular epithelium, +++ lymphocytes | +++ lymphocytes | + intestinal glands epithelium | ++ fibroblasts & blood vessels |
| 31 | Small bowel | +/– lymphocytes in lamina propria | +/– lymphocytes in lamina propria | – | + lymphocytes & blood vessels |
| 32 | Small bowel | +/– mucosal epithelium, ++ lymphocytes in lamina propria | +/– lymphocytes in lamina propria | – | +++ lymphocytes in lamina propria |
| 33 | Appendix | ++ mucosal epithelium, +++ lymphocytes | +++ mucosal epithelium & lymphocytes | ++ lymphocytes | +++ lymphocytes & blood vessels |
| 34 | Colon | + mucosal epithelium, ++ lymphocytes | +/– lymphocytes | +/– macrophages in lamina propria | ++ lymphocytes |
| 35 | Colon | ++ lymphocytes in lamina propria | + lymphocytes | – | ++ lymphocytes & blood vessels |
| 36 | Rectum | + mucosal epithelium & lymphocytes in lamina propria | +/– lymphocytes & blood vessels | – | ++ lymphocytes & blood vessels |
| 37 | Kidney cortex | ++ tubular epithelium | ++ tubular epithelium | – | +++ glomerular capillary & blood vessels |
| 38 | Kidney cortex | +++ tubular epithelium | +++ tubular epithelium | + tubular epithelium | +++ tubular epithelium, glomerular capillary & blood vessels |
| 39 | Kidney Medulla | + tubular epithelium & renal pelvis transitional epithelium | ++ tubular epithelium | – | ++ renal tubular epithelium, lipocytes & fibroblasts |
| 40 | Urinary Bladder | +++ transitional epithelium | ++ transitional epithelium | +/– transitional epithelium | ++ blood vessels |

TABLE 6-continued

IHC Summary of H460-22-1, 1A245.6 and 7BD-33-11A on a Normal Human Tissue Array

| Sec. No. | Organ | H460-22.1 | 1A245.6 | 7BD-33-11A | Vimentin |
|---|---|---|---|---|---|
| 41 | Prostate | +++ glandular epithelium | +++ glandular epithelium | ++ glandular epithelium | +++ glandular epithelium & blood vessels |
| 42 | Prostate | +++ glandular epithelium | +++ glandular epithelium | ++ glandular epithelium | +++ glandular epithelium & blood vessels |
| 43 | Seminal vesicle | + mucosal epithelium | + mucosal epithelium | +/− mucosal epithelium | +/− |
| 44 | Testis | ++ germinal epithelium, + Leydig cells | ++ germinal epithelium, + Leydig cells | +/− Leydig cells | +++ glandular epithelium |
| 45 | Endometrium profilarative | ++ glandular epithelium | +++ glandular epithelium, + stroma | − | +++ endometrial glands & stroma |
| 46 | Endometrium secretory | ++ glandular epithelium & stroma | ++ glandular epithelium & stroma | − | ++ glandular epithelium, +++ blood vessels |
| 47 | Myometrium | + smooth muscle fibers | + smooth muscle fibers | +/− fibroblasts | ++ smooth muscle fibers & blood vessels |
| 48 | Ulterine cervix | +/− fibroblasts | +/− fibroblasts | − | +++ fibroblasts |
| 49 | Salpinx | + endothelium of blood vessels, smooth muscle fibers & fibroblasts | + mucosal epithelium & blood vessels | − | +/− mucosal epithelium, +++ blood vessels |
| 50 | Ovary**** | ++ stromal cells | + stromal cells | − | +++ stromal cells |
| 51 | Placenta, villi | + trophoblasts | + trophoblasts | − | ++ blood vessels |
| 52 | Placenta, villi | ++ trophoblasts | ++ trophoblasts | − | ++ blood vessels |
| 53 | Umbilical cord | − | − | − | ++ fibroblasts |
| 54 | Adrenal gland | ++ endocrine cells | ++ endocrine cells | +/−** | +/−** |
| 55 | Thyroid | +/− follicular cells | +/− follicular cells | − | ++ follicular cells & blood vessels |
| 56 | Thymus | + lymphocytes | + lymphocytes | − | +++ lymphocytes |
| 57 | Brain white matter | − | − | − | ++ astrocytes |
| 58 | Brain gray matter | − | − | − | ++ blood vessels |
| 59 | Cerebellum | − | − | − | ++ cerebellar cortex |

Abbreviations:
NR: The section was not representative,
CS: The section was completely sloughed,
*The section was originally pigmented in the stratum basale,
**The section had endogenous cytoplasmic background staining,
***Stomach antrum (not stomach body),
****Ovarian stroma only.

As outlined and discussed in Ser. No. 10/810,751, the contents of which are herein incorporated by reference, studies compared 7BD-33-11A to two antibodies directed against CD63 (RFAC4 and H5C6) since the 7BD-33-11A antigen is CD63 as determined previously by biochemical methods. Binding of antibodies to 24 normal human tissues was performed using a human normal organ tissue array (Clinomics, Watervliet, N.Y.). All primary antibodies (7BD-33-11A; RFAC4 (Cymbus Biotechnology Ltd., Hants, UK) and H5C6 anti-CD63 (BD PharMingen, Oakville, ON); and mouse IgG$_1$ negative control (Dako, Toronto, ON)) were diluted in antibody dilution buffer (Dako, Toronto, ON) to a concentration of 5 μg/mL (found to be the optimal concentration in previous optimization steps). The negative control antibody has been shown to be negative to all mammalian tissues by the manufacturer. The procedure for IHC was as stated above.

Tissue sections were deparaffinized by drying in an oven at 58° C. for 1 hr and dewaxed by immersing in xylene 5 times for 4 min each in Coplin jars. Following treatment through a series of graded ethanol washes (100%-75%) the sections were re-hydrated in water. The slides were immersed in 10 mM citrate buffer at pH 6 (Dako, Toronto, Ontario) then microwaved at high, medium, and low power settings for 5 min each and finally immersed in cold PBS. Slides were then immersed in 3% hydrogen peroxide solution for 6 min, washed with PBS three times for 5 min each, dried, incubated with Universal blocking solution (Dako, Toronto, Ontario) for 5 min at room temperature. 7BD-33-11A, monoclonal mouse anti-CD63 (Cymbus Biotechnology Ltd., Hants, UK or Dako, Toronto, Ontario) or isotype control antibody (directed towards *Aspergillus niger* glucose oxidase, an enzyme which is neither present nor inducible in mammalian tissues; Dako, Toronto, Ontario) were diluted in antibody dilution buffer (Dako, Toronto, Ontario) to its working concentration (5 μg/mL for each antibody) and incubated for 1 hr at room temperature. The slides were washed with PBS 3 times for 5 minutes each. Immunoreactivity of the primary antibodies was detected/visualized with HRP conjugated secondary antibodies as supplied (Dako Envision System, Toronto, Ontario) for 30 minutes at room temperature. Following this step the slides were washed with PBS 3 times for 5 minutes each and a color reaction developed by adding DAB (3,3'-diaminobenzidine tetrahydrachloride, Dako, Toronto, Ontario) chromogen substrate solution for immunoperoxidase staining for 10 minutes at room temperature. Washing the slides in tap water terminated the chromogenic reaction. Following counterstaining with Meyer's Hematoxylin (Sigma Diagnostics, Oakville, ON), the slides were dehyrdated with graded ethanols (75-100%) and cleared with xylene. Using mounting media (Dako Faramount, Toronto, Ontario) the slides were coverslipped. Slides were microscopically examined using an Axiovert 200 (Zeiss Canada, Toronto, ON) and digital images acquired and stored using Northern Eclipse Imaging Software (Mississauga, ON). Results were read, scored and interpreted by a pathologist.

Table 7 presents a summary of the results of 7BD-33-11A and RFAC4 and H5C6 anti-CD63 staining of a test array of normal human tissues. The staining of tissues with 7BD-33-11A is similar to that described previously (Ser. No. 10/603,006, the contents of which are herein incorporated by reference). It should again be noted that 7BD-33-11A showed restricted binding to various cell types but had binding to infiltrating macrophages, lymphocytes, and fibroblasts. The RFAC4 and H5C6 antibodies showed a similar staining pattern in comparison to each other. However, the staining pattern of both RFAC4 and H5C6 was quite different than that observed with 7BD-33-11A. Specifically, both RFAC4 and H5C6 antibodies bound to a broader range of normal tissues, usually had higher staining intensity in tissues where 7BD-33-11A was also positive and bound not only to infiltrating macrophages, lymphocytes and fibroblasts and but to also to the epithelium in a majority of the tissues.

Tissues that were positive for 7BD-33-11A were also positive for either RFAC4 or H5C6 anti-CD63 antibodies. Tissues that were negative for 7BD-33-11A were generally not negative for the RFAC4 or H5C6. These results demonstrated that 7BD-33-11A bound to a smaller subset of the tissues recognized by either the RFAC4 or H5C6 anti-CD63 antibody and within tissues the intensity of staining was also sometimes less. These results showed that the epitope for 7BD-33-11A was not widely expressed on normal tissues, and that the antibody bound specifically to a limited number of tissues in humans. It also supported the biochemical evidence that 7BD-33-11A was directed against an epitope of CD63, albeit to a different epitope than the one recognized by either the RFAC4 or H5C6 antibodies used for these IHC studies.

TABLE 7

Comparison of RFAC4 and H5C6 anti-CD63 and 7BD-33-11A IHC on Human Normal Tissue

| Section | Tissue | 7BD-33-11A | RFAC4 | H5C6 |
|---|---|---|---|---|
| Aa3 | Breast | − | + (Ductular epithelium and stromal fibroblasts) | +++ (Ductular epithelium and stromal fibroblasts) |
| Aa4 | Breast | +/− (2–3 stromal fibroblasts) *No staining of ductular epithelium | +/− (Ductular epithelium and stromal fibroblasts) | +++ (Stromal fibroblasts) +/− (Ductular epithelium) |
| Ab3 | Lung | +++ (Macrophages and fibroblasts at interalveolar septum) | +++ (Macrophages and fibroblasts at interalveolar septum) | +++ (Alveolar epithelium and macrophages) |
| Ab4 | Lung | +++ (Macrophages and fibroblasts at interalveolar septum) | +++ (Macrophages and fibroblasts at interalveolar septum) | +++ (Macrophages and fibroblasts at interalveolar septum) |
| Ab5 | Lung | +/− (Macrophages and fibroblasts at interalveolar septum) | +++ (Macrophages and fibroblasts at interalveolar septum) | +++ (Macrophages and fibroblasts at interalveolar septum) |
| Ac1 | Colon | +++ (Lymphocytes and macrophages in lamina propria) *No staining of Mucosal epithelium | +++ (Mucosal epithelium, lymphocytes and macrophages at lamina propria) | +++ (Mucosal epithelium, lymphocytes and macrophages at lamina propria) |
| Ac3 | Colon | − | − | +/− (Lymphocytes at lamina propria) |
| Ac4 | Colon | +++ (Macrophages and fibroblasts at lamina propria) + (Mucosal epithelium) | +++ (Macrophages and fibroblasts at lamina propria) + (Mucosal epithelium) | +++ (Mucosal epithelium, lymphocytes and macrophages at lamina propria) |
| Ac5 | Colon | +/− (Macrophages and fibroblasts at lamina propria) | +++ (Macrophages and fibroblasts at lamina propria) + (Mucosal epithelium) | +++ (Lymphocytes and macrophages in lamina propria) |
| Ad1 | Prostate | +++ (Glandular epithelium) | +++ (Glandular epithelium) | +++ (Glandular epithelium) |
| Ad2 | Prostate | +++ (Glandular epithelium) | +++ (Glandular epithelium) | +++ (Glandular epithelium) |
| Ad4 | Prostate | ++ (Glandular epithelium) |  | +++ (Glandular epithelium) |
| Ad5 | Prostate | +++ (Glandular epithelium) | +++ (Glandular epithelium) | +++ (Glandular epithelium) |
| Ae1 | Kidney | − | + (Tubular epithelium) | ++ (Tubular epithelium) |
| Ae2 | Kidney | +/− (2–3 interstitial cells) *No staining of tubular epithelium | ++ (Tubular epithelium) | ++ (Tubular epithelium) |
| Ae3 | Kidney | +/− (2–3 interstitial cells) | ++ (Tubular epithelium) | ++ (Tubular epithelium) |
| Ae4 | Liver | ++ (Hepatocytes and sinusoidal staining) | +++ (Hepatocytes & sinusoidal staining and bile duct epithelium) | +++ (Hepatocytes, sinusoidal staining and bile ducts) |
| Af1 | Liver | − | ++ (Sinusoidal and bile duct epithelium) | ++ (Sinusoidal and bile duct epithelium) |
| Af2 | Liver | − | +/− (Hepatocytes and sinusoidal staining) | +/− (Hepatocytes and sinusoidal staining) |
| Af3 | Lymph node | − | ++ (Reticular cells) | ++ (Reticular cells) |
| Ag1 | Thyroid | − | +/− (Follicular cells) | +/− (Follicular cells) |
| Ag2 | Thyroid | +++ (Follicular cells) | +++ (Follicular cells) | +++ (Follicular cells) |
| Ah1 | Placenta | − | +++ (Syncytiotrophoblasts & basement membrane of chorionic villi) | +++ (Syncytiotrophoblasts & basement membrane of chorionic villi) |
| Ah2 | Placenta | − | +++ (Syncytiotrophoblasts & basement membrane of chorionic villi) | +++ (Syncytiotrophoblasts & basement membrane of chorionic villi) |

EXAMPLE 6

Human Breast Tumor Tissue Staining

As partially outlined and discussed in Ser. No. 10/603,006 and Ser. No. 10/810,751, the contents of each of which are herein incorporated by reference, IHC studies were undertaken to determine the cancer association of the 7BD-33-11A, H460-22-1 and 1A245.6 antigen with human breast cancers and whether the antibodies were likely to recognize human cancers. A comparison was made with vimentin (positive control) and an antibody against *Aspergillus niger* glucose oxidase, an enzyme which is neither present nor inducible in mammalian tissues (negative control). A breast cancer tissue array derived from 50 breast cancer patients and 10 samples derived from non-neoplastic breast tissue in breast cancer patients (Imgenex Corporation, San Diego, Calif.) was stained with all 3 antibodies. Age, sex, and diagnosis were provided for each patient. The procedure for IHC from Example 5 was followed. All antibodies were used at a working concentration of 5 μg/mL. Table 8a provides a summary of 7BD-33-11A, H460-22-1 and 1A245.6 antibody staining of this array.

Figure 17:
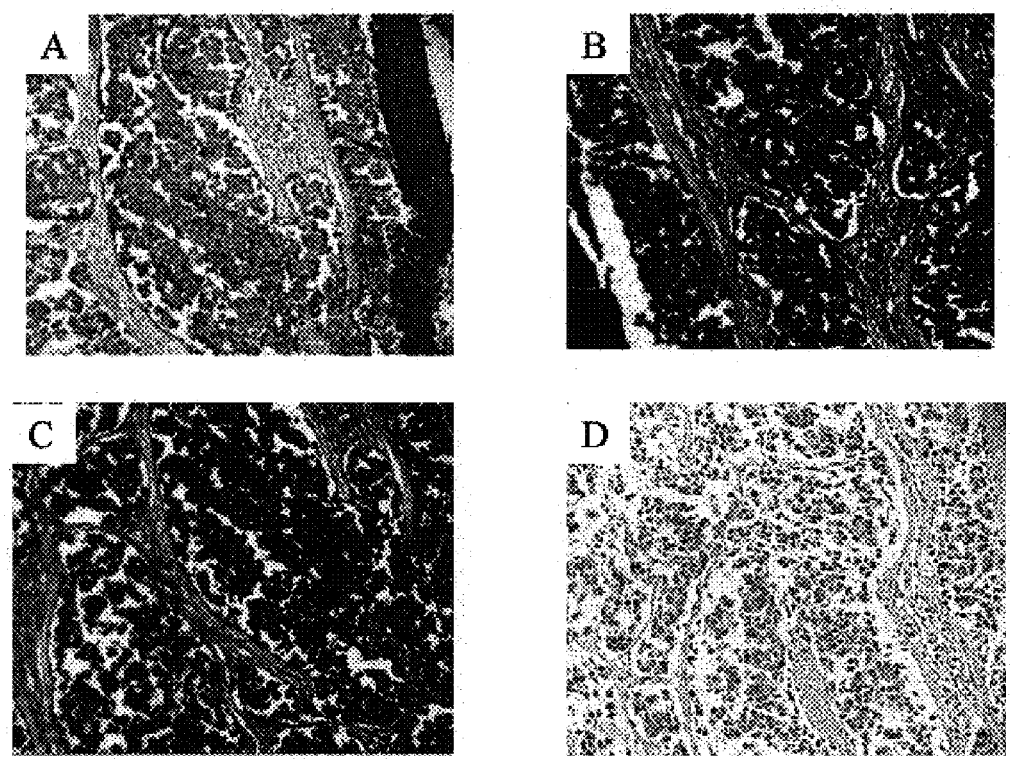
FIG. 17. Representative micrograph of A. 7BD-33-11A, B. 1A245.6 and C. H460-22-1 binding to human breast cancer tumor (infiltrating duct carcinoma). D. Negative Isotype Control. Magnification is 200×.
Figure 18:
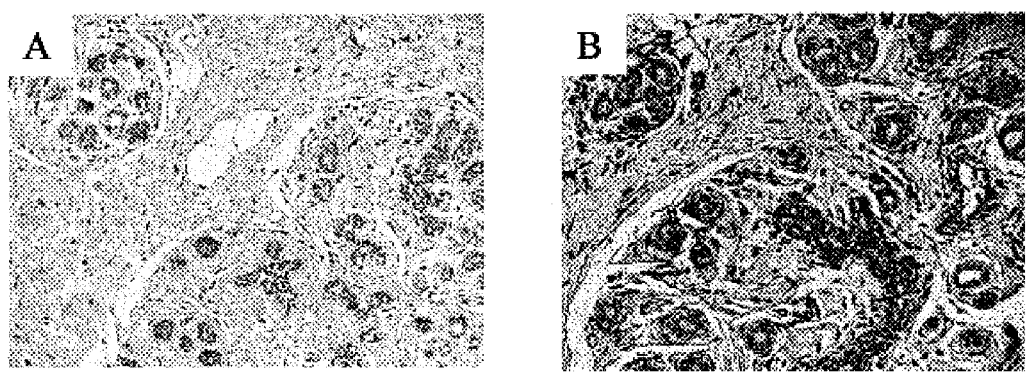
FIG. 18. Representative micrograph of A. 7BD-33-11A, B. Positive control binding to human normal breast tissue. Magnification is 200×.

An additional 48 breast cancer (Imgenex Corporation) and 9 normal breast tissue samples were tested with 7BD-33-11A (shown in Table 8b). Pooled results from all 98 sections stained with 7BD-33-11A are referenced in Table 11. Overall, 37 percent of the 98 patients tested were positive for the 7BD-33-11A antigen (FIG. 17A) compared to 92 percent and 98 percent of 50 patients tested for H460-22-1 and 1A245.6 respectively (FIGS. 17C and B respectively). For 7BD-33-11A, 0 out of 19 normal breast tissue samples from breast cancer patients were positive (FIG. 18A). Conversely, 9 out of 10 normal breast tissue samples were positive for both H460-22-1 and 1A245.6. However, staining was due to infiltrating fibroblasts in the majority of cases (FIGS. 18C and B respectively). As shown in Table 11, there is a trend of higher binding of 7BD-33-11A to estrogen receptor negative breast cancers, progesterone positive breast cancers and advanced breast cancers (T3 & T4).

No correlation between estrogen and progesterone receptor status was evident for 1A245.6 but the intensity of tissue staining did appear to correlate with higher tumor stage (Table 9). A slightly higher number of tissues positive for H460-22-1 were also estrogen and progesterone receptor positive and there was a trend to greater positive expression with higher tumor stage (Table 10). The 7BD-33-11A, H460-22-1 and 1A2425.6 staining was specific for cancerous cells and staining occurred on both the membrane and within the cytoplasm. The staining pattern, from 7BD-33-11A, H460-22-1 and 1A245.6, showed that in patient samples, the antibody is highly specific for malignant cells and the respective antigens are present on the cell membrane thereby making it an attractive drugable target.

TABLE 8a

IHC Summary for H460-22-1, 1A245.6 and 7BD-33-11A on 50 Human Breast Tumor and 10 Normal Tissue Sections

| Sec. No. | Age | Sex | Diagnosis | H460-22-1 | 1A245.6 | 7BD-33-11A | Vimentin |
|---|---|---|---|---|---|---|---|
| 1 | F | 28 | Infiltrating duct carcinoma | ++ MC | +++ MC | ++ MC | − tumor, +++ stroma |
| 2 | F | 71 | Solid papillary carcinoma | +++ MC | +++ MC | +/− | +/− tumor, +++ stroma |
| 3 | F | 26 | Infiltrating duct carcinoma | + MC | ++ MC | − | +/− tumor, +++ stroma |
| 4 | F | 43 | Infiltrating duct carcinoma | ++ MC | ++ MC | +/− | − tumor, +++ stroma |
| 5 | F | 39 | Infiltrating duct carcinoma | +/− tumor, +++ necrotic area | + MC tumor, +++ necrotic area | +/− | ++ MC tumor, +++ stroma |
| 6 | F | 46 | Ductal carcinoma in situ | ++ MC | ++ MC | +/− | +/− tumor, + blood vessels |
| 7 | F | 47 | Infiltrating duct carcinoma | +++ MC | +++ MC tumor, ++ stroma | + MC | +/− tumor, +++ stroma |
| 8 | M | 67 | Infiltrating duct carcinoma | ++ MC | +++ MC | + MC | − tumor, +++ stroma |
| 9 | F | 33 | Infiltrating duct carcinoma | + MC | ++ MC | − | +/− tumor, ++ stroma |
| 10 | F | 47 | Infiltrating duct carcinoma | ++ MC | ++ MC | − | +/− tumor, +++ stroma |
| 11 | F | 49 | Invasive Lobular carcinoma | − | − tumor, +/− fibroblasts | − | − tumor, +++ blood vessels & lymphocytes |
| 12 | F | 46 | Infiltrating duct carcinoma | ++ MC | +++ MC | − | +/− tumor, +++ blood vessels & lymphocytes |
| 13 | F | 39 | Infiltrating duct carcinoma | ++ MC | ++ MC | − | +++ M tumor & stroma |
| 14 | F | 43 | Infiltrating lobular carcinoma | +++ MC | +++ MC | +/− | − tumor, +++ stroma |
| 15 | F | 54 | Infiltrating lobular carcinoma | ++ MC | ++ MC | +/− | − tumor, +++ blood vessels |
| 16 | F | 58 | Infiltrating duct carcinoma | ++ MC tumor & stroma, +++ necrotic area | ++ MC tumor & stroma, +++ necrotic area | +/− | ++ MC tumor, +++ stroma |
| 17 | F | 37 | Infiltrating duct carcinoma | ++ MC | +++ MC | − | − tumor, +++ stroma |
| 18 | F | 43 | Infiltrating duct carcinoma | +++ MC tumor & stroma | +++ MC tumor & stroma | +++ M/C | +++ MC tumor & stroma |
| 19 | F | 51 | Infiltrating duct carcinoma | ++ MC | +++ MC | + MC | +++ MC tumor & stroma |
| 20 | F | 80 | Modullary carcinoma | ++ MC | ++ MC | − | ++ MC tumor, +++ stroma |
| 21 | F | 36 | Infiltrating duct carcinoma | ++ MC tumor & lymphocytes | ++ MC tumor & stroma | − | +++ MC tumor & stroma |
| 22 | F | 59 | Infiltrating duct carcinoma | + MC | + MC | +/− blood vessels | ++ MC tumor |
| 23 | F | 34 | Ductal carcinoma in situ | ++ MC tumor & stroma, +++ necrotic area | ++ MC & stroma, +++ necrotic area | + tumor, ++ tumor nerotic area | +/− tumor, +++ blood vessels |
| 24 | F | 54 | Infiltrating duct carcinoma | + MC | ++ MC | +/− | − tumor, +++ stroma |
| 25 | F | 47 | Infiltrating duct carcinoma | +++ MC | +++ MC | ++ MC | +++ MC |
| 26 | F | 53 | Infiltrating duct carcinoma | +++ MC tumor & stroma | ++ MC | − | − tumor, +++ stroma |

TABLE 8a-continued

IHC Summary for H460-22-1, 1A245.6 and 7BD-33-11A on 50 Human Breast Tumor and 10 Normal Tissue Sections

| Sec. No. | Age | Sex | Diagnosis | H460-22-1 | 1A245.6 | 7BD-33-11A | Vimentin |
|---|---|---|---|---|---|---|---|
| 27 | F | 59 | Infiltrating duct carcinoma | + MC tumor, +++ necroticarea | + MC tumor, stroma & endothelium of blood vessels | +/− necrotic area | − tumor, +++ stroma |
| 28 | F | 60 | Signet ring cell carcinoma | ++ MC | +++ MC | − | − tumor, +++ stroma |
| 29 | F | 37 | Infiltrating duct carcinoma | +++ MC | +++ MC | ++ MC | ++ MC tumor, +++ stroma |
| 30 | F | 46 | Infiltrating duct carcinoma | ++ MC | ++ MC | +/− | +++ MC tumor & stroma |
| 31 | F | 35 | Infiltrating duct carcinoma | +/− | +/− | − | + tumor, +++ stroma |
| 32 | F | 47 | Infiltrating duct carcinoma | − tumor, ++ necrotic area | + tumor, +++ necrotic area | − | +++ MC |
| 33 | F | 54 | Infiltrating duct carcinoma | + MC | ++ MC | − | − tumor, +++ stroma |
| 34 | F | 47 | Infiltrating duct carcinoma | + MC tumor & stroma | + MC tumor & stroma | − | − tumor, +++ stroma |
| 35 | F | 41 | Infiltrating duct carcinoma | ++ MC | +++ MC | − | +/− tumor, +++ stroma |
| 36 | F | 38 | Infiltrating duct carcinoma | +++ MC | +++ MC | − | − tumor, +++ stroma |
| 37 | F | 55 | Infiltrating duct carcinoma | + MC tumor & stroma | + MC tumor & stroma | − | − tumor, +++ stroma |
| 38 | F | 65 | Infiltrating duct carcinoma | +/− | ++ MC tumor & stroma | − | − tumor, +++ stroma |
| 39 | M | 66 | Infiltrating duct carcinoma | + MC tumor & stroma | + MC tumor & stroma | − | − tumor, +++ stroma |
| 40 | F | 44 | Infiltrating duct carcinoma | ++ MC | ++ MC | − | +++ MC |
| 41 | F | 52 | Metastatic carcinoma in Lymph node | ++ MC | ++ MC | − | +++ MC |
| 42 | F | 32 | Metastatic carcinoma in Lymph node | + MC | ++ MC | − | − tumor, +++ stroma |
| 43 | F | 58 | Metastatic carcinoma in Lymph node | ++ MC | +++ MC | +/− | − tumor, +++ stroma |
| 44 | F | 52 | Metastatic carcinoma in Lymph node | ++ MC | ++ MC | − | +++ MC |
| 45 | F | 58 | Metastatic carcinoma in Lymph node | − tumor, ++ stroma | + MC | − | +++ MC |
| 46 | F | 38 | Metastatic carcinoma in Lymph node | ++ MC | +++ MC | − | +++ MC |
| 47 | F | 45 | Metastatic carcinoma in Lymph node | − | +/− | − | +++ MC |
| 48 | F | 45 | Metastatic carcinoma in Lymph node | ++ MC | ++ MC | − | − tumor, +++ stroma |
| 49 | F | 29 | Metastatic carcinoma in Lymph node | + MC | ++ MC | − | − tumor, +++ stroma |
| 50 | F | 61 | Metastatic carcinoma in Lymph node | + MC tumor & stroma | ++ MC | − | + tumor, +++ stroma |
| 51* | F | 46 | Nipple | ++ sebaceous glands | ++ sebaceous glands | − | +++ fibroblasts, lymphocytes & macrophages |
| 52* | F | 47 | Nipple | ++ MC | ++ MC | − | +++ fibroblasts, lymphocytes & macrophages |
| 53* | F | 40 | Normal Breast | − | − | − | +++ blood vessels, myo-epithelium, fibroblasts, & lipocytes |
| 54* | F | 43 | Normal Breast | +/− fibroblasts | +/− fibroblasts | − | +++ blood vessels, myo-epithelium, fibroblasts, & lipocytes |
| 55* | F | 40 | Normal Breast | ++ lobular epithelium, fibrobasts & endothelium | ++ lobular epithelium, fibrobasts & endothelium | − | +++ lobular epithelium, myo-epithelium fibroblasts |
| 56* | F | 40 | Normal Breast | +/− fibroblasts | +/− fibroblasts | − | +++ blood vessels, Myo-epithelium, Fibroblasts, & Lipocytes |
| 57* | F | 45 | Normal Breast | +/− fibroblasts | +/− fibroblasts | − | ++ Blood vessels, Fibroblasts, & lymphocytes |
| 58* | F | 44 | Normal Breast | +/− fibroblasts | +/− fibroblasts | − | +/− lobular epithelium, +++ myo-epithelium, blood vessels & fibroblasts |
| 59* | F | 37 | Normal Breast | +/− fibroblasts | ++ lobular epithelium & fibroblasts | − | +++ lobular epithelium, myo-epithelium fibroblasts & lymphocytes |
| 60 | F | 51 | Normal Breast | +/− fibroblasts | +/− fibroblasts | − | +/− lobular epithelium, +++ blood vessels |

Abbreviations:
M: Mitochondrial staining,
C: Cytoplasmic staining.

TABLE 8b

IHC Summary for 7BD-33-11A 48 Human Breast Tumor and 9 Normal Tissue Sections

| Sec. No. | Sex/Age | Diagnosis | T stage | ER | PR | AR7BD-33-11A |
|---|---|---|---|---|---|---|
| 1 | F/65 | Infiltrating ductal ca | T2 | + | + | − |
| 2 | F/34 | Infiltrating ductal ca | T1 | + | − | − |
| 3 | F/39 | Infiltrating ductal ca | T2 | − | + | +/− Tumor cells |
| 4 | F/38 | Infiltrating ductal ca | T2 | + | + | +/− Tumor cells |
| 5 | F/67 | infiltrating lobular ca | T3 | + | − | − |
| 6 | F/45 | Infiltrating ductal ca | T2 | − | − | − |
| 7 | F/50 | Infiltrating ductal ca | T2 | + | − | − |
| 8 | F/54 | Infiltrating ductal ca | T2 | − | − | − |
| 9 | F/37 | Infiltrating ductal ca | T2 | − | − | − |
| 10 | F/52 | Infiltrating ductal ca | T2 | + | − | − |
| 11 | F/84 | Infiltrating ductal ca | T3 | − | − | + Tumor cells<br>+++ necrotic area |
| 12 | F/40 | Infiltrating ductal ca | T2 | − | − | − Tumor cells<br>++ Infiltrating inflammatory cells |
| 13 | F/64 | Infiltrating ductal ca | T2 | − | − | + Tumor cells |
| 14 | F/61 | Infiltrating ductal ca | T4 | + | − | − |
| 15 | F/35 | Infiltrating ductal ca | T1 | − | − | + Tumor cells |
| 16 | F/66 | Infiltrating ductal ca | T2 | − | − | − Tumor cells<br>+/− Stroma |
| 17 | F/58 | Infiltrating ductal ca | T3 | − | − | − |
| 18 | F/49 | Infiltrating ductal ca | T3 | − | − | +/− Tumor cells<br>+++ stroma |
| 19 | F/75 | Infiltrating ductal ca | T1 | + | + | − |
| 20 | F/44 | infiltrating lobular ca | T2 | + | + | ++ Tumor cells |
| 21 | F/40 | Infiltrating ductal ca | T2 | − | − | − |
| 22 | F/49 | Medullary ca | T2 | − | − | − |
| 23 | F/50 | Infiltrating ductal ca | T2 | − | + | − |
| 24 | F/71 | Infiltrating ductal ca | T3 | − | − | − |
| 25 | F/50 | Infiltrating ductal ca | T3 | − | − | + Tumor cells |
| 26 | F/42 | Infiltrating ductal ca | T3 | − | − | +/− Tumor cells |
| 27 | F/64 | Infiltrating ductal ca | T1 | + | + | − |
| 28 | F/32 | Infiltrating ductal ca | T3 | − | − | + Tumor cells |
| 29 | F/60 | Infiltrating ductal ca | T2 | − | − | +/− Tumor cells |
| 30 | F/53 | Infiltrating ductal ca | T2 | + | − | − Tumor cells<br>++ Stroma |
| 31 | F/73 | Infiltrating ductal ca | T2 | − | − | − Tumor cells<br>+/− Infiltrating lymphocytes |
| 32 | F/50 | Infiltrating ductal ca | T3 | − | − | − |
| 33 | F/46 | Infiltrating ductal ca | T3 | − | − | − Tumor cells<br>+/− Necrotic area |
| 34 | F/51 | Infiltrating ductal ca | T2 | − | − | − |
| 35 | F/59 | Infiltrating ductal ca | T1 | + | − | + Tumor cells |
| 36 | F/36 | Infiltrating ductal ca | T2 | + | − | − |
| 37 | F/53 | Infiltrating ductal ca | T3 | − | − | + Tumor cells |
| 38 | F/69 | Infiltrating ductal ca | T2 | − | − | +++ Tumor cells |
| 39 | F/34 | Infiltrating ductal ca | T2 | − | − | +++ Tumor cells |
| 40 | F/36 | Infiltrating ductal ca | T3 | + | + | +/− Tumor cells & stroma |
| 41 | F/60 | Infiltrating ductal ca | T3 | − | − | +/− Tumor cells & stroma |
| 42 | F/49 | Infiltrating ductal ca | T3 | + | + | +/− Tumor cells & stroma |
| 43 | F/48 | Infiltrating ductal ca | T3 | + | − | − Tumor cells<br>+/− Stroma |
| 44 | F/36 | Infiltrating ductal ca | T2 | − | − | − Tumor cells<br>++ Stroma & infiltrating Lymphocytes |
| 45 | F/34 | Infiltrating ductal ca | T1 | + | − | − Tumor cells<br>+++ Stroma & infiltrating inflammatory cells |
| 46 | F/54 | Infiltrating ductal ca | T3 | + | + | − Tumor cells<br>++ Stroma & infiltrating inflammatory cells |
| 47 | F/41 | Infiltrating ductal ca | T1 | + | + | − Tumor cells<br>+/− Stroma |
| 48 | F/67 | Infiltrating ductal ca | T2 | + | − | − |
| 49 | F/42 | Non Neoplastic Breast | | | | − |
| 50 | F/31 | Non Neoplastic Breast | | | | − |
| 51 | F/47 | Non Neoplastic Breast | | | | − |
| 52 | F/43 | Non Neoplastic Breast | | | | − |
| 53 | F/42 | Non Neoplastic Breast | | | | − |
| 54 | F/40 | Non Neoplastic Breast | | | | − |

TABLE 8b-continued

IHC Summary for 7BD-33-11A 48 Human Breast Tumor and 9 Normal Tissue Sections

| Sec. No. | Sex/Age | Diagnosis | T stage | ER | PR | AR | 7BD-33-11A |
|---|---|---|---|---|---|---|---|
| 55 | F/35 | Non Neoplastic Breast | | | | | − |
| 56 | F/50 | Non Neoplastic Breast | | | | | − |
| 57 | F/41 | Non Neoplastic Breast | | | | | − |

TABLE 9

Human Breast Tumor IHC Summary for 1A245.6

| | | | | Binding Score | | | | | |
|---|---|---|---|---|---|---|---|---|---|
| | | Total # | − | +/− | + | ++ | +++ | Total positive | % positive of total |
| PatientSamples | Tumor | 50 | 1 | 2 | 8 | 23 | 16 | 49 | 98% |
| | Normal | 10 | 1 | 5(Fibroblasts) | 0 | 4 | 0 | 9 | 90% |
| ER Status | ER+ | 28 | 0 | 1 | 2 | 14 | 11 | 28 | 100% |
| | ER− | 22 | 1 | 1 | 6 | 9 | 5 | 21 | 96% |
| | Unknown | 0 | 0 | 0 | 0 | 0 | 0 | 0 | 0% |
| PR Status | PR+ | 19 | 0 | 0 | 1 | 8 | 10 | 19 | 100% |
| | PR− | 30 | 1 | 2 | 7 | 14 | 6 | 29 | 97% |
| | Unknown | 1 | 0 | 0 | 0 | 0 | 0 | 1 | 100% |
| AJCCTumorStage | T1 | 4 | 0 | 1 | 1 | 1 | 1 | 4 | 100% |
| | T2 | 21 | 1 | 0 | 6 | 9 | 5 | 20 | 95% |
| | T3 | 20 | 0 | 1 | 1 | 10 | 8 | 20 | 100% |
| | T4 | 5 | 0 | 0 | 0 | 3 | 2 | 5 | 100% |

TABLE 10

Human Breast Tumor IHC Summary for H460-22-1

| | | | | Binding Score | | | | | |
|---|---|---|---|---|---|---|---|---|---|
| | | Total # | − | +/− | + | ++ | +++ | Total positive | % positive of total |
| Patient Samples | Tumor | 50 | 4 | 3 | 12 | 23 | 8 | 46 | 92% |
| | Normal | 10 | 1 | 6 | 0 | 3 | 0 | 9 | 90% |
| ER Status | ER+ | 28 | 0 | 2 | 7 | 17 | 2 | 28 | 100% |
| | ER− | 22 | 4 | 1 | 5 | 6 | 6 | 18 | 82% |
| | Unknown | 0 | 0 | 0 | 0 | 0 | 0 | 0 | 0% |
| PR Status | PR+ | 19 | 0 | 0 | 5 | 11 | 3 | 19 | 100% |
| | PR− | 30 | 4 | 3 | 7 | 11 | 5 | 26 | 87% |
| | Unknown | 1 | 0 | 0 | 0 | 1 | 0 | 1 | 100% |
| AJCC Tumor Stage | T1 | 4 | 1 | 0 | 2 | 1 | 0 | 3 | 75% |
| | T2 | 21 | 4 | 0 | 6 | 7 | 4 | 17 | 81% |
| | T3 | 20 | 0 | 2 | 3 | 12 | 3 | 20 | 100% |
| | T4 | 5 | 0 | 0 | 1 | 3 | 2 | 5 | 100% |

TABLE 11

Human Breast Tumor IHC Summary for 7BD-33-11A

| | | | | Binding Score | | | | | |
|---|---|---|---|---|---|---|---|---|---|
| | | Total # | − | +/− | + | ++ | +++ | Total positive | % of Positive |
| Patients' samples | Tumor | 98 | 62 | 18 | 11 | 4 | 3 | 36 | 37% |
| | Normal | 19 | 20 | 0 | 0 | 0 | 0 | 0 | 0% |
| ER Status | ER+ | 48 | 32 | 10 | 3 | 3 | 0 | 16 | 33% |
| | ER− | 50 | 30 | 8 | 8 | 1 | 3 | 20 | 40% |
| PR Status | PR+ | 30 | 16 | 9 | 2 | 3 | 0 | 14 | 47% |
| | PR− | 67 | 45 | 9 | 9 | 1 | 3 | 22 | 33% |
| | Unknown | 1 | 1 | 0 | 0 | 0 | 0 | 0 | 0% |
| AJCC Tumor stage | T1 | 11 | 9 | 0 | 2 | 0 | 0 | 2 | 18% |
| | T2 | 45 | 33 | 4 | 3 | 2 | 3 | 12 | 27% |
| | T3 | 36 | 18 | 11 | 6 | 1 | 0 | 18 | 50% |
| | T4 | 6 | 2 | 3 | 0 | 1 | 0 | 4 | 67% |

As outlined and discussed in Ser. No. 10/810,751, the contents of which are herein incorporated by reference, a comparison was carried out using 7BD-33-11A and RFAC4 and H5C6 anti-CD63 and c-erbB-2 anti-Her2 (A0485, Dako-Cytomation, Mississagua, ON) antibodies. A breast cancer tissue array derived from 50 breast cancer patients and 10 samples derived from non-neoplastic breast tissue in breast cancer patients was used (Imgenex Corporation, San Diego, Calif.). The following information was provided for each patient: age, sex, American Joint Committee on Cancer (AJCC) tumor stage, lymph node, estrogen receptor (ER) and projesterone receptor (PR) status. The procedure for IHC from Example 5 was followed. All antibodies were used at a working concentration of 5 μg/mL except for the anti-Her2 antibody where a concentration of 1.5 μg/mL was used.

Figure 19:
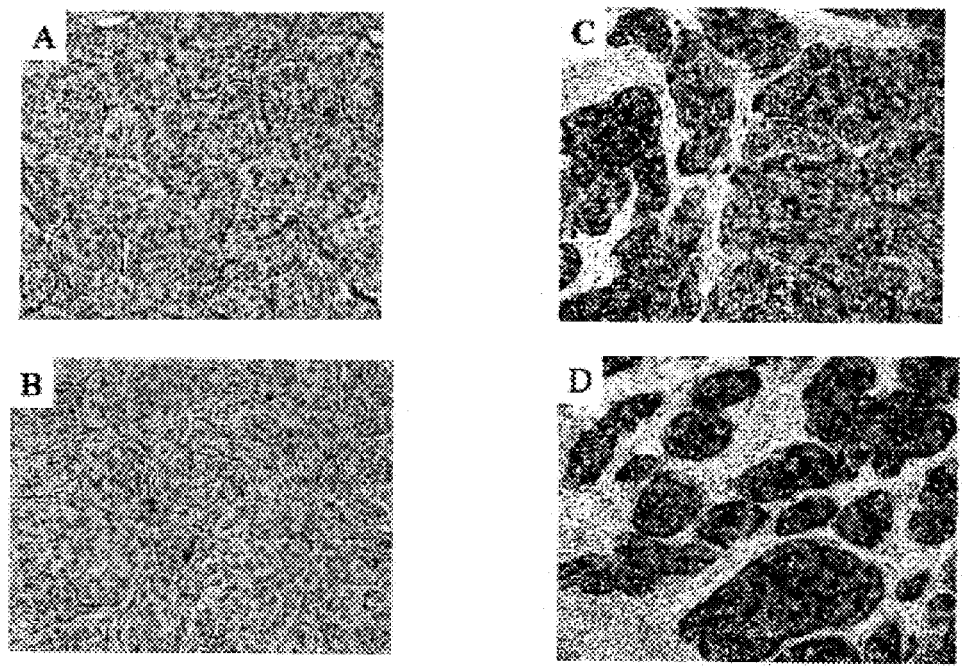
FIG. 19. Representative micrographs showing the binding pattern obtained with 7BD-33-11A (A), isotype negative control (B), anti-CD63 (RFAC4) antibody or the anti-CD63 (H5C6) antibody (D) on tissue sections of infiltrative ductal carcinoma from a human breast cancer tissue array. 7BD-33-11A displayed weaker positive staining for the tumor cells in comparison to either RFAC4 or H5C6 antibody. Magnification is 200×.

Tables 11, 12, 13 and 14 provide summaries of 7BD-33-11A, RFAC4 and H5C6 anti-CD63 antibody staining of breast cancer tissue arrays respectively. Overall, 36 percent of the 50 patients tested were positive for 7BD-33-11A antigen compared to 85 and 94 percent for RFAC4 and H5C6 anti-CD63 antibodies respectively. In cases where both 7BD-33-11A and RFAC4 or H5C6 anti-CD63 antibodies stained the same tissue, 97 percent of the samples had higher intensity staining with both the RFAC4 and H5C6 anti-CD63 in comparison to 7BD-33-11A (FIG. 19). For 7BD-33-11A, 0 out of 10 normal breast tissue samples from breast cancer patients were positive. For both RFAC4 and H5C6 anti-CD63 antigen, 7 out of 8 normal breast tissue samples from breast cancer patients were positive (2 samples were not representative). As mentioned above, there was a slight correlation between estrogen or progesterone receptor expression and expression of 7BD-33-11A antigen; tissues with either receptor expression had slightly higher 7BD-33-11A antigen expression. When tumors were analyzed based on their stage, or degree to which the cancer advanced, results suggested a trend towards greater positive expression with higher tumor stage for 7BD-33-11A. Similar results were obtained with RFAC4. H5C6 also showed a very slight correlation with estrogen or progesterone receptor expression but there was no apparent correlation with tumor stage. However, for all three antibodies, the results were limited by the small sample size.

TABLE 12

Human Breast Tumor IHC Summary for RFAC4

| | | Total # | − | +/− | + | ++ | +++ | Total positive | % positive of total |
|---|---|---|---|---|---|---|---|---|---|
| Patient Samples | Tumor | 47 | 7 | 3 | 7 | 16 | 14 | 40 | 85% |
| | Normal | 8 | 1 | 1 | 0 | 2 | 4 | 7 | 87.50% |
| ER Status | ER+ | 27 | 1 | 2 | 3 | 15 | 6 | 26 | 96% |
| | ER− | 20 | 6 | 1 | 3 | 4 | 6 | 14 | 70% |
| | Unknown | 0 | 0 | 0 | 0 | 0 | 0 | 0 | 0% |
| PR Status | PR+ | 18 | 0 | 1 | 2 | 9 | 6 | 18 | 100% |
| | PR− | 28 | 7 | 2 | 4 | 9 | 6 | 21 | 75% |
| | Unknown | 1 | 0 | 0 | 0 | 1 | 0 | 1 | 100% |
| AJCC Tumor Stage | T1 | 4 | 2 | 0 | 1 | 1 | 0 | 2 | 50% |
| | T2 | 20 | 4 | 2 | 3 | 6 | 5 | 16 | 80% |
| | T3 | 18 | 1 | 1 | 2 | 7 | 7 | 17 | 94% |
| | T4 | 5 | 0 | 0 | 1 | 2 | 2 | 5 | 100% |

Binding Score columns: −, +/−, +, ++, +++

TABLE 13

Human Breast Tumor IHC Summary for H5C6

| | | Total # | − | +/− | + | ++ | +++ | Total positive | % positive of total |
|---|---|---|---|---|---|---|---|---|---|
| Patient Samples | Tumor | 47 | 3 | 4 | 8 | 15 | 17 | 44 | 94% |
| | Normal | 8 | 1 | 1 | 0 | 2 | 4 | 7 | 87.50% |
| ER Status | ER+ | 27 | 1 | 1 | 6 | 8 | 11 | 26 | 96% |
| | ER− | 20 | 2 | 3 | 2 | 8 | 5 | 18 | 90% |
| | Unknown | 0 | 0 | 0 | 0 | 0 | 0 | 0 | 0% |
| PR Status | PR+ | 18 | 0 | 0 | 4 | 4 | 10 | 18 | 100% |
| | PR− | 28 | 3 | 4 | 4 | 11 | 6 | 25 | 89% |
| | Unknown | 1 | 0 | 0 | 0 | 1 | 0 | 1 | 100% |
| AJCC Tumor Stage | T1 | 4 | 0 | 0 | 1 | 2 | 1 | 4 | 100% |
| | T2 | 20 | 2 | 4 | 3 | 7 | 4 | 18 | 90% |
| | T3 | 18 | 1 | 0 | 3 | 4 | 10 | 17 | 94% |
| | T4 | 5 | 0 | 0 | 1 | 2 | 2 | 5 | 100% |

The 7BD-33-11A staining was specific for cancerous cells in comparison to normal cells where stromal cells were clearly negative and sheets of malignant cells were positive. The cellular localization pattern seen with the 7BD-33-11A antigen was confined to the cell membrane and cytoplasm. Similar membranous and cytoplasmic staining results were obtained with the anti-CD63 antibodies, RFAC4 and H5C6 on the breast tumor tissue samples. Additionally, both of these antibodies showed this staining localization pattern on normal breast tissue samples whereas 7BD-33-11A was negative.

Figure 20:
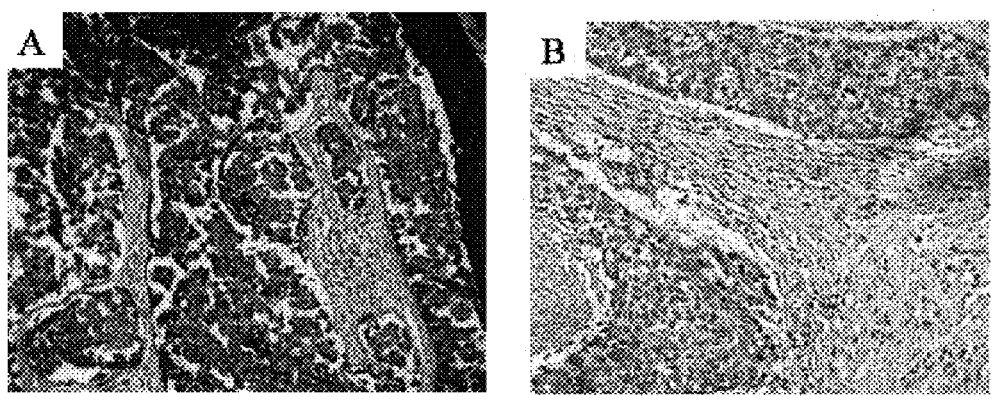
FIG. 20. Representative micrographs showing the binding pattern obtained with 7BD-33-11A (A) or the anti-Her2 (c-erbB-2) antibody (B) on tissues sections of infiltrative ductal carcinoma from a human breast cancer tissue array. 7BD-33-11A displayed strong positive staining for the tumor cells in comparison to the anti-Her2 antibody, which displayed negative staining. Magnification is 200×.

In comparison to c-erbB-2 anti-Her2, 7BD-33-11A showed a completely different staining profile where 9 out of the 18 breast tumor tissue samples that were positive for the 7BD-33-11A antigen were negative for Her2 expression indicating a yet unmet targeted therapeutic need for breast cancer patients (Table 15, FIG. 20). There were also differences in the intensity of staining between the breast tumor tissue sections that were positive for both 7BD-33-11A and Her2; some breast tumor tissue sections that were highly positive for the 7BD-33-11A antigen were only mildly positive for Her2 and vice versa again illustrating that 7BD-33-11A would therapeutically target a different cohort of breast cancer patients. The c-erbB-2 antibody also positively stained one of the normal breast tissue sections.

These results suggested the antigen for 7BD-33-11A may be expressed by approximately two thirds of breast cancer patients and half of those were completely negative for the Her2 antigen. The staining pattern showed that in patient samples, the antibody is highly specific for malignant cells and the 7BD-33-11A antigen was present on the cell membrane thereby making it an attractive drugable target. The similar albeit much more limited staining of 7BD-33-11A versus either the RFAC4 or H5C6 anti-CD63 antibody again demonstrates the likelihood of the 7BD-33-11A epitope being a more restrictive epitope on CD63.

TABLE 14

Comparison of RFAC4 and H5C6 anti-CD63 and 7BD-33-11A IHC on Human Tumor and Normal Breast Tissue

| | | | Data sheet | RFAC4 | H5C6 | 7BD-33-11A |
|---|---|---|---|---|---|---|
| Sec. No. | Sex | Age | Diagnosis | Section Score | Section Score | Section Score |
| 1 | F | 28 | Infiltrating duct carcinoma | +++ | +++ | ++ |
| 2 | F | 71 | Solid papillary carcinoma | +++ | +++ | +/− |
| 3 | F | 26 | Infiltrating duct carcinoma | ++ | + | − |
| 4 | F | 43 | Infiltrating duct carcinoma | ++ | ++ | +/− |
| 5 | F | 39 | Infiltrating duct carcinoma | NR | NR | +/− |
| 6 | F | 46 | Ductal carcinoma in situ | + | + | +/− |
| 7 | F | 47 | Infiltrating duct carcinoma | +++ | +++ | + |
| 8 | M | 67 | Infiltrating duct carcinoma | +++ | +++ | + |
| 9 | F | 33 | Infiltrating duct carcinoma | +++ | +++ | − |
| 10 | F | 47 | Infiltrating duct carcinoma | ++ | ++ | − |
| 11 | F | 49 | Invasive lobular carcinoma | − | − | − |
| 12 | F | 46 | Infiltrating duct carcinoma | ++ | ++ | − |
| 13 | F | 39 | Infiltrating duct carcinoma | ++ | ++ | − |
| 14 | F | 43 | Infiltrating lobular carcinoma | +++ | +++ | +/− |
| 15 | F | 54 | Infiltrating lobular carcinoma | ++ | ++ | +/− |
| 16 | F | 58 | Infiltrating duct carcinoma | + | ++ | +/− |
| 17 | F | 37 | Infiltrating duct carcinoma | +++ | ++ | − |
| 18 | F | 43 | Infiltrating duct carcinoma | +++ | +++ | +++ |
| 19 | F | 51 | Infiltrating duct carcinoma | +++ | +++ | + |
| 20 | F | 80 | Medullary carcinoma | ++ | ++ | − |
| 21 | F | 36 | Infiltrating duct carcinoma | NR | NR | − |
| 22 | F | 59 | Infiltrating duct carcinoma | + | + | − |
| 23 | F | 34 | Ductal carcinoma in situ | +++ | +++ | + |
| 24 | F | 54 | Infiltrating duct carcinoma | ++ | +++ | +/− |
| 25 | F | 47 | Infiltrating duct carcinoma | +++ | +++ | ++ |
| 26 | F | 53 | Infiltrating duct carcinoma | ++ | ++ | − |
| 27 | F | 59 | Infiltrating duct carcinoma | + | + | − |
| 28 | F | 60 | Signet ring cell carcinoma | F | F | − |
| 29 | F | 37 | Infiltrating duct carcinoma | +++ | +++ | ++ |
| 30 | F | 46 | Infiltrating duct carcinoma | ++ | ++ | +/− |
| 31 | F | 35 | Infiltrating duct carcinoma | − | − | − |
| 32 | F | 47 | Infiltrating duct carcinoma | ++ | ++ | − |
| 33 | F | 54 | Infiltrating duct carcinoma | + | + | − |
| 34 | F | 47 | Infiltrating duct carcinoma | − | +/− | − |
| 35 | F | 41 | Infiltrating duct carcinoma | +++ | +++ | − |
| 36 | F | 38 | Infiltrating duct carcinoma | +++ | +++ | − |
| 37 | F | 55 | Infiltrating duct carcinoma | − | +/− | − |
| 38 | F | 65 | Infiltrating duct carcinoma | +/− | +/− | − |
| 39 | M | 66 | Infiltrating duct carcinoma | − | + | − |
| 40 | F | 44 | Infiltrating duct carcinoma | ++ | +++ | − |
| 41 | F | 52 | Metastatic carcinoma in lymph node | ++ | ++ | − |
| 42 | F | 32 | Metastatic carcinoma in lymph node | +/− | + | − |
| 43 | F | 58 | Metastatic carcinoma in lymph node | ++ | +++ | +/− |
| 44 | F | 52 | Metastatic carcinoma in lymph node | + | + | − |
| 45 | F | 58 | Metastatic carcinoma in lymph node | − | − | − |
| 46 | F | 38 | Metastatic carcinoma in lymph node | ++ | +++ | − |
| 47 | F | 45 | Metastatic carcinoma in lymph node | − | ++ | − |
| 48 | F | 45 | Metastatic carcinoma in lymph node | ++ | ++ | − |

TABLE 14-continued

Comparison of RFAC4 and H5C6 anti-CD63 and 7BD-33-11A IHC on Human Tumor and Normal Breast Tissue

| Data sheet | | | | RFAC4 | H5C6 | 7BD-33-11A |
|---|---|---|---|---|---|---|
| Sec. No. | Sex | Age | Diagnosis | Section Score | Section Score | Section Score |
| 49 | F | 29 | Metastatic carcinoma in lymph node | +/− | +/− | − |
| 50 | F | 61 | Metastatic carcinoma in lymph node | + | ++ | − |
| 51 | F | 46 | Nipple | ++ | ++ | − |
| 52 | F | 47 | Nipple | NR | NR | − |
| 53 | F | 40 | Normal breast | +/− | +/− | − |
| 54 | F | 43 | Normal breast | +++ | +++ | − |
| 55 | F | 40 | Normal breast | ++ | +++ | − |
| 56 | F | 40 | Normal breast | +++ | ++ | − |
| 57 | F | 45 | Normal breast | NR | NR | − |
| 58 | F | 44 | Normal breast | − | − | − |
| 59 | F | 37 | Normal breast | +++ | +++ | − |
| 60 | F | 51 | Normal breast | +++ | +++ | − |

Abbreviations:
NR: the sample is not representative and
F: the section is folded.

TABLE 15

Comparison of c-erbB-2 anti-Her2 and 7BD-33-11A IHC on Human Tumor and Normal Breast Tissue

| Data sheet | | | | c-erbB-2 | 7BD-33-11A |
|---|---|---|---|---|---|
| Sec. No. | Sex | Age | Diagnosis | Section Score | Section Score |
| 1 | F | 28 | Infiltrating duct carcinoma | + | ++ |
| 2 | F | 71 | Solid papillary carcinoma | − | +/− |
| 3 | F | 26 | Infiltrating duct carcinoma | +/− | − |
| 4 | F | 43 | Infiltrating duct carcinoma | +/− | +/− |
| 5 | F | 39 | Infiltrating duct carcinoma | NR | +/− |
| 6 | F | 46 | Ductal carcinoma in situ | − | +/− |
| 7 | F | 47 | Infiltrating duct carcinoma | +++ | + |
| 8 | M | 67 | Infiltrating duct carcinoma | − | + |
| 9 | F | 33 | Infiltrating duct carcinoma | +++ | − |
| 10 | F | 47 | Infiltrating duct carcinoma | ++ | − |
| 11 | F | 49 | Invasive Lobular carcinoma | PD | − |
| 12 | F | 46 | Infiltrating duct carcinoma | − | − |
| 13 | F | 39 | Infiltrating duct carcinoma | +++ | − |
| 14 | F | 43 | Infiltrating lobular carcinoma | − | +/− |
| 15 | F | 54 | Infiltrating lobular carcinoma | − | +/− |
| 16 | F | 58 | Infiltrating duct carcinoma | − | +/− |
| 17 | F | 37 | Infiltrating duct carcinoma | +++ | − |
| 18 | F | 43 | Infiltrating duct carcinoma | −− | +++ |
| 19 | F | 51 | Infiltrating duct carcinoma | + | + |
| 20 | F | 80 | Medullary carcinoma | − | − |
| 21 | F | 36 | Infiltrating duct carcinoma | NR | − |
| 22 | F | 59 | Infiltrating duct carcinoma | − | − |
| 23 | F | 34 | Ductal carcinoma in situ | +++ | + |
| 24 | F | 54 | Infiltrating duct carcinoma | + | +/− |
| 25 | F | 47 | Infiltrating duct carcinoma | − | ++ |
| 26 | F | 53 | Infiltrating duct carcinoma | +++ | − |
| 27 | F | 59 | Infiltrating duct carcinoma | + | − |
| 28 | F | 60 | Signet ring cell carcinoma | − | − |
| 29 | F | 37 | Infiltrating duct carcinoma | +++ | ++ |
| 30 | F | 46 | Infiltrating duct carcinoma | − | +/− |
| 31 | F | 35 | Infiltrating duct carcinoma | − | − |
| 32 | F | 47 | Infiltrating duct carcinoma | +++ | − |
| 33 | F | 54 | Infiltrating duct carcinoma | − | − |
| 34 | F | 47 | Infiltrating duct carcinoma | +++ | − |
| 35 | F | 41 | Infiltrating duct carcinoma | − | − |
| 36 | F | 38 | Infiltrating duct carcinoma | ++ | − |
| 37 | F | 55 | Infiltrating duct carcinoma | +/− | − |
| 38 | F | 65 | Infiltrating duct carcinoma | − | − |
| 39 | M | 66 | Infiltrating duct carcinoma | − | − |
| 40 | F | 44 | Infiltrating duct carcinoma | − | − |
| 41 | F | 52 | Metastatic carcinoma in Lymph node | − | − |
| 42 | F | 32 | Metastatic carcinoma in Lymph node | − | − |
| 43 | F | 58 | Metastatic carcinoma in Lymph node | ++ | +/− |
| 44 | F | 52 | Metastatic carcinoma in Lymph node | +++ | − |

TABLE 15-continued

Comparison of c-erbB-2 anti-Her2 and 7BD-33-11A IHC on Human Tumor and Normal Breast Tissue

| | | | Data sheet | c-erbB-2 | 7BD-33-11A |
|---|---|---|---|---|---|
| Sec. No. | Sex | Age | Diagnosis | Section Score | Section Score |
| 45 | F | 58 | Metastatic carcinoma in Lymph node | − | − |
| 46 | F | 38 | Metastatic carcinoma in Lymph node | ++ | − |
| 47 | F | 45 | Metastatic carcinoma in Lymph node | − | − |
| 48 | F | 45 | Metastatic carcinoma in Lymph node | − | − |
| 49 | F | 29 | Metastatic carcinoma in Lymph node | − | − |
| 50 | F | 61 | Metastatic carcinoma in Lymph node | − | − |
| 51 | F | 46 | Nipple | − | − |
| 52 | F | 47 | Nipple | +++ | − |
| 53 | F | 40 | Normal Breast | − | − |
| 54 | F | 43 | Normal Breast | − | − |
| 55 | F | 40 | Normal Breast | +/− | − |
| 56 | F | 40 | Normal Breast | − | − |
| 57 | F | 45 | Normal Breast | − | − |
| 58 | F | 44 | Normal Breast | − | − |
| 59 | F | 37 | Normal Breast | − | − |
| 60 | F | 51 | Normal Breast | − | − |

EXAMPLE 7

Human Prostate Tissue Staining

To determine whether the 7BD-33-11A antigen was expressed on other human cancer tissues in addition to breast cancer, a human prostate tumor tissue array was probed with 7BD-33-11A (Ser. No. 10/810,751, the contents of which are herein incorporated by reference; Imgenex Corporation, San Diego, Calif.). The staining procedure used was the same as the one outlined in Example 5. Vimentin was used as a positive control antibody and the same negative control antibody was used as described for the human breast tumor tissue array. All antibodies were used at a working concentration of 5 μg/mL.

Figure 21:
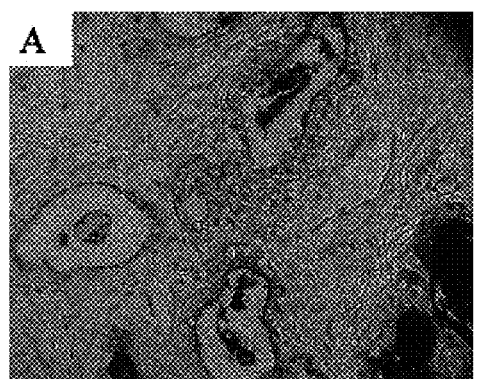
FIG. 21. Representative micrographs showing the binding pattern obtained with 7BD-33-11A on tissue sections of prostate adenocarinoma (A) or normal prostate (B) from a human prostate cancer tissue array. 7BD-33-11A displayed strong positive membranous staining for the tumor cells in the adenocarcinoma tissue section. 7BD-33-11A showed both membranous and cytoplasmic staining of the glandular epithelium in the normal prostate tissue section. Magnification is 200×.
Figure 21:
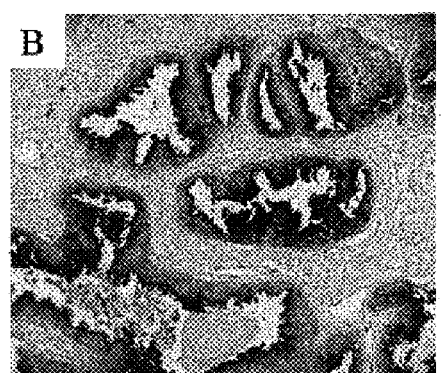

As outlined in Table 16, 7BD-33-11A stained 88 percent of human prostate cancers. Although 7BD-33-11A stained the normal tissue sections with high intensity as well, there was a higher degree of membranous staining in the tumor tissue samples in comparison to the normal samples. There was one embryonal rhabdomyosarcroma tissue sample that did not stain for the 7BD-33-11A antigen. There also appeared to be no direct correlation between tumor stage and presence of the 7BD-33-11A antigen. However, the results were limited by the small sample size. Again with 7BD-33-11A there was both membranous and cytoplasmic staining observed on the prostate tumor tissue samples. However, there was an increase in the degree of membranous staining relative to that seen with the breast tumor tissue samples (FIG. 21). For the normal prostate tissue samples, this increase in the degree of membranous staining was not observed.

TABLE 16

Human Prostate Tumor IHC Summary for 7BD-33-11A

| | | | Binding Score | | | | | | |
|---|---|---|---|---|---|---|---|---|---|
| | | Total # | − | +/− | + | ++ | +++ | Total positive | % positive of total |
| Patients' Sample | Tumor | 51 | 6 | 6 | 6 | 7 | 26 | 45 | 88% |
| | Normal | 3 | 0 | 0 | 0 | 1 | 2 | 3 | 100% |
| Tumor Subtype | Adenocarcinoma | 50 | 5 | 6 | 6 | 7 | 26 | 44 | 88% |
| | embryonal Rhabdomyosarcoma | 1 | 1 | 0 | 0 | 0 | 0 | 0 | 0% |
| Tumor Stage | I | 1 | 0 | 0 | 0 | 0 | 1 | 1 | 100% |
| | II | 11 | 0 | 0 | 1 | 3 | 7 | 11 | 100% |
| | III | 2 | 1 | 0 | 0 | 0 | 1 | 1 | 50% |
| | IV | 32 | 6 | 5 | 5 | 3 | 13 | 26 | 81% |

Therefore, it appeared that the 7BD-33-11A antigen was not solely found on the membranes of breast cancers but also on the membrane of prostate cancers. These results indicated that 7BD-33-11A has potential as a therapeutic drug in tumor types besides breast.

EXAMPLE 8

Human Melanoma Tissue Staining

To determine whether the 7BD-33-11A antigen was expressed on other human cancer tissues in addition to breast and prostate cancer, a human melanoma tumor tissue array was probed with 7BD-33-11A (Tristar Technology Group, LLC, Bethesda, Md.). The staining procedure used was the same as the one outlined in Example 5 with the exception of AEC being used as the chromogen instead of DAB. RFAC4 and NKI/C3 were used as positive control antibodies and the same negative control antibody was used as described for the human breast tumor tissue array. All antibodies were used at a working concentration of 5 μg/mL except for NKI/C3 which was used at 0.4 ug/mL.

Figure 22:
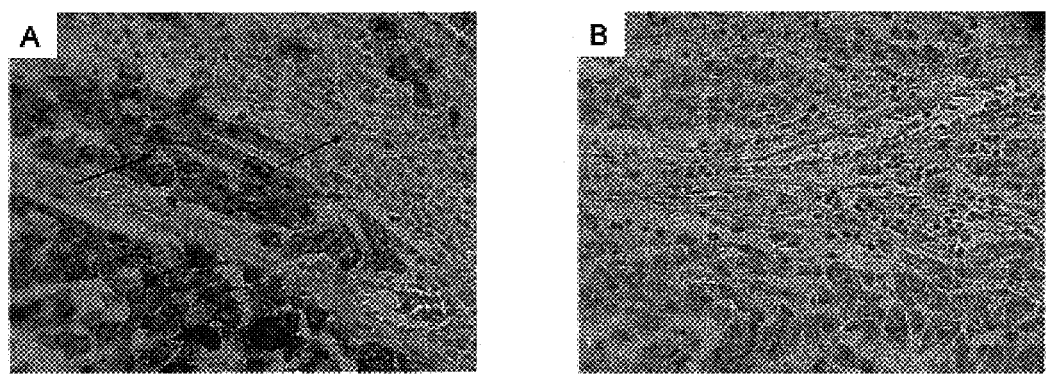
FIG. 22. Primary Malignant Melanoma. A. 7BD-33-11A (the black arrow indicates positive staining of tumor cells and the green arrow indicates an absence of staining of stroma). B. Negative isotype control. Magnification is 400×.

As outlined in Table 17, 7BD-33-11A stained 90 percent of human melanoma cancers (FIG. 22). In the limited number of samples tested, there also appeared to be no direct correlation between tumor stage and presence of the 7BD-33-11A antigen. Again with 7BD-33-11A there was both membranous and cytoplasmic staining observed on the melanoma tumor tissue samples.

TABLE 17

Human Melanoma Tumor IHC Summary for 7BD-33-11A
7BD-33-11A

|  | Total | Scoring | | | | | Total positive | % of positive tumors |
|---|---|---|---|---|---|---|---|---|
|  |  | − | +/− | + | ++ | +++ |  |  |
| Tumors AJCC staging | 39 | 4 | 2 | 6 | 10 | 17 | 35 | 89.7% |
| Stage I | 0 | 0 | 0 | 0 | 0 | 0 | 0 | 0 |
| Stage II | 5 | 0 | 0 | 1 | 1 | 3 | 5 | 100% |
| Stage III | 4 | 0 | 0 | 0 | 1 | 3 | 4 | 100% |
| Stage IV | 13 | 1 | 2 | 1 | 3 | 6 | 12 | 92% |

EXAMPLE 9

Human Tumor Tissue Staining

As partially outlined and discussed in Ser. No. 10/603,006, the contents of which are herein incorporated by reference, to determine whether either the 7BD-33-11A, H460-22-1 or 1A245.6 antigen is expressed on other human cancer tissues in addition to breast cancer, the antibodies were individually tested on a multiple human tumor tissue array (Imgenex, San Diego, Calif.). The following information was provided for each patient: age, sex, organ and diagnosis. The staining procedure used was the same as the one outlined in Example 5. Vimentin was used as a positive control antibody and the same negative control antibody was used as described for the human breast tumor tissue array. All antibodies were used at a working concentration of 5 μg/mL.

Figure 23:
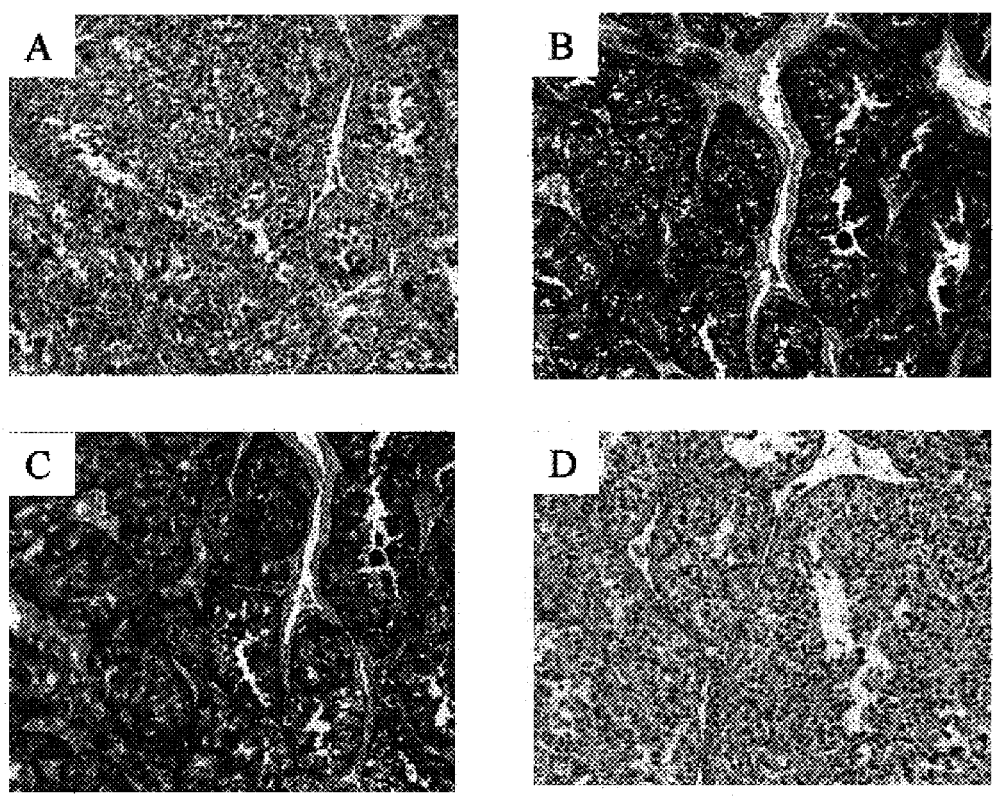
FIG. 23. Renal Cell Carcinoma. A. 7BD-33-11A. B. 1A245.6. C. H460-22-1. D. Negative isotype control. Magnification is 200×.

As outlined in Table 18, 7BD-33-11A stained a number of various human cancers besides breast. The following tumor types were positive for 7BD-33-11A: skin (1/2), lung (3/4), liver (2/3), stomach (4/5), thyroid (2/2), prostate (1/1), uterus (4/4) and kidney (3/3) (FIG. 23A). Several other tumor types also occasionally stained positive. Other tumor tissues were negative for 7BD-33-11A expression; ovary (0/3), testis (0/1), brain (0/2) and lymph node (0/2). Conversely, H460-22-1 and 1A245.6 stained every tumor tissue type tested. However, the staining varied in intensity, with some of the strongest staining seen on malignant cells of the skin, lung, liver, uterus, kidney (FIGS. 23B and C respectively), stomach and bladder. As seen with the breast and prostate (7BD-33-11A only) cancers, 7BD-33-11A, H460-22-1 and 1A245.6 staining was localized on the membrane and within the cytoplasm of cancerous cells.

Therefore, it appears that the 7BD-33-11A, H460-22-1 and 1A245.6 antigen is not solely found on the membranes of breast, prostate and melanoma cancers but also on the membrane of a large variety of tumor types. These results indicate that 7BD-33-11A, H460-22-1 and 1A245.6 have potential as therapeutic drugs in a wide variety of tumor types in addition to breast and prostate cancer.

TABLE 18

IHC Summary for H460-22-1, 1A245.6 and 7BD-33-11A on a Human Multi-Tumor Tissue Array

| Sec. No. | Age | Sex | Organ | Diagnosis | H460-22-1 |
|---|---|---|---|---|---|
| 1 | 59 | M | Skin | Malignant Melanoma | +++ M/C |
| 2 | 25 | F | Skin | SSC | ++ M/C |
| 3 | 50 | F | Breast | Inf. Ductal carcinoma | ++ M/C tumor & stroma |
| 4 | 57 | F | Breast | Inv. Papillary carcinoma | +/− PS |
| 5 | 35 | F | Breast | Inf. Lobular carcinoma | CS |
| 6 | 40 | M | Lymph node | Malignant lymphoma, immunoplastic | + M/C |
| 7 | 58 | M | Lymph node | Metastatic adenocarcinoma from stomach | ++ M/C |
| 8 | 53 | F | Bone | Osteosarcoma | ++ C |
| 9 | 26 | M | Bone | Giant cell tumor | ++ M/C |
| 10 | 40 | M | bone | Chondrosarcoma | CS |
| 11 | 51 | F | Soft tissue | liposarcoma | +/− |
| 12 | 47 | F | Soft tissue | Neurofibromatosis | +/− PS |
| 13 | 74 | M | Nasal cavity | Inverted papilloma | + M/C |
| 14 | 57 | M | Larynx | SCC | ++ tumor, +++ lymphocytes & stroma |
| 15 | 60 | M | Lung | Adenocarcinoma | +++ M/C |
| 16 | 51 | F | Lung | SCC | ++ M/C tumor & stroma |
| 17 | 68 | F | Lung | Adenocarcinoma | ++ M/C |
| 18 | 60 | M | Lung | Small cell carcinoma | +++ M/C |
| 19 | 88 | F | Tongue | SCC | ++ M/C tumor & stroma |
| 20 | 34 | F | Parotid gland | Pleomorphic adenoma | +/− mucin |
| 21 | 50 | F | Parotid gland | Warthin tumor | +++ M/C |
| 22 | 40 | F | Parotid gland | Pleomorphic adenoma | +/− |
| 23 | 56 | M | Submandibular gland | Salivary duct carcinoma | + M/C tumor & stroma |
| 24 | 69 | F | Liver | Cholangiocarcinoma | +++ M/C |
| 25 | 51 | M | Liver | Metastatic gastric Ca. | ++ M/C |
| 26 | 64 | M | Liver | HCC | +++ M/C |
| 27 | 62 | F | Gall bladder | Adenocarcinoma | ++ M/C |
| 28 | 64 | F | Pancreas | adenocarcinoma | F |

TABLE 18-continued

IHC Summary for H460-22-1, 1A245.6 and 7BD-33-11A on a Human Multi-Tumor Tissue Array

| Sec. No. | Age | Sex | Tissue | Diagnosis | H460-22-1 |
|---|---|---|---|---|---|
| 29 | 68 | M | Esophagus | SCC | +/− |
| 30 | 73 | M | Stomach | Adenocarcinoma poorly differentiated | ++ M/C tumor & stroma |
| 31 | 63 | M | Stomach | Adenocarcinoma moderately differentiated | ++ M/C |
| 32 | 59 | F | Stomach | Signet ring cell carcinoma | ++ M/C |
| 33 | 62 | M | Stomach | Malignant lymphoma | ++ M/C |
| 34 | 51 | M | Stomach | Borderline stromal tumor | ++ M/C |
| 35 | 42 | M | Small Intestine | Malignant stromal tumor | ++ M/C |
| 36 | 52 | F | Appendix | Pseuomyxoma peritonia | − PS |
| 37 | 53 | M | Colon | Adenocarcinoma | ++ M/C |
| 38 | 67 | M | Rectum | Adenocarcinoma | F |
| 39 | 75 | F | Kidney | Transitional cell carcinoma | +++ M/C |
| 40 | 54 | F | Kidney | Renal cell carcinoma | ++ M/C |
| 41 | 75 | F | Kidney | Renal cell carcinoma | +++ M/C |
| 42 | 65 | M | Urinary bladder | Poorly diff. carcinoma | + M/C |
| 43 | 67 | M | Urinary bladder | Transitional cell carcinoma, high grade | +++ M/C |
| 44 | 62 | M | Prostate | Adenocarcinoma | ++ M/C |
| 45 | 30 | M | Testis | Seminoma | + M/C |
| 46 | 68 | F | Uterus | Endometrial adenocarcinoma | +++ M/C |
| 47 | 57 | F | Uterus | Leimyosacoma | + C |
| 48 | 45 | F | Uterus | Leiomyoma | + C |
| 49 | 63 | F | Uterine cervix | SCC | + tumor cells, ++ stroma & lymphocytes |
| 50 | 12 | F | Ovary | Endodermal sinus tumor | + M/C |
| 51 | 33 | F | Ovary | Mucinous adenocarcinoma | + M/C |
| 52 | 70 | F | Ovary | Fibrothecoma | + M/C |
| 53 | 67 | F | Adrenal gland | Cortical carcinoma | ++ M/C |
| 54 | 61 | F | Adrenal gland | Pheohromcytoma | +++ M/C |
| 55 | 54 | M | Thyroid | Papillary carcinoma | +++ M/C |
| 56 | 58 | F | Thyroid | Minimally invasive follicular carcinoma | ++ M/C |
| 57 | 74 | M | Thymus | Thymoma | + C |

| Sec. No. | 1A245.6 | 7BD-33-11A | Vimentin | Isotype Control |
|---|---|---|---|---|
| 1 | ++ M/C | ++ M/C | +++ M/C | — |
| 2 | ++ M/C | − | +++ M/C | — |
| 3 | ++ M/C tumor & stroma | ++ M/C | ++ stroma only | — |
| 4 | + M/C | − | ++ stromal fibroblast & blood vessels | — |
| 5 | + M/C | F | CS | — |
| 6 | + M/C | − | +++ M/C | — |
| 7 | + M/C | − | +++ tumor & lipocytes | — |
| 8 | ++ M/C | ++ M/C | +++ M/C | — |
| 9 | ++ M/C | − | ++ M/C | — |
| 10 | CS | CS | CS | CS |
| 11 | +/− | − | +++ M/C | — |
| 12 | +/− | − | +++ M/C | — |
| 13 | + M/C | +/− | + keratin | — |
| 14 | + tumor, ++ lymphocytes & stroma | +/− tumor & stroma | +++ mainly stroma | — |
| 15 | +++ M/C | ++ M/C | ++ M/C | — |
| 16 | ++ M/C tumor & stroma | + M/C | +++ M/C | — |
| 17 | + M/C | − | +++ M/C | — |
| 18 | ++ M/C | + M/C | +++ M/C | — |
| 19 | + M/C tumor & stroma | +/− | +++ mainly stroma | — |
| 20 | +/− mucin | − | ++ M/C | — |
| 21 | +++ M/C | +++ M/C | +++ tumor & lymphocytes | — |
| 22 | + M/C | +/− | +++ M/C | — |
| 23 | + M/C tumor & stroma | − | +++ M/C | — |
| 24 | +++ M/C | ++ M/C | +/− tumor, +++ blood vessels | — |
| 25 | ++ M/C | − | ++ stroma | — |
| 26 | +++ M/C tumor & stroma | ++ M/C | +/− | — |
| 27 | ++ M/C | + M/C | + stroma | — |
| 28 | ++ M/C | ++ M/C | ++ stroma | — |
| 29 | + M/C | +/− | ++ stroma | — |
| 30 | ++ M/C tumor & stroma | + M/C | ++ mainly stroma & blood vessels | — |
| 31 | ++ M/C | +/− | ++ M/C | — |
| 32 | ++ M/C | +/− | ++ M/C | — |
| 33 | + M/C | + blood vessels | +++ M/C | — |
| 34 | +++ M/C | + M/C | ++ M/C | — |

TABLE 18-continued

IHC Summary for H460-22-1, 1A245.6 and 7BD-33-11A on a Human Multi-Tumor Tissue Array

| | | | | |
|---|---|---|---|---|
| 35 | ++ M/C | – | +++ M/C | — |
| 36 | – PS | – | + tumor, +++ lipocytes | — |
| 37 | + M/C | +/– | ++ mainly stroma | — |
| 38 | ++ M/C | – | ++ lipocytes & blood vessels | — |
| 39 | +++ M/C | ++ M/C | ++ stroma | — |
| 40 | ++ M/C | +/– | ++ M | — |
| 41 | +++ M/C | ++ M/C | + tumor, +++ stroma | — |
| 42 | ++ M/C | – | ++ mainly stroma | — |
| 43 | +++ M/C | +++ M/C | +++ stroma & blood vessels | — |
| 44 | + M/C | +/– | +++ tumor, stroma & blood vessels | — |
| 45 | + M/C | – | +++ blood vessels | — |
| 46 | +++ M/C | ++ M/C | + tumor, +++ stroma | — |
| 47 | + C | +/– | + M/C | — |
| 48 | ++ C | +/– | +++ M/C | — |
| 49 | + tumor cells, ++ stroma & lymphocytes | +/– | +/– tumor, ++ stroma | — |
| 50 | ++ M/C | – | ++ (Tumor & stroma) | — |
| 51 | + M/C | – | ++ stroma | — |
| 52 | ++ M/C | – | +++ M/C | — |
| 53 | ++ M/C | + M/C | +++ M/C | — |
| 54 | +++ M/C | – | +++ | — |
| 55 | +++ M/C | ++ M/C | +/– tumor, ++ stroma | — |
| 56 | ++ M/C | + M/C | +++ M/C | — |
| 57 | + C | +/– | ++ M/C | — |

Abbreviations:
NR: The section was not representative,
CS: The section was completely sloughed,
M: Mitochondrial staining,
C: Cytoplasmic staining.

EXAMPLE 10

AR7BD-33-11A, ARH460-22-1 and AR1A245.6 Binding to Cynomolgus and Rhesus Monkey Normal Tissues To assess antigen expression in non-human primate species, AR7BD-33-11A, ARH460-22-1, 1A245.6 and H5C6 (a commercially available anti-CD63) antibody binding was tested by IHC on normal tissues from 2 primate species. Normal tissue arrays from Cynomolgus and Rhesus monkeys were obtained from BioChain, Hayward, Calif., and stained according to the procedure outlined in Example 5. Positive (anti-actin antibody) and negative controls were also tested. Arrays were comprised of sections from the following 9 representative organs: heart, brain, kidney, liver, lung, spleen, small intestine, skeletal muscle and pancreas.

AR7BD-33-11A antibody binding was limited and compatible with that observed with human tissues. As shown in Tables 19 and 20, the antibody did not bind to heart, brain or skeletal muscle and showed weak to moderate binding in other tissues tested except for lung macrophages and pancreatic tissue where strong binding was observed. Binding was similar between the two non-human primate species with two caveats. In the Rhesus small intestine section, there was equivocal binding of a few fibroblasts, however, the corresponding Cynomolgus section was not representative and therefore could not be assessed. AR7BD-33-11A binding to liver and kidney sections was stronger with the Rhesus sample than the Cynomolgus.

TABLE 19

Results from AR7BD-33-11A IHC Staining of Cynomolgus Monkey Tissue Sections

| Biochain Data Sheet | | | | IHC Data | | | | |
|---|---|---|---|---|---|---|---|---|
| Tissue Name | Sex | Age (years) | Pathological Diagnosis | Section Score | Tissue Specificity | Cellular Localization | % Stained Cells | Staining Intensity |
| Heart | F | 3.2 | Normal | – | — | — | — | Negative |
| Brain | F | 3.2 | Normal | – | — | — | — | Negative |
| Kidney | F | 3.2 | Normal | + | Tubular Epithelium | CMD | <50% | Weak |
| Liver | F | 3.2 | Normal | ++ | Bileduct epitelium and infiltrating neutrophils | CMD | >50% | Moderate |
| | | | | | Hepatocytes | CMG | <50% | Weak |
| Lung | F | 3.2 | Normal | +++ | Pulmonary Macrophages and Interstial cells | CMD | >50% | Moderate-Strong |

TABLE 19-continued

Results from AR7BD-33-11A IHC Staining of Cynomolgus Monkey Tissue Sections

| Tissue Name | Sex | Age (years) | Pathological Diagnosis | Section Score | Tissue Specificity | Cellular Localization | % Stained Cells | Staining Intensity |
|---|---|---|---|---|---|---|---|---|
| Spleen | F | 3.2 | Normal | ++ | Neutrophils | CMG | >50% | Moderate |
| | | | | | Lymphocytes | SF | 10% | Equivocal |
| Small intestine* | F | 3.2 | Normal | − | — | — | — | Negative |
| Skeletal muscle | F | 3.2 | Normal | − | — | — | — | Negative |
| Pancreas | F | 3.2 | Normal | +++ | Islets of Langerhans | CMD | >50% | Strong |
| | | | | | Acinar Epithelium | CMD | >50% | Weak-Moderate |

The final section score depends on the strongest staining intensity of the cells as follows: Negative staining (−), Equivocal staining (+/−), Weak staining (+), Moderate staining (++), Strong staining (+++).
Cellular Localization: Membranous (M), Cytoplasmic (C), Diffuse (D), Granular (G), Sporadic focal (SF).
Approximate % stained cells: <10% (1-9%), 10%, <50% (11-49%), 50%, >50% (51-100%).
*Adipose tissue only

TABLE 20

Results from AR7BD-33-11A IHC Staining of Rhesus Monkey Tissue Sections

| Tissue Name | Sex | Age (years) | Pathological Diagnosis | Section Score | Tissue Specificity | Cellular Localization | % Stained Cells | Staining Intensity |
|---|---|---|---|---|---|---|---|---|
| Heart | M | 2.5 | Normal | − | — | — | — | Negative |
| Brain | M | 2.5 | Normal | − | — | — | — | Negative |
| Kidney | M | 2.5 | Normal | ++ | Tubular Epithelium | CMD | <50% | Weak-Moderate |
| Liver | M | 2.5 | Normal | +++ | Bileduct epitelium and infiltrating neutrophils | CMD | >50% | Strong |
| | | | | | Hepatocytes | CMG | <50% | Weak |
| Lung | M | 2.5 | Normal | +++ | Pulmonary Macrophages and Interstial cells | CMD | >50% | Moderate-Strong |
| Spleen | M | 2.5 | Normal | ++ | Neutrophils | CMG | >50% | Moderate |
| | | | | | Lymphocytes | CMD | 10% | Equivocal |
| Small intestine | M | 2.5 | Normal | +/− | fibroblsts | SF | <10% | equivocal |
| Skeletal muscle | M | 2.5 | Normal | − | — | — | — | Negative |
| Pancreas | M | 2.5 | Normal | +++ | Islets of Langerhans & acinar epithelium | CMD | >50% | Moderate-Strong |

The final section score depends on the strongest staining intensity of the cells as follows: Negative staining (−), Equivocal staining (+/−), Weak staining (+), Moderate staining (++), Strong staining (+++).
Cellular Localization: Membranous (M), Cytoplasmic (C), Diffuse (D), Granular (G), Sporadic focal (SF).
Approximate % stained cells: <10% (1-9%), 10%, <50% (11-49%), 50%, >50% (51-100%).
* Adipose tissue only Binding of ARH460-22-1 to the primate species was also compatible with what was observed in human tissues. As seen in Tables 21 and 22, except for equivocal binding observed in the Cynomolgus brain sample which was negative in the corresponding Rhesus section, ARH460-22-1 binding was similar between the two non-human primate species.

TABLE 21

Results from ARH460-22-1 IHC Staining of Cynomolgus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Heart | F | 3.2 | Normal | + | Cardiac muscle fibers & endocardium | CMG | >50% | Weak |

TABLE 21-continued

Results from ARH460-22-1 IHC Staining of Cynomolgus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Brain | F | 3.2 | Normal | +/− | Endothelium of blood vessels | SF | <10% | equivocal |
| Kidney | F | 3.2 | Normal | +++ | Tubular epithelium | CMD | >50% | Moderate-Strong |
|  |  |  |  |  | Glomeruli | SF | <10% | equivocal |
| Liver | F | 3.2 | Normal | +++ | Sinusoidal cells, bile duct epithelium, infiltrating neutrophils and endothelium of blood vessels | CMD | >50% | Moderate-Strong |
|  |  |  |  |  | Hepatocytes | CMG | >50% | Moderate |
| Lung | F | 3.2 | Normal | +++ | Pulmonary epithelium, interstial cells and macrophages | CMG | >50% | Moderate-Strong |
| Spleen | F | 3.2 | Normal | +++ | Lymphocytes in red bulb and germinal center of white bulb, neutrophils and endothelium | CMG | >50% | Moderate-Strong |
| *Small intestine | F | 3.2 | Normal | +/− | blood vessels | SF | <50% | Weak |
| Skeletal muscle | F | 3.2 | Normal | − | — | — | — | Negative |
| Pancreas | F | 3.2 | Normal |  | islets of langerhans | CMG | >50% | Strong |

The final section score depends on the strongest staining intensity of the cells as follows: Negative staining (−), Equivocal staining (+/−), Weak staining (+), Moderate staining (++), Strong staining (+++).
Cellular Localization: Membranous (M), Cytoplasmic (C), Diffuse (D), Granular (G), Sporadic focal (SF).
Approximate % stained cells: <10% (1-9%), 10%, <50% (11-49%), 50%, >50% (51-100%).
*Adipose tissue only

TABLE 22

Results from ARH460-22-1 IHC Staining of Rhesus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Heart | M | 2.5 | Normal | + | Cardiac muscle fibers | CMG | >50% | Weak |
| Brain | M | 2.5 | Normal | − | — | — | — | Negative |
| Kidney | M | 2.5 | Normal | +++ | Tubular epithelium | CMD | >50% | Moderate-Strong |
|  |  |  |  |  | Glomeruli | SF | <10% | equivocal |
| Liver | M | 2.5 | Normal | +++ | Sinusoidal cells, bile duct epithelium, infiltrating neutrophils and endothelium of blood vessels | CMD | >50% | Moderate-Strong |
|  |  |  |  |  | Hepatocytes | CMG | >50% | Moderate |
| Lung | M | 2.5 | Normal | +++ | Pulmonary epithelium, interstial cells and macrophages | CMG | >50% | Moderate-Strong |
| Spleen | M | 2.5 | Normal | +++ | Lymphocytes in red bulb and germinal center of white bulb, neutrophils and endothelium | CMG | >50% | Moderate-Strong |
| Small intestine | M | 2.5 | Normal | ++ | Mucosal & glandular epithelium | CMG | >50% | Weak-Moderate |
| Skeletal muscle | M | 2.5 | Normal | − | — | — | — | Negative |

TABLE 22-continued

Results from ARH460-22-1 IHC Staining of Rhesus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Pancreas | M | 2.5 | Normal | +++ | islets of langerhans, acinar epithelium and endothelium of blood vessels | CMG | >50% | Strong |

The final section score depends on the strongest staining intensity of the cells as follows: Negative staining (−), Equivocal staining (+/−), Weak staining (+), Moderate staining (++), Strong staining (+++).
Cellular Localization: Membranous (M), Cytoplasmic (C), Diffuse (D), Granular (G), Sporadic focal (SF).
Approximate % stained cells: <10% (1-9%), 10%, <50% (11-49%), 50%, >50% (51-100%).
*Adipose tissue only AR1A245.6 binding to the primate species was also compatible with what was observed in human tissues. As shown in Tables 23 and 24, AR1A245.6 tissue binding was similar between the two species with the following exceptions: skeletal muscle (negative in Rhesus, equivocal in Cynomolgus), cardiac muscle (stronger in Rhesus than in Cynomolgus) and brain (stronger in Cynomolgus than in Rhesus).

TABLE 23

Results from AR1A245.6 IHC Staining of Cynomolgus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Heart | F | 3.2 | Normal | + | Cardiac muscle fibers & endocardium | CMG | >50% | Weak |
| Brain | F | 3.2 | Normal | ++ | Edothelium of blood vesseles | CMG | <50% | Moderate |
|  |  |  |  |  | Neurons and neuroglia | SF | <10% | equivocal |
| Kidney | F | 3.2 | Normal | +++ | Renal glomeruli and tubules | CMG | >50% | Strong |
| Liver | F | 3.2 | Normal | +++ | Hepatocytes, sinusoidal cells, bile duct epithelium, infiltrating neutrophils and endothelium of blood vessels | CMG | >50% | Moderate-strong |
| Lung | F | 3.2 | Normal | +++ | Pulmonary epithelium, interstial cells and macrophages | CMG | >50% | Moderate-Strong |
| Spleen | F | 3.2 | Normal | +++ | Lymphocytes in red bulb and germinal center of white bulb, neutrophils and endothelium | CMG | >50% | Moderate-Strong |
| *Small intestine | F | 3.2 | Normal | + | Adipocytes and blood vessels | CMG | 10% | Weak |
| Skeletal muscle | F | 3.2 | Normal | +/− | Endothelium of blood vessels | SF | <50% | Equivocal |
| Pancreas | F | 3.2 | Normal | +++ | Acinar epithelium and islets of langerhans | CMG | >50% | Strong |

The final section score depends on the strongest staining intensity of the cells as follows: Negative staining (−), Equivocal staining (+/−), Weak staining (+), Moderate staining (++), Strong staining (+++).
Cellular Localization: Membranous (M), Cytoplasmic (C), Diffuse (D), Granular (G), Sporadic focal (SF).
Approximate % stained cells: <10% (1-9%), 10%, <50% (11-49%), 50%, >50% (51-100%).
*Adipose tissue only

TABLE 24

Results from AR1A245.6 IHC Staining of Rhesus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Heart | M | 2.5 | Normal | ++ | Cardiac muscle fibers | CMG | >50% | Weak-Moderate |
| Brain | M | 2.5 | Normal | +/− | Neurons, neuroglia, Endothelium of blood | SF | <50% | Equivocal |

TABLE 24-continued

Results from AR1A245.6 IHC Staining of Rhesus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Kidney | M | 2.5 | Normal | +++ | Renal tubules | CMG | >50% | Moderate-strong |
| | | | | | Renal glomeruli | SF | <50% | Equivocal |
| Liver | M | 2.5 | Normal | +++ | Hepatocytes, sinusoidal cells, bile duct epithelium, infiltrating neutrophils and endothelium of blood | CMG | >50% | Moderate-strong |
| Lung | M | 2.5 | Normal | +++ | Pulmonary epithelium, interstial cells and macrophages | CMG | >50% | Moderate-Strong |
| Spleen | M | 2.5 | Normal | +++ | Lymphocytes in red bulb and germinal center of white bulb, neutrophils and | CMG | >50% | Moderate-Strong |
| Small intestine | M | 2.5 | Normal | +++ | Mucosal & glandular epithelium | CMG | >50% | Moderate Strong |
| Skeletal muscle | M | 2.5 | Normal | − | — | — | — | Negative |
| Pancreas | M | 2.5 | Normal | +++ | Acinar, ductal epithelium and islets of langerhans | CMG | >50% | Strong |

The final section score depends on the strongest staining intensity of the cells as follows: Negative staining (−), Equivocal staining (+/−), Weak staining (+), Moderate staining (++), Strong staining (+++).
Cellular Localization: Membranous (M), Cytoplasmic (C), Diffuse (D), Granular (G), Sporadic focal (SF).
Approximate % stained cells: <10% (1-9%), 10%, <50% (11-49%), 50%, >50% (51-100%).
*Adipose tissue only As was observed with human tissues, H5C6 binding (outlined in Tables 25 and 26) exhibited a similar binding pattern to that of H460-22-1 and AR1A245.6, binding a broader range of tissues than AR7BD-33-11A. For all four anti-CD63 antibodies, cellular localization was mainly cytoplasmic with granular staining pattern.

TABLE 25

Results from H5C6 IHC Staining of Cynomolgus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Heart | F | 3.2 | Normal | + | Cardiac muscle fibers & | CMG | >50% | Weak |
| Brain | F | 3.2 | Normal | +/− | endothelium of blood vessels | SF | <10% | equivocal |
| Kidney | F | 3.2 | Normal | +++ | Tubular epithelium | CMD | >50% | Strong |
| | | | | | Glomeruli | SF | <10% | equivocal |
| Liver | F | 3.2 | Normal | +++ | Sinusoidal cells, bile duct epithelium, infiltrating neutrophils and endothelium of | CMG | >50% | Strong |
| | | | | | Hepatocytes | CMG | >50% | Weak-Moderate |
| Lung | F | 3.2 | Normal | +++ | Pulmonary epithelium, interstial cells and macrophages | CMG | >50% | Moderate-Strong |
| Spleen | F | 3.2 | Normal | +++ | Lymphocytes in red bulb and germinal center of white bulb, neutrophils and endothelium | CMG | >50% | Moderate-Strong |
| *Small intestine | F | 3.2 | Normal | +/− | blood vessels | SF | <50% | Weak |
| Skeletal muscle | F | 3.2 | Normal | − | — | — | — | Negative |

TABLE 25-continued

Results from H5C6 IHC Staining of Cynomolgus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Pancreas | F | 3.2 | Normal | +++ | islets of langerhans | CMG | >50% | Strong |
|  |  |  |  |  | Acinar epithelium and endothelium of blood vessels | CMG | >50% | Weak-Moderate |

The final section score depends on the strongest staining intensity of the cells as follows: Negative staining (−), Equivocal staining (+/−), Weak staining (+), Moderate staining (++), Strong staining (+++).
Cellular Localization: Membranous (M), Cytoplasmic (C), Diffuse (D), Granular (G), Sporadic focal (SF).
Approximate % stained cells: <10% (1-9%), 10%, <50% (11-49%), 50%, >50% (51-100%).
*Adipose tissue only

TABLE 26

Results from H5C6 IHC Staining of Rhesus Monkey Tissue Sections

| Tissue | Sex | Age (years) | Pathological Diagnosis | Section Score | Tissue Specificity | Cellular Localization | % Stained Cells | Staining Intensity |
|---|---|---|---|---|---|---|---|---|
| Heart | M | 2.5 | Normal | + | Cardiac muscle fibers | CMG | >50% | Weak |
| Brain | M | 2.5 | Normal | +/− | endothelium of blood vessels | SF | <10% | equivocal |
| Kidney | M | 2.5 | Normal | +++ | Tubular epithelium | CMD | >50% | Strong |
|  |  |  |  |  | Glomeruli | SF | <10% | equivocal |
| Liver | M | 2.5 | Normal | +++ | Sinusoidal cells, bile duct epithelium, infiltrating neutrophils and endothelium of blood | CMG | >50% | Strong |
|  |  |  |  |  | Hepatocytes | CMG | >50% | Weak-Moderate |
| Lung | M | 2.5 | Normal | +++ | Pulmonary epithelium, interstial cells and macrophages | CMG | >50% | Moderate-Strong |
| Spleen | M | 2.5 | Normal | +++ | Lymphocytes in red bulb and germinal center of white bulb, neutrophils and endothelium | CMG | >50% | Moderate-Strong |
| Small intestine | M | 2.5 | Normal | ++ | Mucosal & glandular epithelium | CMG | >50% | Weak-Moderate |
| Skeletal muscle | M | 2.5 | Normal | − | — | — | — | Negative |
| Pancreas | M | 2.5 | Normal | +++ | islets of langerhans | CMG | >50% | Strong |
|  |  |  |  |  | Acinar epithelium and endothelium of blood vessels | CMG | >50% | Weak-Moderate |

The final section score depends on the strongest staining intensity of the cells as follows: Negative staining (−), Equivocal staining (+/−), Weak staining (+), Moderate staining (++), Strong staining (+++).
Cellular Localization: Membranous (M), Cytoplasmic (C), Diffuse (D), Granular (G), Sporadic focal (SF).
Approximate % stained cells: <10% (1-9%), 10%, <50% (11-49%), 50%, >50% (51-100%).

These data provide evidence that the antigen for H460-22-1, AR1A245.6, AR7BD-33-11A and H5C6 is expressed similarly in man and Cynomolgus and Rhesus monkeys, and that these non-human primate species present potential in vivo models to study the safety and pharmacokinetics of H460-22-1, 1A245.6 or AR7BD-33-11A administration.

EXAMPLE 11

In Vivo MDA-MB-231 Preventative Tumor Experiments

With reference to the data shown in FIGS. 24 and 25, 4 to 8 week old, female SCID mice were implanted with 5 million MB-231 human breast cancer cells in 100 μL saline injected subcutaneously in the scruff of the neck. The mice were randomly divided into 3 treatment groups of 10. On the day prior to implantation 20 mg/kg of H460-22-1 test antibody, antibody buffer or isotype control antibody (known not to bind MB-231 cells) was administered intrapertioneally at a volume of 300 μL after dilution from the stock concentration with a diluent that contained 2.7 mM KCl, 1 mM $KH_2PO_4$, 137 mM NaCl and 20 mM $Na_2HPO_4$. The antibodies were then administered once per week for a period of 7 weeks in the same fashion.

Tumor growth was measured roughly every 7th day with calipers for up to 10 weeks or until individual animals reached the Canadian Council for Animal Care (CCAC) end-points or day 120. Body weights of the animals were recorded for the duration of the study. At the end of the study all animals were euthanised according to CCAC guidelines.

The data presented in this study is a typical example of a longitudinal data set. Usually, in such data sets there are high correlations among time-points and higher correlations are observed between closer time-points. Because of this, repeated measures analysis of variance (Rep. ANOVA) was used to determine the differences among treatments and the method of analysis of covariance was used to determine the time-points when differences occurred. The latter is a suitable method when the differences among groups at each time-point may not be just due to groups but may be due to the previous time-points.

Figure 24:
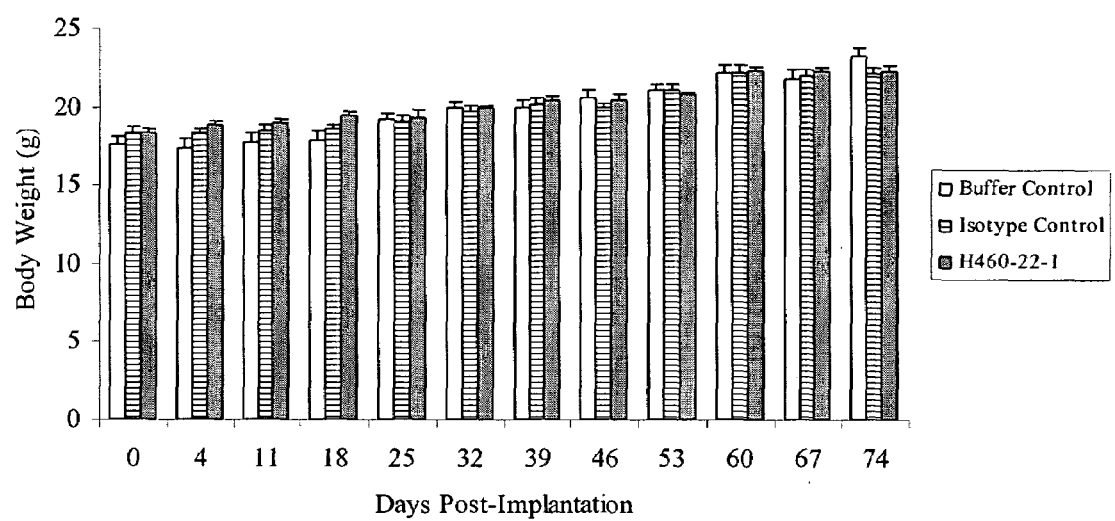
FIG. 24. Effect of H460-22-1, isotype control or buffer control on body weight in a preventative MDA-MB-231 breast cancer model.

There were no clinical signs of toxicity throughout the study. Body weight measured at weekly intervals was a surrogate for well-being and failure to thrive. FIG. 24 represents the mean body weight of mice for the 3 groups over the study period. Body weights within each group increased over time. Rep. ANOVA indicated that there was no significant difference among groups and the mean profiles do not differ over time-points for the groups treated with isotype control, antibody buffer or H460-22-1.

Figure 25:
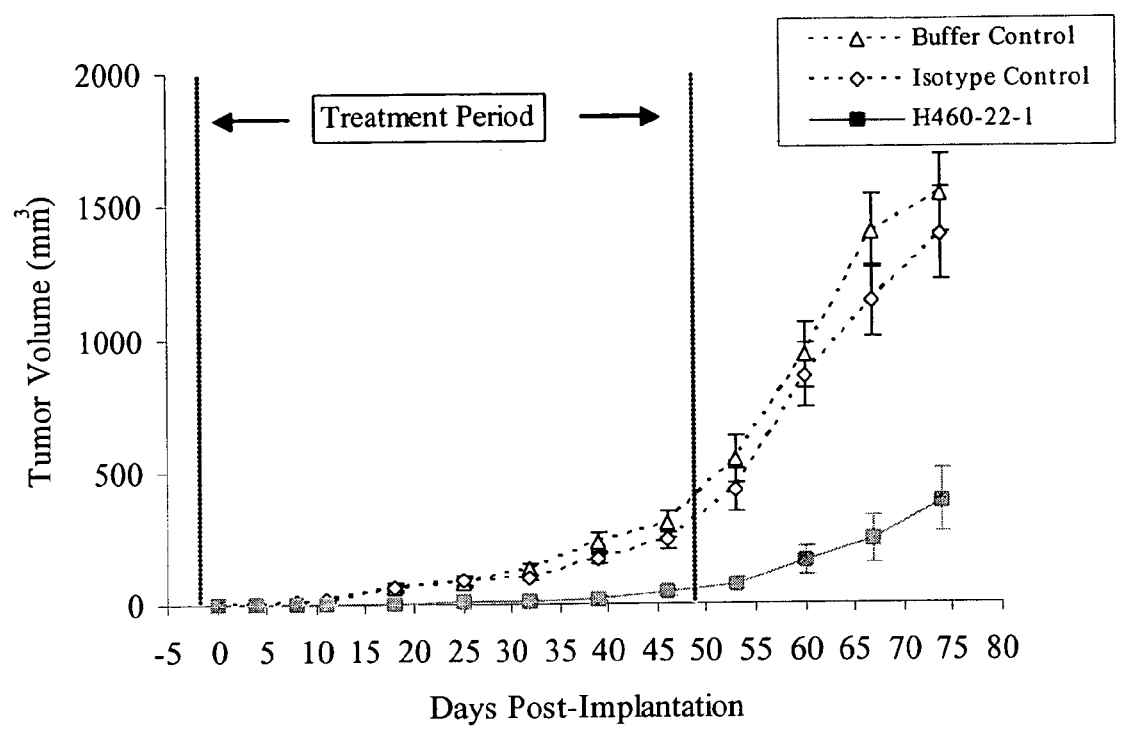
FIG. 25. Effect of H460-22-1, isotype control or buffer control on tumor growth in a preventative MDA-MB-231 breast cancer model. The dashed line indicates the period during which the antibody was administered. Data points represent the mean +/−SEM.
Figure 26:
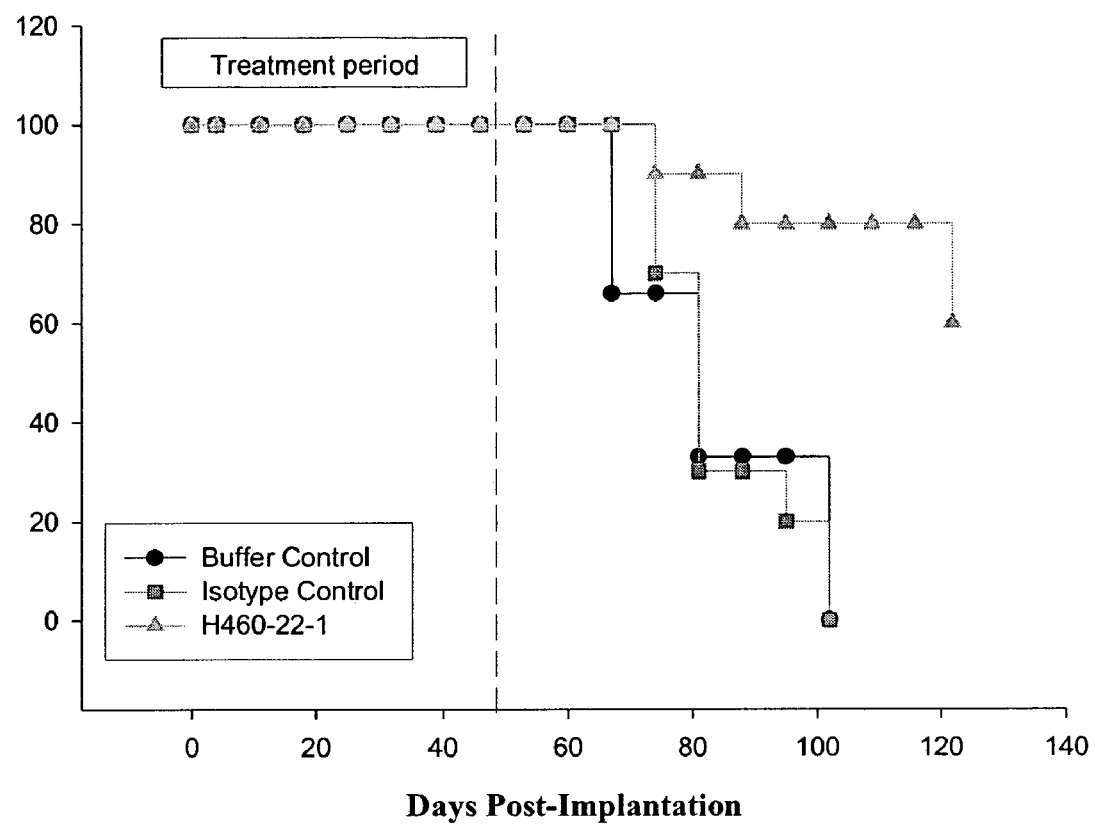
FIG. 26. Effect of H460-22-1, isotype control or buffer control on survival in a preventative MDA-MB-231 breast cancer model. The dashed line indicates the period during which the antibody was administered.

Using Rep. ANOVA for the whole experiment, the following results were noticeable. The Rep. ANOVA method indicated that not only the means of the groups were different (p<0.001) but also the shapes of the mean profiles differed from each other. As can be seen in FIG. 25, treatment group H460-22-1 seemed to have a superior effect compared to the other groups. In addition, the difference between the isotype control treated group and the antibody buffer treated group was not statistically significant. From analysis of covariance, significant differences occurred for the first time at day 18, where isotype and buffer treatment groups differed from the H460-22-1 treatment group. At day 53, (the first tumor volume measurement after the cessation of treatment) tumor volume of the group treated with H460-22-1 was 17.7% of the antibody control treated group (p<0.0001) thereby demonstrating effectiveness at preventing tumor burden. There was also a corresponding survival benefit (FIG. 26) from treatment with H460-22-1. Enhanced survival is a valuable indicator of efficacy. All 3 groups were followed for over 70 days post-treatment. These data demonstrate that treatment with the test antibody confers a survival benefit compared to control-treated groups. Control groups reached 50 percent mortality between day 74-81 post-implantation. In contrast, the H460-22-1 treated group had not reached 50 percent mortality at the time of termination of the study (day 120 post-implantation). The isotype control group treatment group reached 100 percent mortality by day 102 post-implantation. In contrast, H460-22-1 treated animals displayed 60 percent survival at the end of the study.

In summary, H460-22-1 antibody treatment prevented tumor burden and increased survival in comparison to a control antibody in a well-recognized model of human cancer disease. These results suggest a potential pharmacologic and pharmaceutical benefit of this antibody (H460-22-1) as a therapy in other mammals, including man.

EXAMPLE 12

In Vivo MDA-MB-231 Established Tumor Experiments

Female SCID mice, 5 to 6 weeks old, were implanted with 5 million MB-231 breast cancer cells in 100 µL saline injected subcutaneously in the scruff of the neck. Tumor growth was measured with calipers every week. When the majority of the cohort reached a tumor volume of 100 mm$^3$ (range 70-130 mm$^3$) at 34 days post implantation, 12 mice were randomized into each of three treatment groups. H460-22-1 or isotype control antibody (known not to bind MB-231 cells) was administered intravenously with 15 mg/kg/dose at a volume of 150 µL after dilution from the stock concentration with a diluent that contained 2.7 mM KCl, 1 mM $KH_2PO_4$, 137 mM NaCl and 20 mM $Na_2HPO_4$; cisplatin was administered at 9 mg/kg/dose (diluted in saline) intraperitoneally in 300 µL. The antibodies were then administered 3 times per week for a total of 10 doses in the same fashion until day 48 post-implantation. Cisplatin was administered every four days for 3 doses. Tumor growth was measured around every 7th day with calipers for the duration of the study or until individual animals reached CCAC end-points. Body weights of the animals were recorded for the duration of the study. At the end of the study all animals were euthanised according to CCAC guidelines.

Figure 27:
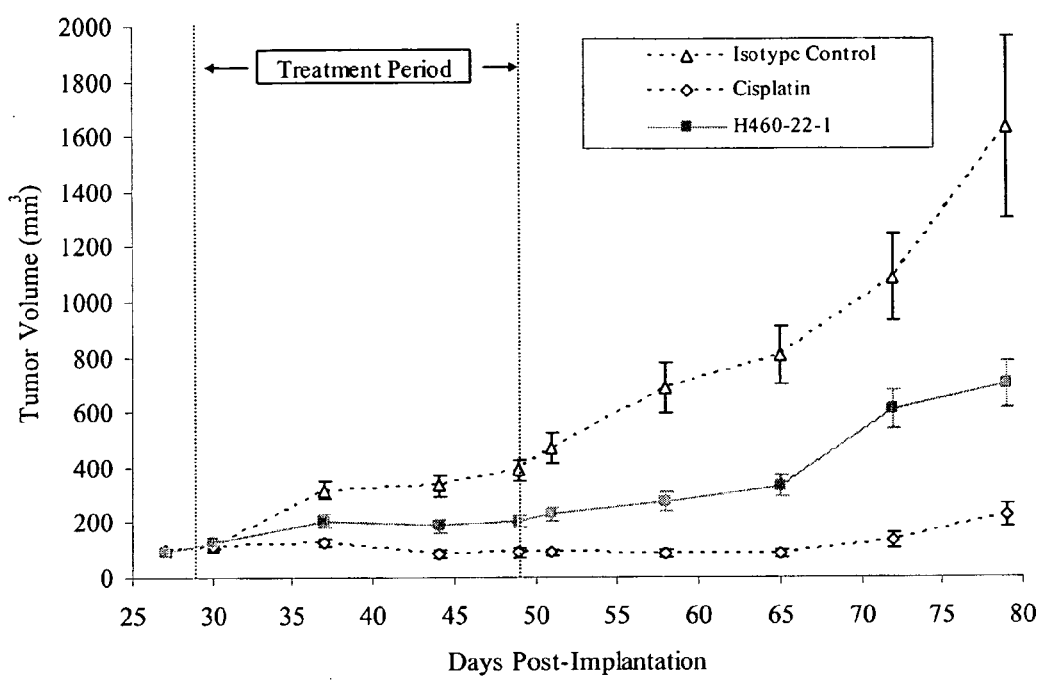
FIG. 27. Effect of H460-22-1, isotype control or cisplatin on tumor growth in an established MDA-MB-231 breast cancer model. The dashed line indicates the period during which the antibody was administered. Data points represent the mean +/−SEM.

At the time of randomization the mean tumor volumes and the standard deviations in each group were similar: isotype control, (97.60+/−18.33); H460-22-1 (94.06+/−17.77); cisplatin (98.00+/−18.93). As shown in FIG. 27 the antibody H460-22-1 was able to significantly suppress tumor growth at the end of the 3-week treatment period. Comparisons of the mean tumor volume between the 3 groups showed the differences between the groups were highly significant (Table 27).

TABLE 27

Mean Tumor Volume Comparison At End Of Treatment

| Group (1) | Group (2) | Mean Difference (1 − 2) | Std. Error | Sig. |
|---|---|---|---|---|
| Isotype | H460-22-1 | 188.81* | 41.09 | 0 |
|  | Cisplatin | 300.69* | 43.1 | 0 |
| H460-22-1 | Isotype | 188.81* | 41.09 | 0 |
|  | Cisplatin | 111.88* | 43.1 | 0.013 |
| Cisplatin | Isotype | 300.69* | 43.1 | 0 |
|  | H460-22-1 | 111.88* | 43.1 | 0.013 |

*The mean difference is significant at the 0.05 level.

Figure 28:
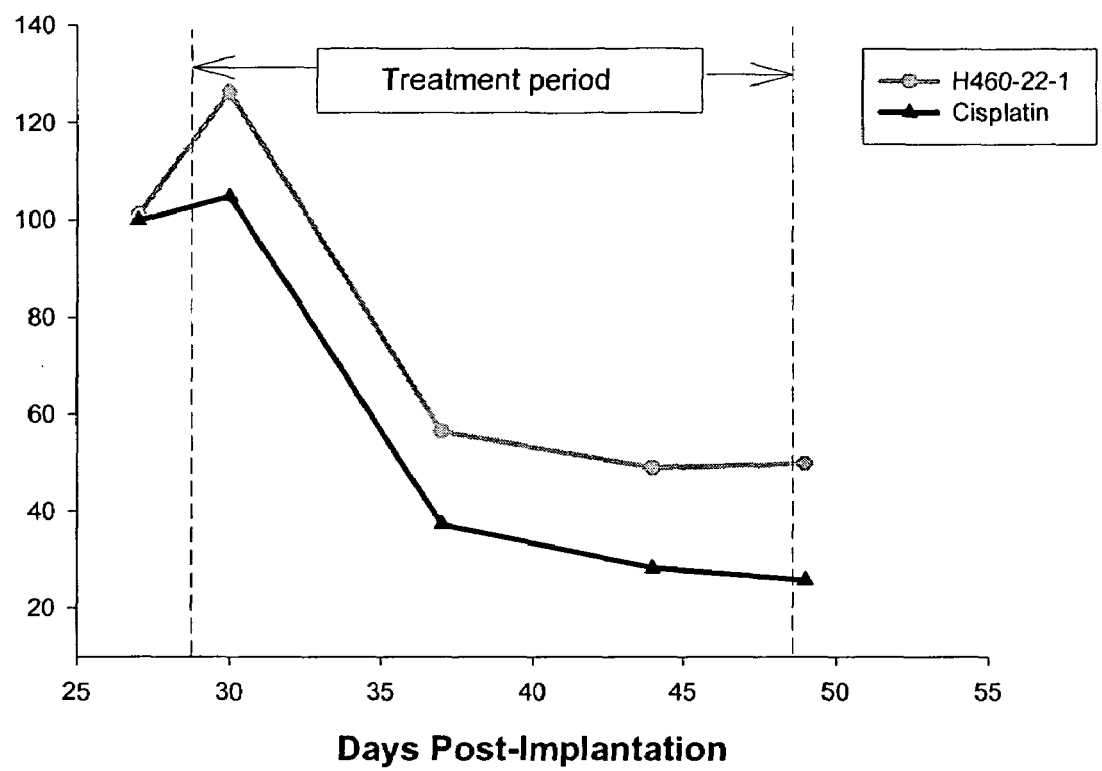
FIG. 28. Effect of H460-22-1, isotype control or cisplatin on tumor growth suppression (% T/C) in an established MDA-MB-231 breast cancer model. The dashed line indicates the period during which the antibody was administered.

Further evaluation of efficacy was assessed by calculating T/C ratios (median tumor volume of treated [T] as a percentage of the median tumor volume of isotype control [C]) which reflect growth inhibition. H460-22-1 antibody achieved a median tumor volume equal to 48 percent of control (FIG. 28). FIG. 27 further shows that H460-22-1 treatment resulted in marked suppression of tumor growth when compared to the isotype control and that the suppression was ⅔ that of cisplatin given at its maximum tolerated dose (MTD) but without cisplatin's accompanying toxicity or death.

Figure 29:
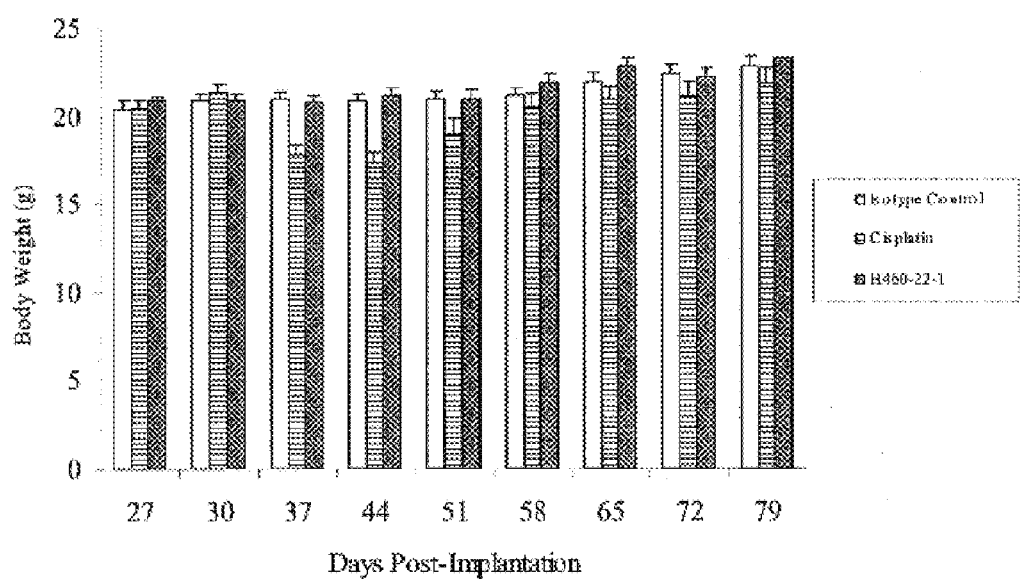
FIG. 29. Effect of H460-22-1, isotype control or cisplatin on body weight in an established MDA-MB-231 breast cancer model.

Body weights recorded weekly for the duration of the experiment were used as a surrogate for evaluation of safety and toxicity. As outlined in Table 28 and displayed in FIG. 29, there was a minimal difference in weight for the groups treated with the isotype control or H460-22-1. In contrast, during the treatment period, there was significant (p<0.003) cachexia observed in the cisplatin group. In this group, weight loss reached 19.2% of the initial body weight and additional evidence of clinical distress such as ruffled fur, skin tenting due to dehydration and lethargy occurred. There were no deaths in the H460-22-1 treated group compared to 2 deaths observed in the cisplatin treated group.

TABLE 28

Changes In Body Weight And Tumor Growth Suppression (% T/C) At End Of Treatment

| Therapeutic Agent | No./Group | Dose | % Body Weight Change | % Tumor Growth Suppression |
|---|---|---|---|---|
| Isotype control | 12 | 15 mg/kg/dose* | no mean change | |

TABLE 28-continued

Changes In Body Weight And Tumor Growth Suppression
(% T/C) At End Of Treatment

| Therapeutic Agent | No./Group | Dose | % Body Weight Change | % Tumor Growth Suppression |
|---|---|---|---|---|
| H460-22-1 | 12 | 15 mg/kg/dose* | +1.6% | 48 |
| Cisplatin | 12 (−2) | 9 mg/kg/dose** | −19.20% | 25 |

*Dose administered i.v. 3 × per week for 3 weeks.
**Dose administered i.p. 1 × every 4 days for 3 doses.

In summary, H460-22-1 is significantly more effective than the isotype control antibody in suppressing tumor growth in an established tumor xenograft model of breast cancer in SCID mice. Over the 3-week treatment period, H460-22-1 achieved a median T/C tumor less than 50 percent relative to control. In addition, H460-22-1 resulted in suppression that was two thirds that of cisplatin given at MTD but without the signs of toxicity or death observed with the chemotherapeutic drug.

Therefore treatment with H460-22-1 significantly decreased the tumor burden of established tumors in comparison to a control antibody in a well-recognized model of human disease suggesting pharmacologic and pharmaceutical benefits of this antibody for therapy in other mammals, including man.

EXAMPLE 13

In Vivo A2058 Preventative Tumor Experiments

With reference to the data shown in FIGS. 30 and 31, 4 to 8 week old, female SCID mice were implanted with 0.75 million A2058 human melanoma cancer cells in 100 μL saline injected subcutaneously in the scruff of the neck. The mice were randomly divided into 2 treatment groups of 5. On the day after implantation 20 mg/kg of 7BD-33-11A test antibody or buffer control was administered intrapertioneally at a volume of 300 μL after dilution from the stock concentration with a diluent that contained 2.7 mM KCl, 1 mM $KH_2PO_4$, 137 mM NaCl and 20 mM $Na_2HPO_4$. The antibody or buffer control was then administered once per week for a period of 7 weeks in the same fashion.

Tumor growth was measured roughly every 7th day with calipers for up to 10 weeks or until individual animals reached the Canadian Council for Animal Care (CCAC) end-points. Body weights of the animals were recorded for the duration of the study. At the end of the study all animals were euthanised according to CCAC guidelines.

Figure 30:
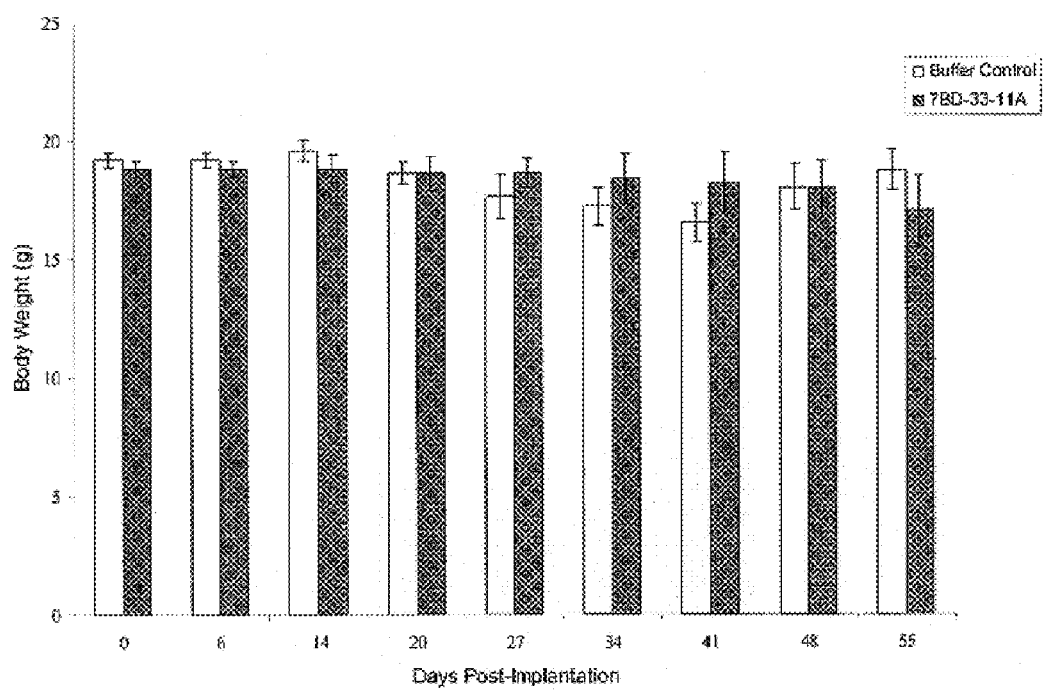
FIG. 30. Effect of 7BD-33-11A or buffer control on tumor growth in a preventative A2058 melanoma cancer model. The dashed line indicates the period during which the antibody was administered. Data points represent the mean +/−SEM.
Figure 31:
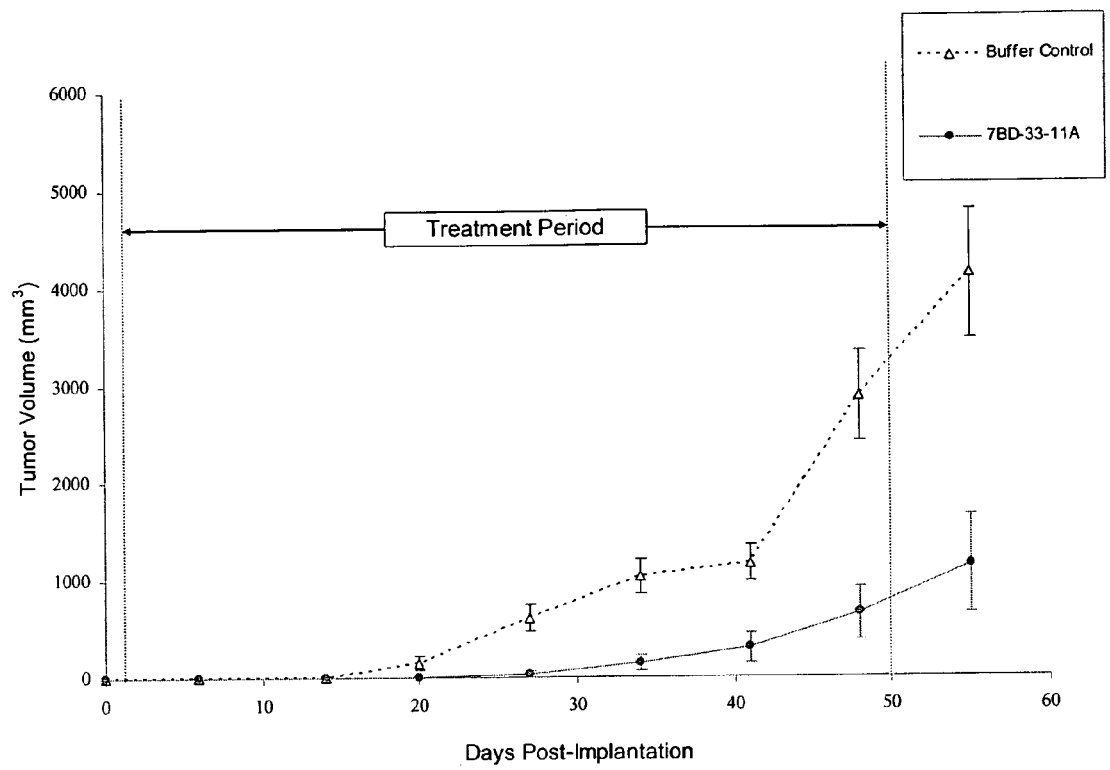
FIG. 31. Effect of 7BD-33-11A or buffer control on body weight in a preventative A2058 melanoma cancer model.

7BD-33-11A treatment resulted in decreased tumor growth compared to treatment with the buffer control (FIG. 31). On day 55 (5 days after the end of treatment), the mean tumor volume in the 7BD-33-11A treated group was 28 percent of the buffer control (p=0.0112, unpaired t-test). There were no clinical signs of toxicity as determined by body weight (FIG. 30). Also on day 55, there was no significant difference between the mean body weight of the 7BD-33-11A treatment group versus the buffer control treatment group (p=0.3351, unpaired t-test). Therefore, 7BD-33-11A treatment appeared safe and has displayed efficacy in the treatment of breast, prostate and now melanoma in vivo models of human cancer.

EXAMPLE 14

In Vivo A2058 Established Tumor Experiments

With reference to the data shown in FIGS. 32 and 33, 4 to 8 week old, female SCID mice were implanted with 5×10⁵ million A2058 human melanoma cancer cells in 100 μL saline injected subcutaneously in the scruff of the neck. Once the tumors had reached approximately 75 mm³, the mice were randomly divided into 2 groups of 7. The test group mice were treated with 15 mg/kg AR7BD-33-11A, diluted to 300 μL in vehicle control buffer (Dulbecco's Phosphate-Buffered Saline without $CaCl_2$ and $MgCl_2$), 3 times a week for a total of 10 doses. The control group mice received vehicle control buffer alone according to the same schedule.

Tumor growth was measured roughly every 7th day with calipers for the duration of the study or until individual animals reached the Canadian Council for Animal Care (CCAC) end-points. Body weights of the animals were recorded for the duration of the study. At the end of the study, all animals were euthanised according to CCAC guidelines. Survival was not a study endpoint.

Figure 32:
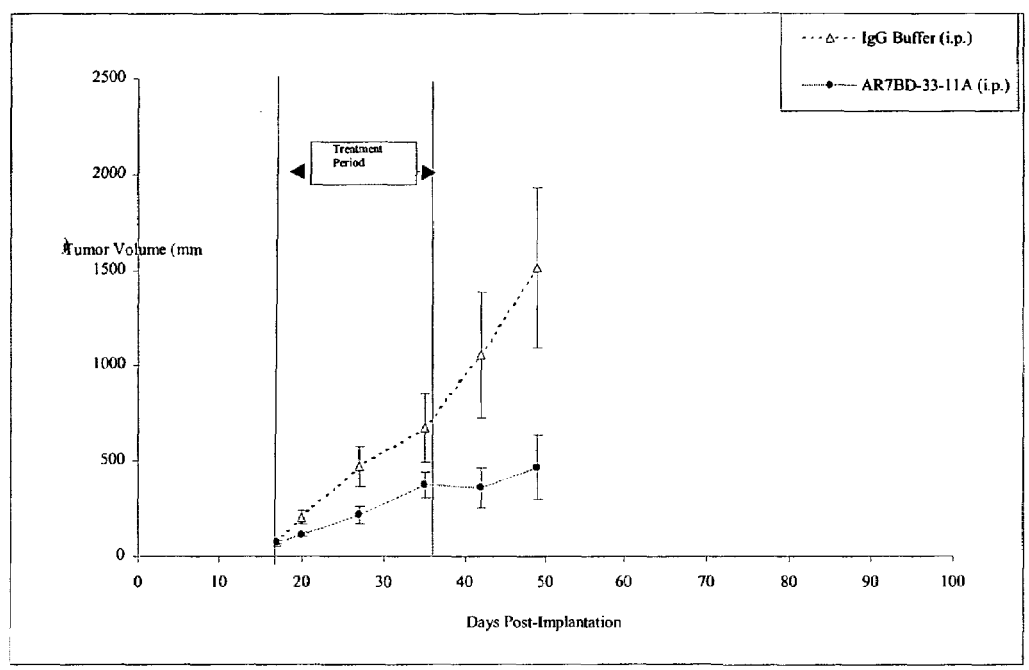
FIG. 32. Effect of 7BD-33-11A versus buffer control on tumor growth in an established A2058 melanoma cancer model. Data points represent the mean +/−SEM.
Figure 33:
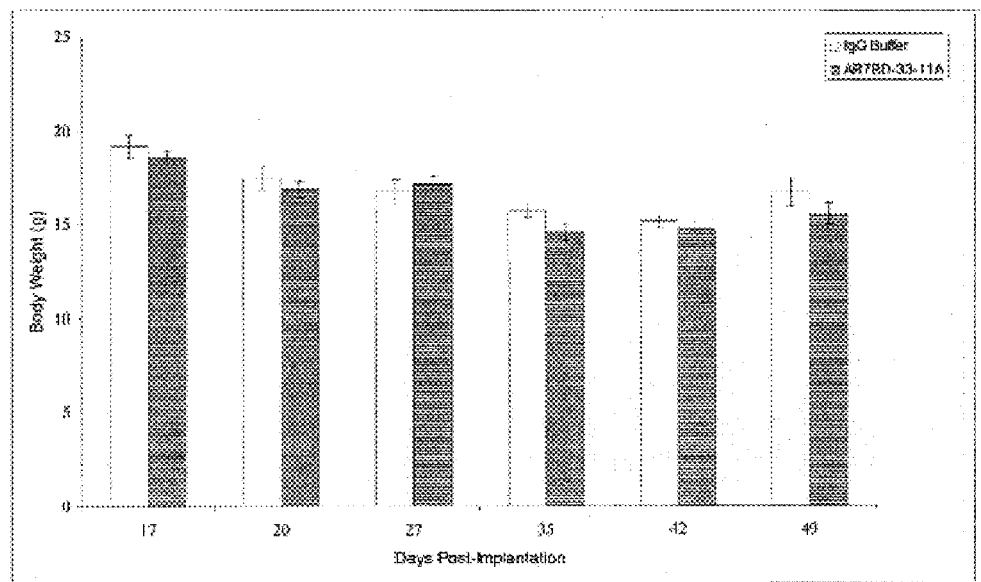
FIG. 33. Effect of 7BD-33-11A or buffer control on body weight in an established A2058 melanoma cancer model.

Tumor growth was significantly inhibited in the AR7BD-33-11A treatment group. The mean tumor volume in this group was 30.87% (p<0443) of the control group measurement (FIG. 32). No significant difference was observed in mean body weights recorded for the 2 groups (FIG. 33). Therefore, 7BD-33-11A treatment appeared safe and has displayed efficacy in the treatment of breast and now melanoma in vivo models of established human cancer.

EXAMPLE 15

In Vivo A375 Preventative Tumor Experiments

With reference to FIGS. 34 and 35, 4 to 8 week old female SCID mice were implanted with 1 million A375 human melanoma cancer cells in 100 μL saline injected subcutaneously in the scruff of the neck. The mice were randomly divided into 2 treatment groups of 5. On the day after implantation 20 mg/kg of 7BD-33-11A test antibody or buffer control was administered intrapertioneally at a volume of 300 μL after dilution from the stock concentration with a diluent that contained 2.7 mM KCl, 1 mM $KH_2PO_4$, 137 mM NaCl and 20 mM $Na_2HPO_4$. The antibody or buffer control was then administered once per week for a period of 7 weeks in the same fashion.

Tumor growth was measured roughly every 7th day with calipers for up to 10 weeks or until individual animals reached the Canadian Council for Animal Care (CCAC) end-points. Body weights of the animals were recorded for the duration of the study. At the end of the study all animals were euthanised according to CCAC guidelines.

Figure 34:
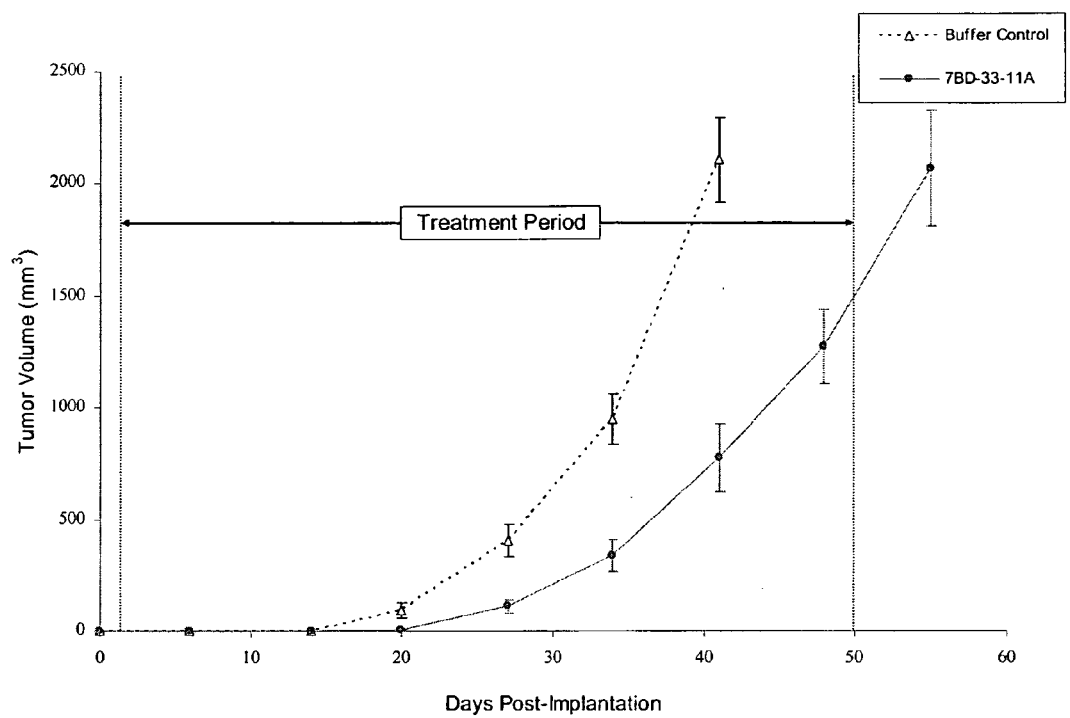
FIG. 34. Effect of 7BD-33-11A or buffer control on tumor growth in a preventative A375 melanoma cancer model. The dashed line indicates the period during which the antibody was administered. Data points represent the mean +/−SEM.
Figure 35:
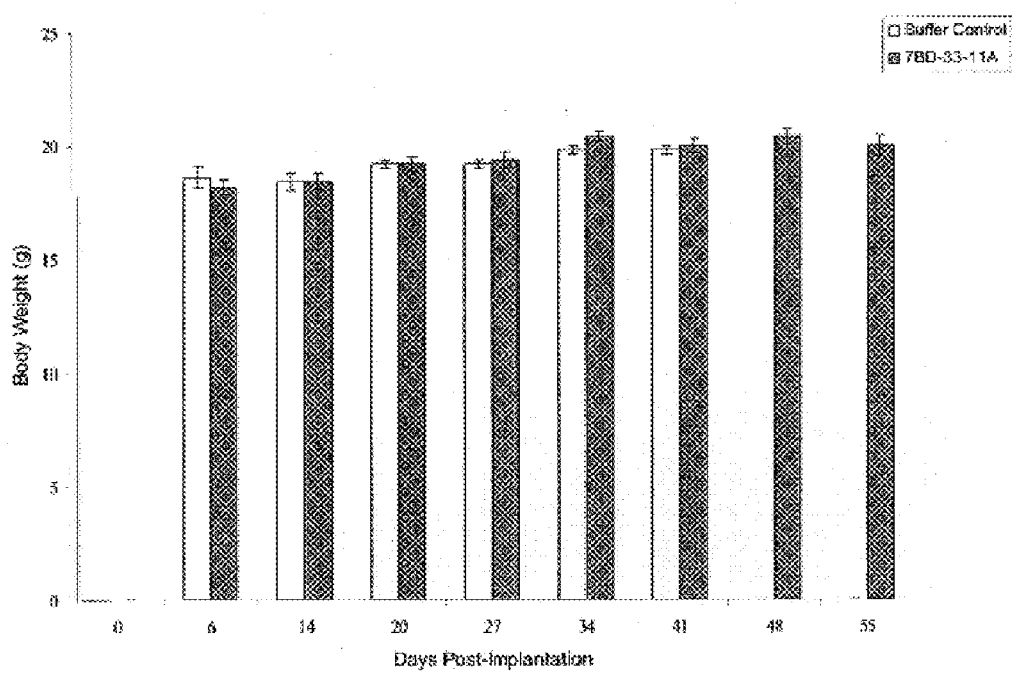
FIG. 35. Effect of 7BD-33-11A or buffer control on body weight in a preventative A375 melanoma cancer model.

7BD-33-11A treatment resulted in decreased tumor growth compared to treatment with the buffer control (FIG. 34). On day 41 (9 days before the end of treatment), the mean tumor volume in the 7BD-33-11A treated group was 37 percent of the buffer control (p=0.0006, unpaired t-test). There were no clinical signs of toxicity as determined by body weight (FIG. 35). Also on day 41, there was no significant difference between the mean body weight of the 7BD-33-11A treatment group versus the buffer control treatment group (p=0.5656, unpaired t-test). In addition, 7BD-33-11A treatment extended survival in comparison to the buffer control mice. All of the buffer control mice were euthanized due to CCAC end-points on day 41 (9 days before the end of treatment) while all of the 7BD-33-11A treated mice were still alive at day 55 (5 days after the end of treatment). Therefore, 7BD-33-11A treatment again appeared safe and has displayed efficacy and extended survival in the treatment of breast, prostate and now melanoma in vivo models of human cancer.

EXAMPLE 16

In Vivo A375 Established Tumor Experiments

Figure 36:
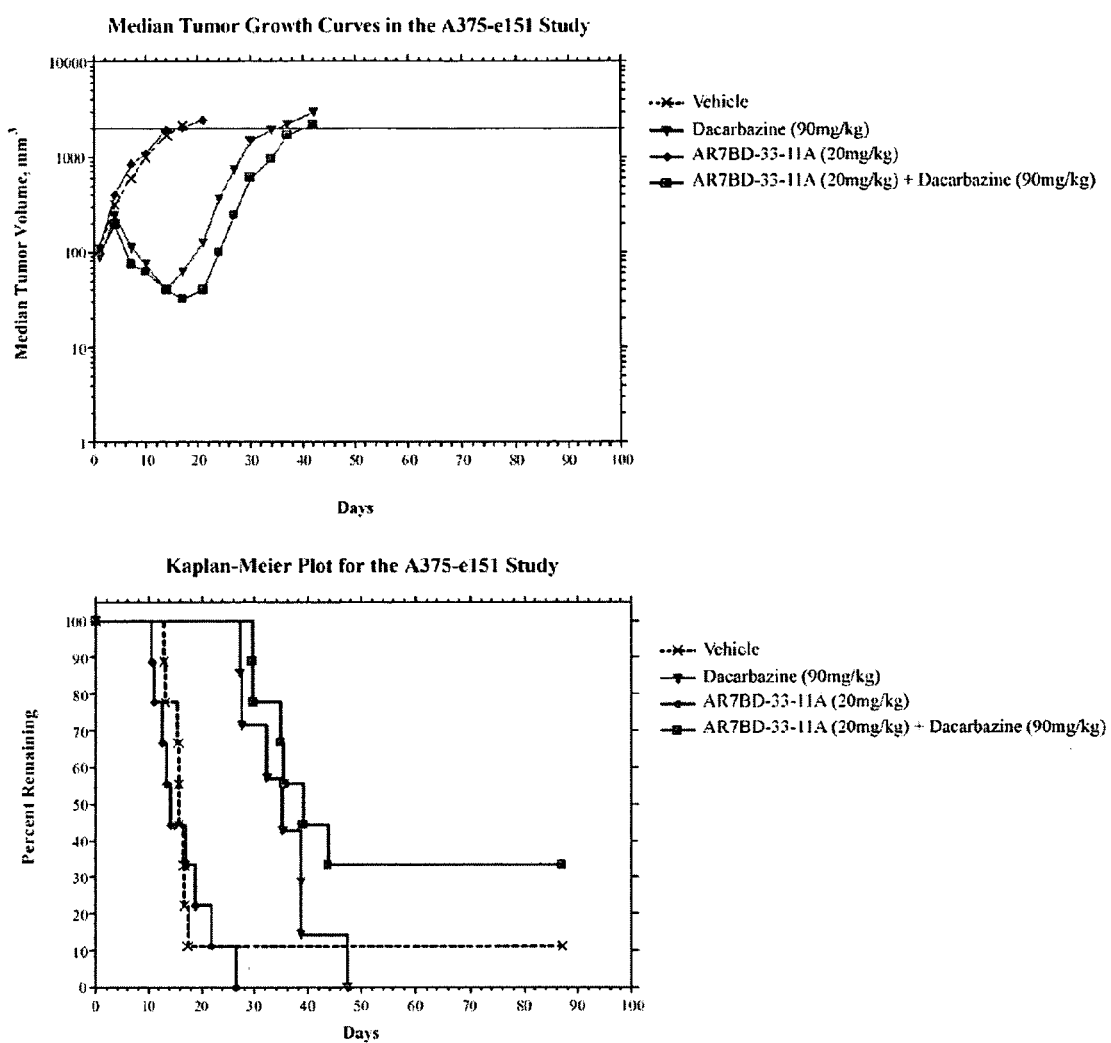
FIG. 36. Effect of AR7BD-33-11A and dacarbazine, alone and in combination, in an established A375 melanoma model. AR7BD-3311A and phosphate buffered saline (controls) were administered i.p. at 20 mg/kg three times per week for three weeks. Dacarbazine was administered i.p. at 90 mg/kg (½ the maximally tolerated does in this model) once daily for five consecutive days. Group median tumor growth and survival (Kaplan-Meier plot) curves are shown.

AR7BD-33-11A has also been tested alone and in conjunction with dacarbazine in an in vivo model of established melanoma. With reference to the data shown in FIG. 36, 1 mm³ tumor fragments derived from the A375 melanoma line maintained in athymic nude mice, were implanted s.c. into the flanks of test mice (athymic nude from Charles River, 14-15 weeks old on study Day 1). Tumors were monitored twice weekly and then daily as their volumes approached 80-120 mm³. Animals were sorted into treatment groups with tumor sizes of 62.5-144.0 mm³ and group mean tumor sizes of 101.0-102.2 mm³. AR7BD-3311A was administered ip. at 20 mg/kg three times per week for three weeks and dacarbazine was administered i.p. at 90 mg/kg (½ the maximally tolerated does in this model) once daily for five consecutive days. The control group received 0.2 mL/20 g body weight of phosphate-buffered saline, the AR7BD-33-11A vehicle, three times per week for three weeks. Treatments began on Day 1 in groups of ten nude mice bearing established (~102 mm³) melanomas. Tumor dimensions were measured twice weekly until tumors attained the 2,000-mm³ endpoint volume. Mice were euthanized once they reached this endpoint. The study was terminated on Day 87. Logrank tests determined whether there exists a significant difference (P<0.05) between the time-to-endpoint (TTE) values of drug-treated and vehicle-treated groups. Body weights of the animals were recorded for the duration of the study and the mice were examined frequently for overt signs of any adverse, drug-related side effects.

Vehicle treatment produced a median TTE of 15.8 days. One control mouse had no detectable tumor at the end of the study period, indicating a background of one unsatisfactory tumor engraftment per group, and one control mouse died of non-treatment-related causes. Negligible maximum mean body weight loss (<5%) was observed in the control group.

Dacarbazine monotherapy produced a median TTE of 35.1 days corresponding to a 122% delay in tumor growth as compared with the control mice. However, this decrease was insignificant, and no mice in this group survived to Day 87. Three mice died from non-treatment related causes; two of the excluded mice experienced complete tumor responses. The maximum mean body weight loss observed in this group was 5.2% on Day 7.

No significant delay in tumor growth and negligible maximum mean body weight loss (<5%) were observed with AR7BD-33-11A monotherapy.

In the AR7BD-33-11A/dacarbazinbe combination treatment group, a median TTE of 39.1 days, corresponding to a significant 147% delay in tumor growth (P<0.01), was observed. The combination treatment yielded 3 partial responses and 2 complete responses, with two of three 87-day survivors remaining tumor free at the end of the study. One mouse died of non-treatment related causes. The maximum mean body weight loss observed in this group was 3.1% on Day 7. No toxic deaths were observed in any groups in the study.

In summary, though AR7BD-33-11A treatment alone did not affect A375 melanoma growth in this model, it increased the efficacy of half the maximum tolerated dose of dacarbazine, yielding significant activity, an increase in survival, and an increased number of regression responses. Importantly, inclusion of AR7BD-33-11A did not modulate dacarbazine toxicity. The results suggest that AR7BD-33-11A may be used to enhance the efficacy of other, potentially more toxic, anti-cancer agents, allowing reduction of required drug dosages while maintaining tumor response and toxicity levels.

EXAMPLE 17

In Vivo BxPC-3 Preventative Tumor Experiments

With reference to FIGS. 37 and 38, 4 to 8 week old female SCID mice were implanted with 5 million BxPC-3 human melanoma cancer cells in 100 µL saline injected subcutaneously in the scruff of the neck. The mice were randomly divided into 2 treatment groups of 5. On the day after implantation 20 mg/kg of 7BD-33-11A test antibody or buffer control was administered intrapertioneally at a volume of 300 µL after dilution from the stock concentration with a diluent that contained 2.7 mM KCl, 1 mM $KH_2PO_4$, 137 mM NaCl and 20 mM $Na_2HPO_4$. The antibody or buffer control was then administered once per week for a period of 7 weeks in the same fashion.

Tumor growth was measured roughly every 7th day with calipers for up to 10 weeks or until individual animals reached the Canadian Council for Animal Care (CCAC) end-points. Body weights of the animals were recorded for the duration of the study. At the end of the study all animals were euthanised according to CCAC guidelines.

Figure 37:
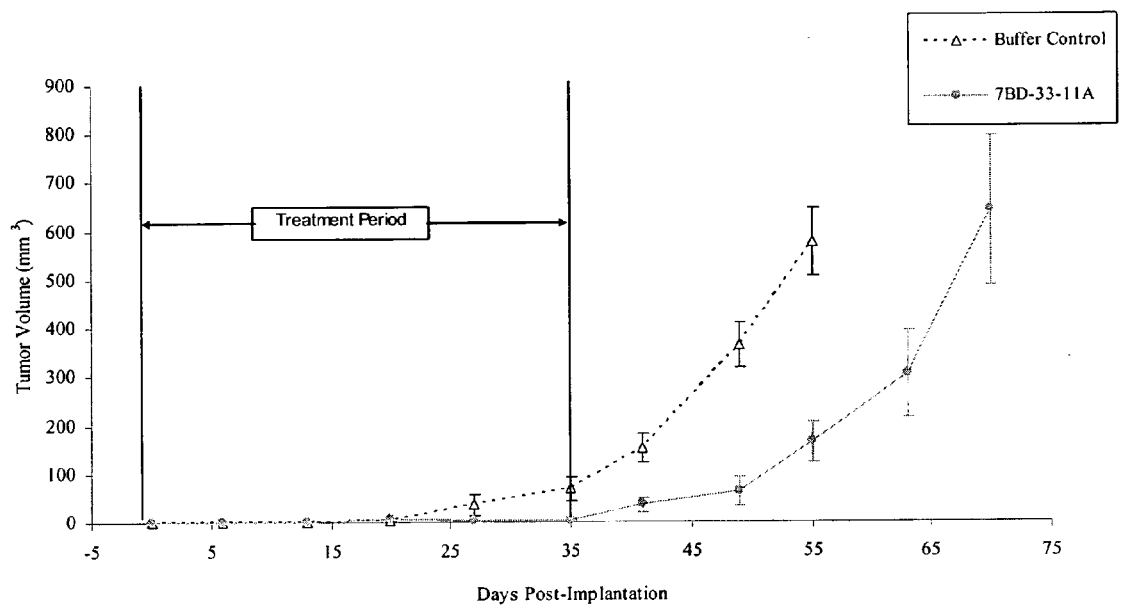
FIG. 37. Effect of 7BD-33-11A or buffer control on tumor growth in a preventative BxPC-3 pancreatic cancer model. The dashed line indicates the period during which the antibody was administered. Data points represent the mean +/−SEM.
Figure 38:
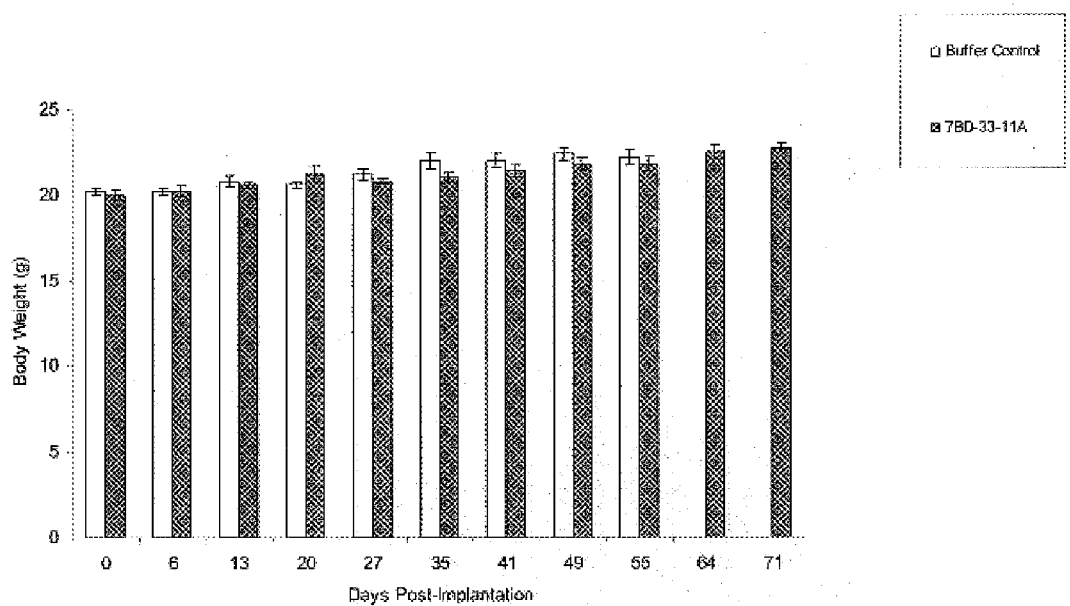
FIG. 38. Effect of 7BD-33-11A or buffer control on body weight in a preventative BxPC-3 pancreatic cancer model.

7BD-33-11A treatment resulted in decreased tumor growth compared to treatment with the buffer control (FIG. 37). On day 55 (5 days after the end of treatment), the mean tumor volume in the 7BD-33-11A treated group was 29 percent of the buffer control (p=0.0009, unpaired t-test). There were no clinical signs of toxicity as determined by body weight (FIG. 38). Also on day 55, there was no significant difference between the mean body weight of the 7BD-33-11A treatment group versus the buffer control treatment group (p=0.5368, unpaired t-test). In addition, 7BD-33-11A treatment extended survival in comparison to the buffer control mice. All of the buffer control mice were euthanized due to CCAC end-points on day 55 (5 days after the end of treatment) while 80 percent of the 7BD-33-11A treated mice were still alive at day 70 (20 days after the end of treatment). Therefore, 7BD-33-11A treatment again appeared safe and has displayed efficacy and extended survival in the treatment of breast, prostate, melanoma and now pancreatic in vivo models of human cancer.

EXAMPLE 18

NOD SCID Versus SCID In Vivo Preventative Tumor Experiment

With reference to the data shown in FIG. 39, 4 to 6 week old, female NOD SCID and SCID mice were implanted with 5 million MB-231 human breast cancer cells in 100 µL saline injected subcutaneously in the scruff of the neck. Each group of mice was randomly divided into 3 treatment groups of 10. On the day after implantation 20 mg/kg of H460-22-1 test antibody, 0.2 mg/kg of 7BD-33-11A test antibody or buffer control was administered intraperitoneally in a volume of 300 mL after dilution from the stock concentration with a diluent that contained 2.7 mM KCl, 1 mM $KH_2PO_4$, 137 mM NaCl and 20 mM $Na_2HPO_4$. The antibodies were then administered once per week for a period of 7 weeks in the same fashion.

Tumor growth was measured roughly every 7th day with calipers for up to 10 weeks or until individual animals reached the Canadian Council for Animal Care (CCAC) end-points. Body weights of the animals were recorded for the duration of the study. At the end of the study all animals were euthanised according to CCAC guidelines.

There were no clinical signs of toxicity throughout the study. Body weight measured at weekly intervals was a surrogate for well-being and failure to thrive. Body weights within each group increased over time.

Figure 39:
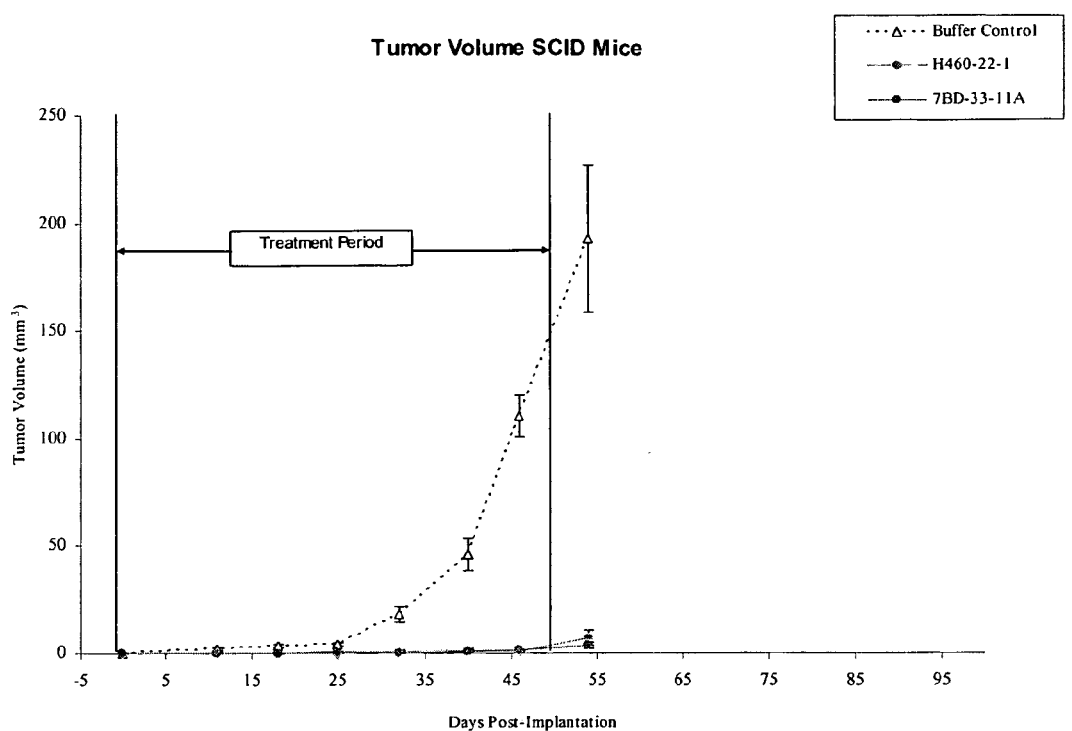
FIG. 39. Effect of 7BD-33-11A, H460-22-1 or buffer control on tumor growth in a preventative MDA-MB-231 breast SCID or NOD/SCID cancer model.
Figure 39:
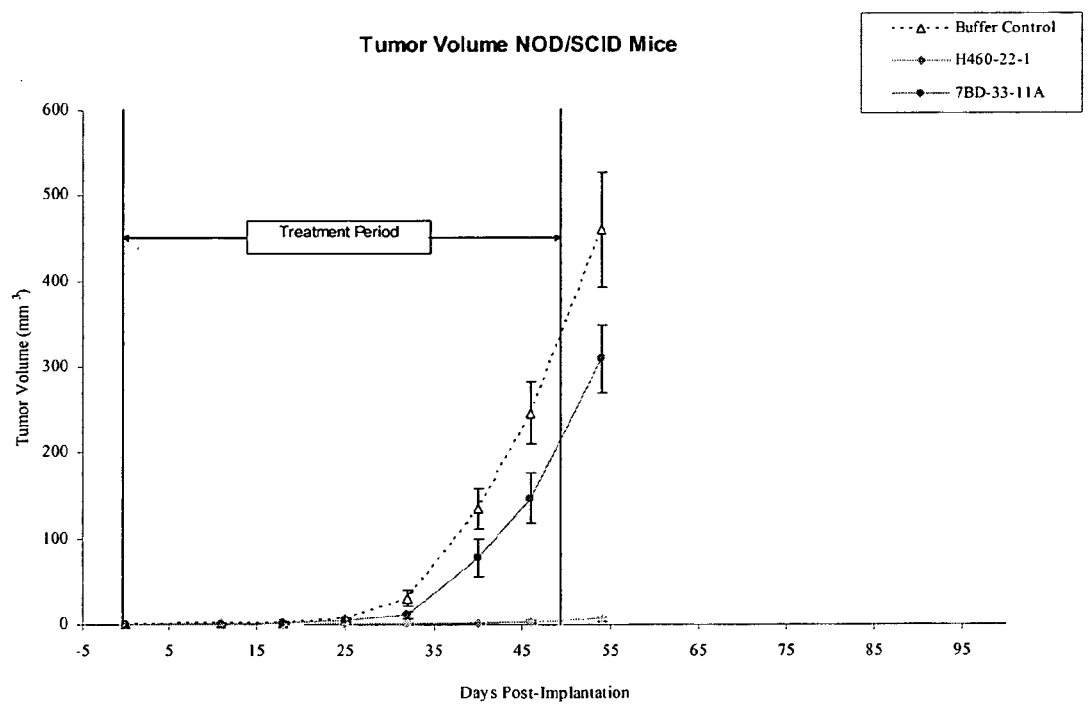

As illustrated in FIG. 39, on day 54 (4 days after the last treatment), in the SCID treated group, 7BD-33-11A and H460-22-1 treated mice developed tumors that were only 1.9 and 3.6 percent respectively of the mean tumor volume of the buffer control treated mice. Conversely, in the NOD SCID treated group, again on day 54 (4 days after the last treatment), 7BD-33-11A treated mice had tumor growth that was 67 percent of the mean tumor volume of the buffer control treated mice. Although this is still a decrease in mean tumor volume compared to the buffer control in the NOD SCID mice (p=0.0710, unpaired t-test), it is also a decrease in efficacy as compared to that observed in the SCID mice. H460-22-1 treated mice exhibited a similar effect as in the SCID mice; tumor growth was 1.4 percent of the mean tumor volume of the buffer control treated mice. Consequently, 7BD-33-11A activity in vivo seems to be in-part due to ADCC activity while H460-22-1's anti-tumor effect appears to be independent of ADCC.

The preponderance of evidence shows that 7BD-33-11A mediates anti-cancer effects through ligation of an epitope present on extracellular loop 2 on CD63. It has been shown, in Example 2, 7BD-33-11A antibody can be used to immunoprecipitate the cognate antigen from expressing cells such as MDA-MB-231 cells. Further it could be shown that the 7BD-33-11A antibody could be used in detection of cells and/or tissues which express a CD63 antigenic moiety which specifically binds thereto, utilizing techniques illustrated by, but not limited to FACS, cell ELISA or IHC.

Thus, it could be shown that the immunoprecipitated 7BD-33-11A antigen can inhibit the binding of 7BD-33-11A to such cells or tissues using FACS, cell ELISA or IHC assays. Further, as with the 7BD-33-11A antibody, other anti-CD63 antibodies could be used to immunoprecipitate and isolate other forms of the CD63 antigen, and the antigen can also be used to inhibit the binding of those antibodies to the cells or tissues that express the antigen using the same types of assays.

EXAMPLE 19

Determination of 7BD33-11A, ARH460-22-1, and AR1A245.6 Antigen Binding Affinity by BIAcore Analysis The antigen binding affinities of 7BD33-11A, ARH460-22-1, and AR1A245.6 were determined by BIAcore analysis. All experiments were conducted at a flow rate of 5 µl/min with Hanks Buffered Saline as running buffer (20 mM Hepes pH7.4, 150 mM NaCl, 3.4 mM EDTA, 0.005% tween 20). Anti-glutathione S-transferase (GST) antibody was first immobilized using a standard amine coupling procedure. In brief, the CM5 sensor chip was activated by injecting 35 µl of a mixture containing 0.05M N-hydroxysuccinimide and 0.2M 1-ethyl-3-(3-dimethylaminopropyl) carbodimide in $H_2O$ followed by anti-GST antibody at a 30 µg/ml concentration in 10 mM sodium acetate pH5.0 until 50,000 to 100,000 RU was captured. Finally, 35 µl of 1.0M ethanolamine-HCl pH 8.5 was injected to block any activated sites on the sensor chip surface. 25 µl GST-EC2 (recombinant fusion polypeptide of GST with the entire C-terminal domain of CD63) was then injected at 5 µg/ml followed by a 25-50 µl injection of the test antibody. Regeneration of the sensor chip surface for subsequent injections was accomplished by two 10 µl pulses of 20 mM glycine pH2.2. Test antibodies were serially injected at concentration ranging from 12.5 to 200 nM. As a control, each antibody concentration was injected over a surface where GST, instead of GST-EC2, was captured.

The affinity of the different antibodies for the EC2 domain was calculated from the measured steady state binding levels. For each sensorgram, a report point was taken 20 sec before the end of the antibody injection (resonance units at equilibrium or Req). For each antibody concentration, the Req obtained when antibody was injected over GST was subtracted from the Req obtained when the antibody was injected over the GST-EC2. The association constants ($K_A$), calculated from the slope of a Req/Conc. vs. Req plot, are shown in Table 29. The dissociation constants ($K_D$), also shown in Table 29 were calculated as the reciprocals of $K_A$.

TABLE 29

7BD33-11A, ARH460-22-1, and AR1A245.6 Antigen Binding Affinities by BIAcore Analysis

| Antibody | 7BD-33-11A | H460-22-1 | 1A245.6 |
|---|---|---|---|
| *$K_D$ (nM) | 135.0 | 41.7 | 9.8 |
| SEM | 30.4 | 8.3 | 2.9 |

*Data is the average and SEM of at least three independent experiments.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objects and obtain the ends and advantages mentioned, as well as those inherent therein. Any oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. The monoclonal antibody capable of specific binding to human CD63, in which the monoclonal antibody is the monoclonal antibody produced from the hybridoma cell line H460-22-1 having ATCC Accession No. PTA-4622.

2. The monoclonal antibody capable of specific binding to human CD63, in which the monoclonal antibody is the monoclonal antibody produced from the hybridoma cell line 1A245.6 having ATCC Accession No. PTA-4889.

3. A process for treating a human cancerous tumor which expresses human CD63 antigen comprising:

administering to an individual suffering from said human cancer, at least one monoclonal antibody selected from the group consisting of the isolated monoclonal antibody produced from the hybridoma cell line H460-22-1 having ATCC Accession No. PTA-4622, the isolated monoclonal antibody produced from the hybridoma cell line 1A245.6 having ATCC Accession No. PTA-4889, and the isolated monoclonal antibody produced from the hybridoma cell line 7BD-33-11A having ATCC Accession No. PTA-4890;

wherein administration of said at least one isolated monoclonal antibody is effective in reducing tumor burden.

4. A process for treating a human cancerous tumor which expresses human CD63 antigen comprising:

administering to an individual suffering from said human cancer, at least one monoclonal antibody selected from the group consisting of the isolated monoclonal antibody produced from the hybridoma cell line H460-22-1 having ATCC Accession No. PTA-4622, the isolated monoclonal antibody produced from the hybridoma cell line 1A245.6 having ATCC Accession No. PTA-4889, and the isolated monoclonal antibody produced from the hybridoma cell line 7BD-33-11A having ATCC Accession No. PTA-4890;

in conjunction with at least one chemotherapeutic agent;

wherein said administration of said at least one isolated monoclonal antibody is effective in reducing tumor burden.

5. A binding assay to determine a presence of cells which express an epitope or epitopes of CD63 in a primate tissue sample comprising:

providing a tissue sample from said primate;

providing at least one monoclonal antibody or antigen binding fragment selected from the group consisting of the isolated monoclonal antibody produced from the hybridoma cell line H461D-22-1 having ATCC Accession No. PTA-4622, the isolated monoclonal antibody produced from the hybridoma cell line 1A245.6 having ATCC Accession No. PTA-4889, and the isolated monoclonal antibody produced from the hybridoma cell line 7BD-33-11A having ATCC Accession No. PTA-4890;

contacting said at least one monoclonal antibody or antigen binding fragment thereof with said primate tissue sample; and determining binding of said at least one monoclonal antibody or antigen binding fragment thereof with said primate tissue sample;

whereby the presence of said cells in said primate tissue sample is indicated.

6. A binding assay to determine a presence of cancerous cells which express an epitope or epitopes of CD63 in a tissue sample selected from a human tumor comprising:

providing a tissue sample from said human tumor;

providing at least one monoclonal antibody or antigen binding fragment selected from the group consisting of the isolated monoclonal antibody produced from the hybridoma cell line H460-22-1 having ATCC Accession No. PTA-4622, the isolated monoclonal antibody produced from the hybridoma cell line 1A245.6 having ATCC Accession No. PTA-4889, and the isolated monoclonal antibody produced from the hybridoma cell line 7BD-33-11A having ATCC Accession No. PTA-4890;

contacting said at least one monoclonal antibody or antigen binding fragment thereof with said tissue sample; and determining binding of said at least one monoclonal antibody or antigen binding fragment thereof with said tissue sample;

whereby the presence of said cancerous cells in said tissue sample is indicated.

* * * * *